(12) United States Patent
Fensome et al.

(10) Patent No.: US 6,391,907 B1
(45) Date of Patent: May 21, 2002

(54) INDOLINE DERIVATIVES

(75) Inventors: Andrew Fensome; Lori L. Miller, both of Wayne; John W. Ullrich, Exton; Reinhold H. W. Bender, Valley Forge; Puwen Zhang, Audubon, all of PA (US); Jay E. Wrobel, Lawrenceville, NJ (US); Lin Zhi, San Diego, CA (US); Todd K. Jones, Solana Beach, CA (US); James P. Edwards, San Diego, CA (US); Christopher M. Tegley, Thousand Oaks, CA (US)

(73) Assignees: American Home Products Corporation, Madison, NJ (US); Ligand Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/552,632

(22) Filed: Apr. 19, 2000

Related U.S. Application Data

(60) Provisional application No. 60/183,058, filed on May 4, 1999.

(51) Int. Cl.[7] ............... A61K 31/4015; C07D 209/34; C07D 487/10; C07D 491/107; C07D 491/113

(52) U.S. Cl. ............... 514/409; 548/408; 548/409; 548/410

(58) Field of Search ............... 548/408, 409, 548/410; 514/409

(56) References Cited

U.S. PATENT DOCUMENTS

| | | | |
|---|---|---|---|
| 3,635,964 A | 1/1972 | Skorcz et al. | 260/247.1 |
| 3,917,592 A | 11/1975 | Kobzina | 260/244 |
| 4,093,730 A | 6/1978 | Butti | 424/270 |
| 4,258,185 A | 3/1981 | Nakao | |
| 4,440,785 A | 4/1984 | Walsh | 424/317 |
| 4,666,913 A | 5/1987 | Kubla et al. | 514/259 |
| 4,670,566 A | 6/1987 | Walsh | 548/485 |
| 4,721,721 A | 1/1988 | Kuhla | 514/312 |
| 4,822,794 A | 4/1989 | Spada | 514/230 |
| 4,831,027 A | 5/1989 | Narr et al. | 514/212 |
| 4,853,473 A | 8/1989 | Fischer et al. | 549/326 |
| 4,916,128 A | 4/1990 | Jonas | |
| 4,933,336 A | 6/1990 | Martin et al. | |
| 5,007,952 A | 4/1991 | Kume et al. | 71/73 |
| 5,171,851 A | 12/1992 | Kim et al. | 544/50 |
| 5,414,088 A | 5/1995 | Von Der Saal et al. | 546/158 |
| 5,453,516 A | 9/1995 | Fischer et al. | 548/543 |
| 5,475,020 A | 12/1995 | Johnson et al. | 548/466 |
| 5,521,166 A | 5/1996 | Grubb | 514/170 |
| 5,681,817 A | 10/1997 | Hodgen et al. | 514/12 |
| 5,688,808 A | 11/1997 | Jones et al. | 514/285 |
| 5,688,810 A | 11/1997 | Jones et al. | 514/311 |
| 5,693,646 A | 12/1997 | Jones et al. | 514/285 |
| 5,693,647 A | 12/1997 | Jones et al. | 514/285 |
| 5,696,127 A | 12/1997 | Jones et al. | 514/285 |
| 5,696,130 A | 12/1997 | Jones et al. | 514/291 |
| 5,696,133 A | 12/1997 | Pooley et al. | 514/314 |
| 5,719,136 A | 2/1998 | Chwalisz et al. | 514/170 |
| 5,733,902 A | 3/1998 | Schneider | 514/177 |
| 5,808,139 A | 9/1998 | Pathirana | 560/138 |
| 5,874,430 A | 2/1999 | Christ | 514/229.8 |
| 6,077,840 A | 6/2000 | Kurihara | 514/232.8 |

FOREIGN PATENT DOCUMENTS

| | | |
|---|---|---|
| DE | 3633861 | 4/1988 |
| DE | 43 30 234 | 3/1995 |
| DE | 43 44 463 | 6/1995 |
| EP | 022317 | 1/1981 |
| EP | 0 208 510 | 1/1987 |
| EP | 311135 | 4/1989 |
| EP | 385850 | 9/1990 |
| EP | 483077 | 9/1991 |
| EP | 454330 | 10/1991 |
| EP | 0 535 529 | 9/1992 |
| EP | 510235 | 10/1992 |
| EP | 947 507 | 10/1999 |
| EP | 978 279 | 2/2000 |
| JP | 63112584 | 5/1988 |
| WO | WO 86/03749 | 7/1986 |
| WO | WO 91/04974 | 4/1991 |
| WO | WO 91/06545 | 5/1991 |
| WO | WO 93/12085 | 6/1993 |
| WO | WO 94/14434 | 7/1994 |
| WO | WO 94/29272 | 12/1994 |
| WO | WO 95/11013 | 4/1995 |
| WO | WO 95/20389 | 8/1995 |
| WO | WO 95/20972 | 8/1995 |
| WO | WO 95/33746 | 12/1995 |
| WO | WO 96/15794 | 5/1996 |
| WO | WO 96/19458 | 6/1996 |

(List continued on next page.)

OTHER PUBLICATIONS

R.M. Evans, "The Steroid and Thyroid Hormone Receptor Superfamily", *Science*, 240:889 (May 13, 1988).
A. Ulmann et al., "Clinical Uses of Mifepristone (MFP)", *Ann. N.Y. Acad. Sci.*, 261:248 (Jun. 12, 1995).

(List continued on next page.)

*Primary Examiner*—Fiona T. Powers
(74) *Attorney, Agent, or Firm*—Howson and Howson

(57) ABSTRACT

This invention relates to substituted indoline derivative compounds which are antagonists of the progesterone receptor, their preparation and pharmaceutical utility, particularly including contraception and treatment of benign or malignant neoplastic diseases, having the general structure:

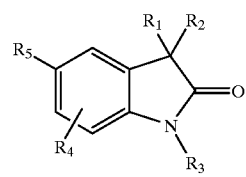

wherein $R^1$ and $R^2$ may be single substituents or fused to form spirocyclic rings.

13 Claims, No Drawings

FOREIGN PATENT DOCUMENTS

| WO | WO 96/19997 | 7/1996 |
|----|-------------|--------|
| WO | WO 97/13767 | 4/1997 |
| WO | WO 97/49407 | 12/1997 |
| WO | WO98/10765 A1 | 3/1998 |
| WO | WO 98/14436 | 4/1998 |
| WO | WO 98/27059 | 6/1998 |
| WO | WO 98/55116 | 12/1998 |
| WO | WO 99/10325 | 3/1999 |
| WO | WO 99/11264 | 3/1999 |
| WO | WO 99/15500 | 4/1999 |
| WO | WO 99/44608 | 9/1999 |

OTHER PUBLICATIONS

R. Kekkonen et al., "Sequential Regiment of the Antiprogesterone RU486 and Synthetic Progestin for Contraception", *Fertility and Sterility*, 60(4):610 (Oct. 1993).

K. Horwitz et al., "Progestin, Progesterone Receptors, and Breast Cancer", "Horm. Cancer", publisher: Birkhaeuser, Boston, Mass., ed. Vedeckis, pp. 283–306 (1996) abstract only.

A. A. Murphy et al., "Regression fo Uterine Leiomyomata in Response to the Antiprogesterone RU 486", *J. Clin. Endo. Metab.*, 76(2):513 (Feb. 1993).

L. M. Kettel et al., "Endocrine Response to Long–Term Administration of the Antiprogesterone RU486 in Patients with Pelvic Endometriosis", *Fertility and Sterility*, 56(3):402 (Sep. 1991).

H. Michna et al., "Differentiation Therapy with Progesterone Antagonists", *Ann. N.Y. Acad. Sci.*, 761:224 (Jun. 1995).

L. Zhi et al., "5–Aryl–1,2–Dihydrochromeno[3,4–f]quinolines: A Novel Class of Nonsteroidal Human Progesterone Receptor Agonists", *J. Med. Chem.*, 41(3):291 (Oct. 22, 1998).

D. W. Combs et al., "Nonsteroidal Progesterone Receptor Ligands. 2. High–Affinity Ligands with Selectivity for Bone Cell Progesterone Receptors", *J. Med. Chem.*, 38:4880 (Dec. 8, 1995).

K. L. Perlman et al., "20–Oxopregnacalciferols: Vitamin D Compounds that Bind the Progesterone Receptor", *Tet. Letters*, 35(15):2295 (1994).

L. G. Hamann et al., "Synthesis and Biological Activity of Novel Nonsteroidal Progesterone Receptor Antagonists", *Ann. N.Y. Acad. Sci.*, 761:383 (Jun. 12, 1995).

R. H. K. Chen et al., "Synthesis and SAR of a Novel Series of Spirobenzothlzaepine Derivatives with Antiprogestin Activity", POI–37, 16$^{th}$ Int. Cong. Het. Chem., Montana (1997).

B. Narr et al., "Preparation, Testing, and Formulation of Imidazobenzoxazinones as Cardiotonics", *Chemical Abstracts*, 109:22973 (1988).

R. J. Hartmann et al., "Effects of Brofoxine, A New Anxiolytic on Experimentally Induced Conflict in Rats", *Proc West. Pharmacol. Soc.*, 21:51–55 (1978).

B. Singh et al., "Novel cAMP PDE III Inhibitor: Imidazo [4,5–b]pyridin–2(3H)–ones and Thiazolo[4,5–b] pyridin–2(3H)–ones and Their Analogs", *J. Med. Chem.*, 37:248 (Jan. 21, 1994).

A. Andreani et al., "Potential Antitumor Agents XVII (1). Cytotoxic Agents from Indole Derivatives and Their Intermediates", *Acta. Pharm. Nor.*, 2(6):407 (1990).

Sakata et al., "Silver Halide Photographic Materials Useful for Platemaking", *Chemical Abstracts*, 123:301–1431 (1993).

P. Pflegel et al., "Polarografie con 7–Chlor–5–phenyl–2–thioxo–1H–2,3–dihydro–1,3,4–benzotriazepinen", *Pharmazie*, 37(10): 714–717 (1982).

E. I. Barengolts et al., "Progesterone Antagonist RU 486 Has Bone–Sparing Effects in Ovariectomized Rats", *Bone*, 17(1):21 (Jul. 1995).

E. V. Gromachevskaya et al., "Studies of 4H–3, 1–Benzoxazines", *Chem. Heterocycl. Cmpds.* 33(10):1209–1214 (1997).

D. Chiarno et al., "2, 1–Benzisothiazoline, 2,2–Dioxide and Derivatives", *J. Heterocycl. Chem.*, 23(6):1645–1649 (Nov.– Dec. 1986).

A. Turck et al., "On the Metabolism of 3–Substituted and 3,6–Disubstituted Pyridazines", *Tetrahedron*, 49(3):599–606 (1993).

V. Kumar et al., "Synthesis of 7–Azaindole and 7–Azaoxindole Derivatives through a Palladium–Catalyzed Cross–Coupling Reaction", *J. Org. Chem.*, 57(25):6995–6998 (1992).

P. Canonne et al., "Spirocyclization of 1–(o–Aminophenyl) cycloalkanols and 1–(2'–Amino–3'–pyridinyl)cycloalkanols", *J. Heterocyclic Chem.*, 26:113 (Jan.–Feb. 1989).

M–C. Forest et al., "A Novel Class of Cardiotonic Agents: Synthesis and Biological Evaluation of 5–Substituted 3,6–Dihydothiadiazin–2–ones with Cycli AMP Phosphodiesterase Inhibiting and Myofibrillar Calcium Sensitizing Properties", *J. Med. Chem.*, 35:163–172 (Jan. 1992).

D. W. Combs et al., "Heteroatom Analogues of Bemoradan: Chemistry and Cardiotonic Activity of 1, 4–Benzothaizinylpyridazinones",*J. Med. Chem.*, 35:172–176 (Jan. 1992).

Kurihari et al., "Synthesis of (±)–PF1092A, B, and C; New Nonsteroidal Progesteron Receptor Ligands", *J. Antibiotics*, 50(4):360 (Apr. 1997).

A. Kende et al., "Regioselective C–3 Alkylation of Oxindole Dianion", *Synth. Commun.* 12(1):1 (1982).

T. Tucker et al., "Synthesis of a Series of 4–(Arylethylnyl)–6–Chloro–4–Cyclopropyl–3, 4–dihydroquinazolin–2(1H)–ones as Novel Non–Nucleoside HIV–1 Reverse Transcriptase Inhibitors", *J. Med. Chem.*, 37:2347–2444 (Jul. 22, 1994).

J. P. Edwards et al., "5–Aryl–1,2–Dihydro–5H–Chromeno [3,4–f]Quinolines as Potent, Orally Active, Nonsteroidal Progesterone Receptor Agonists: The Effect of D–Ring Substituents", *J. Med. Chem.*, 41:303–310 (Jan. 29, 1998).

Derwent WPI abstract, "New Imidazo–Pyridine Derivatives—Useful as Platelet Agglutination Inhibition, Antiallergic, Antiinflammatory Sedative, Cardiac, and Cardiovascular Vasodilators", JP 63112584.

Derwent WPI abstract, N. Brumagniez et al., "Benzimidazole and Azabenzimidazole(s)—Having Cardiotonic, Vasodilating, Anti–Hypertensive, Anti–Aggregation, and Anti–Ulcer Activity", EP 385850.

Derwent WPI asbtract, F. Arndt et al., "New Heterocycle substituted Benzo–Fused Azine and Azole Derivatives—Useful as Selective Herbicides for Pre or Post–Emergence Application", EP 311135.

K. Horwitz et al., "Progestin, Progesterone Receptors, and Breast Cancer", "Hormones and Cancer", publisher: Birkhaeuser, Boston, Mass., ed. Vedeckis, pp. 283–306 (1996).

Mamaev, V.P., et al., "Synthesis of 4H–Thieno [3,2–B] Pyrrol–5(6H)–One"Bulletin of the Academy of Sciences on the USSR. Division of Chemical Science, US, Consultants Bureau, New York. vol. 9, pp. 1549–1553, 1966.

Derwent WPI Abstract, Chwalisz, K., et al. "Contraceptive Pack for Implantation Inhibition –Contains Competivitive Progesterone Antagonist and Gestagen for Sequential Oral Administration.", DE 4,344,463.

Kolasa, K., et al., "Preliminary Pharmacological Studies of the Central Action of Phenyl and Piperidinomethyl Derivatives of 2–Benzoxazolone." *Chemical Abstracts*, vol. 99, No. 1, Abst. No. 157a, Jul. 4, 1983.

Meanwell N.A., et al., "Regiospecific Functionalization of 1,3–dihydro–2h–Benimidazol–2–One and Structurally Related Cyclic Urea Derivatives"*J. Organic Chem.*, 60(6): 1565µ(Mar. 24, 1995).

Derwent WPI Abstract, Chwalisz, K., et al. "Female Contraceptive Method Comprises Gestation Treatment with Intermittent Progesterone Antagonist Administration.", DE 4,33,234.

Singh, B., et al., "An Efficient and Novel Synthesis of Fused Thiazol–2(3H)–ones"*Heterocycles*, 36(1): 133–134, p. 136, compounds 16a, 18a, Jan. 1993.

Vernin, G., et al., "Etude Dans la Serie des Radicaux Heterocycliques. Partie XV. decomposition aprotique de 1'amino–6–ethyl–2–benzothiazole dans des substrats aromatiques et heteroaromatiques: preparation des mesityl–6–et furyl–6–ethyl–2–benzothiazoles, des sels quaternaires et des spiropyrannes correspondants" *Helvetica Chimica Acta*, 62(1/3):21–30 Jan. 24, 1979.

INDOLINE DERIVATIVES

CROSS-REFERENCE TO RELATED APPLICATIONS

This application claims the benefit of the priority of U.S. Provisional Patent Application No. 60/183,058, filed May 4, 1999.

FIELD OF THE INVENTION

This invention relates to compounds which are antagonists of the progesterone receptor, their preparation and utility.

BACKGROUND OF THE INVENTION

Intracellular receptors (IR) form a class of structurally related gene regulators known as "ligand dependent transcription factors" (R. M. Evans, Science, 240, 889, 1998). The steroid receptor family is a subset of the IR family, including progesterone receptor (PR), estrogen receptor (ER), androgen receptor (AR), glucocorticoid receptor (GR), and mineralocorticoid receptor (MR).

The natural hormone, or ligand, for the PR is the steroid progesterone, but synthetic compounds, such as medroxyprogesterone acetate or levonorgestrel, have been made which also serve as ligands. Once a ligand is present in the fluid surrounding a cell, it passes through the membrane via passive diffusion, and binds to the IR to create a receptor/ligand complex. Once bound to the DNA the complex modulates the production of mRNA and protein encoded by that gene.

A compound that binds to an IR and mimics the action of the natural hormone is termed an agonist, whilst a compound which inhibits the effect of the hormone is an antagonist.

PR antagonists may be used in contraception. In this context they may be administered alone (Ulmann, et al, *Ann. N.Y. Acad. Sci.*, 261, 248, 1995), in combination with a PR agonist (Kekkonen, et al, *Fertility and Sterility*, 60, 610, 1993) or in combination with a partial ER antagonist such as tamoxifen (WO 96/1997 A1 Jul. 4, 1996).

PR antagonists may also be useful for the treatment of hormone dependent breast cancers (Horwitz, et al, Horm. Cancer, 283, pub: Birkhaeuser, Boston, Mass., ed. Vedeckis) as well as uterine and ovarian cancers. Pr antagonists may also be useful for the treatment of non-malignant chronic conditions such as fibroids (Murphy, et al, *J. Clin. Endo. Metab.*, 76, 513, 1993) and endometriosis (Kettel, et al, *Fertility and Sterility*, 56, 402, 1991).

PR antagonists may also be useful in hormone replacement therapy for post menopausal patients in combination with a partial ER antagonist such as tamoxifen (U.S. Pat. No. 5,719,136).

PR antagonists, such as mifepristone and onapristone, have been shown to be effective in a model of hormone dependent prostate cancer, which may indicate their utility in the treatment of this condition in men (Michna, et al, *Ann. N.Y. Acad. Sci.*, 761, 224, 1995).

The compounds of this invention have been shown to act as competitive inhibitors of progesterone binding to the PR and act as antagonists in functional models, either/or in-vitro and in-vivo. These compounds may be used for contraception, in the treatment of fibroids, endometriosis, breast, uterine, ovarian and prostate cancer, and post menopausal hormone replacement therapy.

Described by Jones, et al, (U.S. Pat. No. 5,688,810) is the PR antagonist dihydroquinoline A.

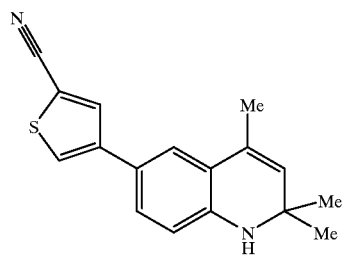

Jones, et al, described the enol ether B (U.S. Pat. No. 5,693,646) as a PR ligand.

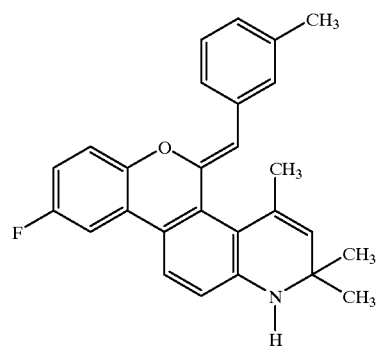

Jones, et al, described compound C (U.S. Pat. No. 5,696,127) as a PR ligand.

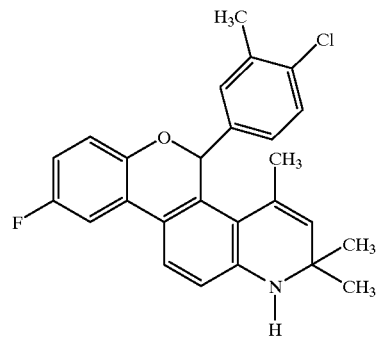

Zhi, et al, described lactones D, E and F as PR antagonists (J. Med. Chem., 41, 291, 1998).

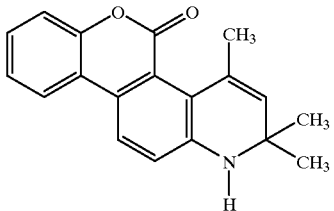

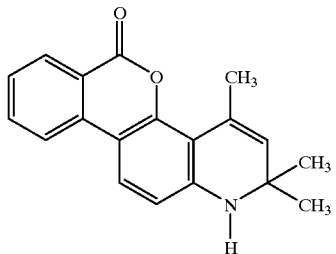

E

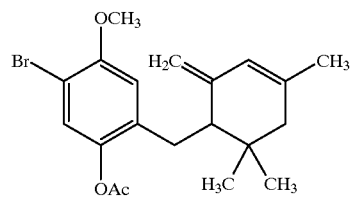

I

Hamann, et al, described the PR antagonist J (*Ann. N.Y Acad. Sci.,* 761, 383, 1995).

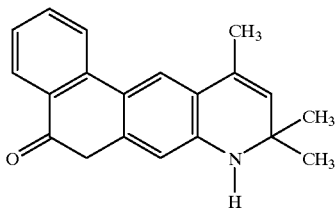

F

Zhi, et al, described the ether G as a PR antagonist (*J. Med. Chem.,* 41, 291, 1998).

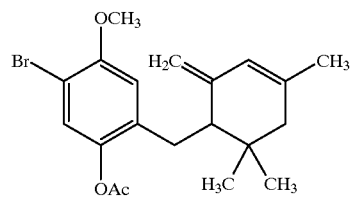

J

Chen, et al, described the PR antagonist K (Chen, et al, POI-37, 16<sup>th</sup> Int. Cong. Het. Chem., Montana, 1997).

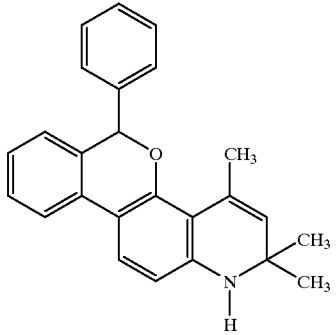

G

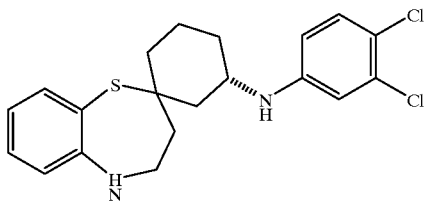

K

Combs, et al., disclosed the amide H as a ligand for the PR (*J. Med. Chem.,* 38, 4880, 1995).

Kurihari, et. al., described the PR ligand L (*J. Antibiotics,* 50, 360, 1997).

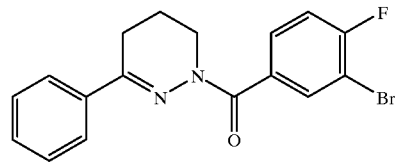

H

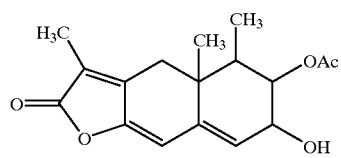

L

Perlman, et. al., described the vitamin D analog I as a PR ligand (*Tet. Letters,* 35, 2295, 1994).

Kuhla, et al, disclosed the oxindole M as having cardiotonic activity (WO 86/03749).

Weber, teaches the oxindole N for cardiovascular indications (WO 91/06545).

N

Fischer, et al, describe a preparation for making compounds which include the generic structure O (U.S. Pat. No. 5,453,516).

O

R = various

Singh, et al, described the PDE III inhibitor P (*J. Med. Chem.*, 37, 248, 1994).

P

Andreani, et al, described the cytotoxic agent Q (*Acta. Pharn. Nord.*, 2, 407, 1990).

P

Binder, et al, described structure R which is an intermediate for preparing COX II inhibitors (WO 97/13767).

Walsh described the oxindole S as an intermediate (U.S. Pat. Nos. 4,440,785, 4,670,566).

S $R_1$ = F, Cl, Br, alkyl, $NH_2$
$R_2$ = alkyl, alkoxy, F, Cl, NH2, $CF_3$

Bohm, et al, claim the oxindole T as cardiovascular agents (WO 91/06545).

T

Bohm, et al, include the generic structure U (WO 91/04974).

U

JP 63112584 A contains the generic structure V:

V

Boar, et al, described the dioxolane W as an intermediate for preparation of acetyl-cholinesterase inhibitors (WO 93/12085 A1).

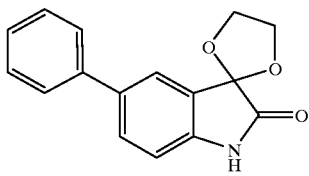

W

Kende, et al, described methodology for preparing 3,3-substituted oxindoles, e.g. X, that was utilized in the present invention (Synth. Commun., 12, 1, 1982).

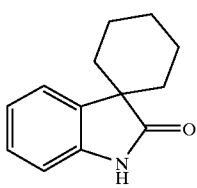

X

DESCRIPTION OF THE INVENTION

This invention comprises compounds of the Formula 1:

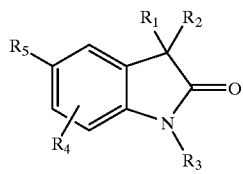

1 wherein:
$R_1$ and $R_2$ are chosen independently from H, alkyl, substituted alkyl; OH; O(alkyl); O(substituted alkyl); OAc; aryl; optionally substituted aryl; heteroaryl; optionally substituted heteroaryl; alkylaryl; alkylheteroaryl; 1-propynyl; or 3-propynyl;

or $R_1$ and $R_2$ are joined to form a ring comprising one of the following:
—$CH_2(CH_2)_nCH_2$—; —$CH_2CH_2CMe_2CH_2CH_2$—; —$O(CH_2)_mCH_2$—; $O(CH_2)_pO$; —$CH_2CH_2OCH_2CH_2$—; or —$CH_2CH_2N$(H or alkyl)$CH_2CH_2$—;

or $R_1$ and $R_2$ comprise a double bond to $CMe_2$, C(cycloalkyl), O, or C(cyloether);

n is an integer from 0 to 5;
m is an integer from 1 to 4;
p is an integer from 1 to 4;
$R_3$ is selected from H, OH, $NH_2$, $C_1$ to $C_6$ alkyl, substituted $C_1$ to $C_6$ alkyl, $C_3$ to $C_6$ alkenyl, alkynyl or substituted alkynyl, or $COR^A$;
$R^A$ is selected from H, $C_1$ to $C_3$ alkyl, substituted $C_1$ to $C_3$ alkyl, $C_1$ to $C_3$ alkoxy, substituted $C_1$ to $C_3$ alkoxy, $C_1$ to $C_3$ aminoalkyl, or substituted $C_1$ to $C_3$ aminoalkyl;
$R_4$ is selected from H, halogen, CN, $NH_2$, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, or substituted $C_1$ to $C_6$ aminoalkyl;
$R_5$ is selected from the groups a), b) or c):

a) $R^5$ is a trisubstituted benzene ring containing the substituents X, Y and Z as shown below:

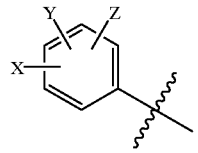

wherein:
X is selected from the group of halogen, OH, CN, $C_1$ to $C_3$ alkyl, substituted $C_1$ to $C_3$ alkyl $C_1$ to $C_3$ alkoxy, substituted $C_1$ to $C_3$ alkoxy, $C_1$ to $C_3$ thioalkyl, substituted $C_1$ to $C_3$ thioalkyl, S(O)alkyl, $S(O)_2$alkyl, $C_1$ to $C_3$ aminoalkyl, substituted $C_1$ to $C_3$ aminoalkyl, $NO_2$, $C_1$ to $C_3$ perfluoroalkyl, 5 or 6 membered heterocyclic ring containing 1 to 3 heteroatoms, $COR^B$, $OCOR^B$, or $NR^CCOR^B$;
$R^B$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;
$R^C$ is H, $C_1$ to $C_3$ alkyl, or substituted $C_1$ to $C_3$ alkyl;
Y and Z are independently selected from H, halogen, CN, $NO_2$, $C_1$ to $C_3$ alkoxy, $C_1$ to $C_3$ alkyl, or $C_1$ to $C_3$ thioalkyl; or b) $R^5$ is a five or six membered heterocyclic ring with 1, 2, or 3 heteroatoms selected from O, S, SO, $SO_2$ or $NR^6$ and containing one or two independent substituents from the group of H, halogen, CN, $NO_2$ and $C_1$ to $C_3$ alkyl, $C_1$ to $C_3$ alkoxy, $C_1$ to $C_3$ aminoalkyl, $COR^D$, or $NR^ECOR^D$;
$R^D$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;
$R^E$ is H, $C_1$ to $C_3$ alkyl, or substituted $C_1$ to $C_3$ alkyl;
$R^6$ is H, or $C_1$ to $C_3$ alkyl; or c) $R^5$ is an indol-4-yl, indol-7-yl or benzo-2-thiophene moiety, the moiety being optionally substituted by from 1 to 3 substituents selected from halogen, lower alkyl, CN, $NO_2$, lower alkoxy, or $CF_3$;

or a pharmaceutically acceptable salt thereof.

A preferred set of compounds of this invention is depicted by structure 2, 2a:

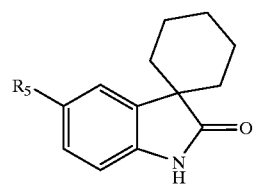

2

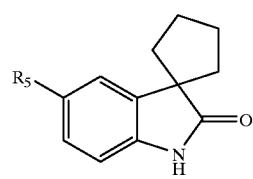

2a wherein:
$R^5$ is a disubstituted benzene ring containing the substituents X and Y as shown below:

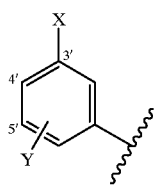

X is taken from the group of halogen, CN, $C_1$ to $C_3$ alkoxy, $C_1$ to $C_3$ alkyl, $NO_2$, $C_1$ to $C_3$ perfluoroalkyl, 5 membered heterocyclic ring containing 1 to 3 heteroatoms or $C_1$ to C3 thioalkoxy;

Y is a substituent on the 4' or 5' position of the disubstituted benzene ring selected from the group of H, halogen, CN, $NO_2$, $C_1$ to $C_3$ alkoxy, $C_1$ to $C_4$ alkyl, or $C_1$ to $C_3$ thioalkyl;

or a pharmaceutically acceptable salt thereof.

Another preferred group of this invention comprises compounds of formulas 2 and 2a wherein $R^5$ is a five membered ring with the structure shown below:

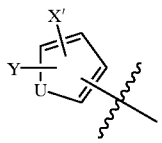

U is O, S, or $NR^6$, $R^6$ is H, or $C_1$ to $C_3$ alkyl, $C_1$ to $C_4$ $CO_2$alkyl, X' is selected from the group of halogen, CN, $NO_2$, $C_1$ to $C_3$ alkyl or $C_1$ to $C_3$ alkoxy; with a proviso that, when X' is CN, U is not $NR^6$;

Y' is selected from H, F, CN, $NO_2$ or $C_1$ to $C_4$ alkyl;

or a pharmaceutically acceptable salt thereof.

Another preferred group of formulas 2 and 2a are those in which $R^5$ is a six membered ring with the structure shown

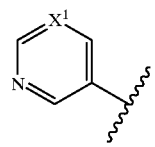

wherein:

$X^1$ is N or $CX^2$, $X^2$ is halogen, CN or $NO_2$;

or pharmaceutically acceptable salt thereof

The compounds of this invention may contain an asymmetric carbon atom and some of the compounds of this invention may contain one or more asymmetric centers and may thus give rise to optical isomers and diastereomers. While shown without respect to stereochemistry in Formula 1 and 2 the present invention includes such optical isomers and diastereomers; as well as the racemic and resolved, enantiomerically pure R and S stereoisomers; as well as other mixtures of the R and S stereoisomers and pharmaceutically acceptable salts thereof.

The term "alkyl" is used herein to refer to both straight- and branched-chain saturated aliphatic hydrocarbon groups having 1 to 8 carbon atoms; "alkenyl" is intended to include both straight- and branched-chain alkyl group with 1 or 2 carbon-carbon double bonds and containing 2 to 8 carbon atoms; "alkynyl" group is intended to cover both straight- and branched-chain alkyl group with at least 1 or 2 carbon-carbon triple bonds and containing 2 to 8 carbon atoms.

The terms "substituted alkyl", "substituted alkenyl", and "substituted alkynyl" refer to alkyl, alkenyl, and alkynyl as just described having one or more substituents from the group including halogen, CN, OH, $NO_2$, amino, aryl, heterocyclic, substituted aryl, substituted heterocyclic, alkoxy, aryloxy, substituted alkyloxy, alkylcarbonyl, alkylcarboxy, alkylamino, arylthio. These substituents may be attached to any carbon of alkyl, alkenyl, or alkynyl group provided that the attachment constitutes a stable chemical moiety.

The term "aryl" is used herein to refers to an aromatic system which may be a single ring or multiple aromatic rings fused or linked together as such that at least one part of the fused or linked rings forms the conjugated aromatic system. The aryl groups include, but are not limited to, phenyl, naphthyl, biphenyl, anthryl, tetrohydronaphthyl, phenanthryl.

The term "substituted aryl" refers to aryl as just defined having 1 to 4 substituents from the group including halogen, CN, OH, $NO_2$, amino, alkyl, cycloalkyl, alkenyl, alkynyl, alkoxy, aryloxy, substituted alkyloxy, alkylcarbonyl, alkylcarboxy, alkylamino, or arylthio.

The term "heterocyclic" is used herein to describe a stable 4- to 7-membered monocyclic or a stable multicyclic heterocyclic ring which is saturated, partially unsaturated, or unsaturated, and which consists of carbon atoms and from one to four heteroatoms selected from the group including N, O, and S atoms. The N and S atoms may be oxidized. The heterocyclic ring also includes any multicyclic ring in which any of above defined heterocyclic rings is fused to an aryl ring. The heterocyclic ring may be attached at any heteroatom or carbon atom provided the resultant structure is chemically stable. Such heterocyclic groups include, but are not limited to, tetrahydrofuran, piperidinyl, piperazinyl, 2-oxopiperidinyl, azepinyl, pyrrolidinyl, imidazolyl, pyridyl, pyrazinyl, pyrimidinyl, pyridazinyl, oxazolyl, isoxazolyl, morpholinyl, indolyl, quinolinyl, thienyl, furyl, benzofuranyl, benzothienyl, thiamorpholinyl, thiamorpholinyl sulfoxide, and isoquinolinyl.

The term "substituted heterocyclic" is used herein to describe the heterocyclic just defined having 1 to 4 substituents selected from the group which includes halogen, CN, OH, $NO_2$, amino, alkyl, substituted alkyl, cycloalkyl, alkenyl, substituted alkenyl, alkynyl, alkoxy, aryloxy, substituted alkyloxy, alkylcarbonyl, alkylcarboxy, alkylamino, or arylthio.

The term "thioalkyl" is used herein to refer to the SR group, where R is alkyl or substituted alkyl, containing 1 to 8 carbon atoms, preferably 1 to 6 carbon atoms. The term "alkoxy" is used herein to refer to the OR group, where R is alkyl or substituted alkyl, containing 1 to 8 carbon atoms, preferably 1 to 6 carbon atoms. The term "aryloxy" is used herein to refer to the OR group, where R is aryl or substituted aryl, as defined above. The term "alkylcarbonyl" is used herein to refer to the RCO group, where R is alkyl or substituted alkyl, containing 1 to 8 carbon atoms, preferably 1 to 6 carbon atoms. The term "alkylcarboxy" is used herein to refer to the COOR group, where R is alkyl or substituted alkyl, containing 1 to 8 carbon atoms, preferably 1 to 6 carbon atoms. The term "aminoalkyl" refers to both secondary and tertiary amines wherein the alkyl or substituted alkyl groups, containing 1 to 8 carbon atoms, preferably 1 to 6 carbon atoms, which may be either the same or different and the point of attachment is on the nitrogen atom. The term "halogen" refers to Cl, Br, F, or I.

The compounds of this invention may be prepared according to the methods described below.

Scheme 1

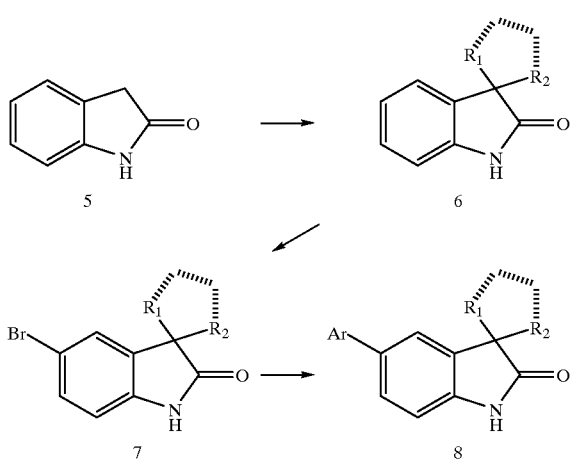

According to scheme 1, commercially available oxindole 5 is treated with mixture a strong organo-metallic base (e.g. butyl lithium, lithium diisopropylamide, potassium hexamethyldisilazide) in an inert solvent (e.g. THF, diethyl ether) under nitrogen at reduce temperature (ca. −20° C.) (Kende, et al, Synth. Commun., 12, 1, 1982). The resulting di-anion is then treated with excess electrophile such as an alkyl halide, preferably the iodide. If $R_1$ and $R_2$ are to be joined such as the product 6 contains a spirocycle at position 3, then the electrophile should be bifunctional, i.e. a diiodide. Subsequent bromination of 6 proceeds smoothly with bromine in acetic acid (an organic co-solvent such as dichloromethane may be added as required) in the presence of sodium acetate, to afford the aryl bromide 7. The bromide 7 is reacted with a palladium salt (e.g. tetrakis(triphenylphoshine)palladium(0)), in a suitable solvent (e.g. THF, dimethoxyethane, ethanol, toluene) at room temperature under an inert atmosphere (argon, nitrogen). The mixture is then treated with an arylboronic acid or boronic acid ester and a base (sodium carbonate, triethylamine, potassium phosphate) in water or fluoride source (cesium fluoride) under anhydrous conditions. The required product 8 is then isolated and purified by standard means.

If $R_1$ and $R_2$ are different, then the intermediate 6 is prepared by reacting the dianion of 5 with one equivalent of the electrophile $R_1$—X (X=leaving group e.g. I). The resultant mono-alkylated compound may be then isolated and re-subjected to the reaction conditions using $R_2$—X, or alternatively used in-situ for the second alkylation with $R_2$—X. Alternatively if the desired product 8 is to contain $R_2$=H, then the isolated mono-alkylated intermediate is taken though the subsequent steps.

Scheme 2

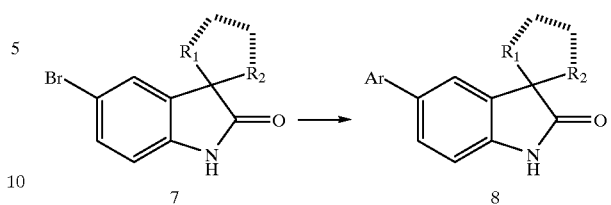

Other methodologies are also available for coupling the pendant aryl group, Ar, to the oxindole platform, for example reaction of compound 7 with an aryl stannane, aryl zinc, or aryl magnesium halide in the presence of a palladium or nickel catalyst (scheme 2). The required arylmetallic species described above are formed through standard techniques.

Other functionalities can easily be installed into the 3-position of the indoline platform according to scheme 3. Oxidation of the unsubstituted indoline 9, preferably under neutral or acidic conditions (e.g. selenium dioxide in dry dioxane at reflux) affords the isatin 10. Compound 10 may be further functionalized to provide a ketal 11 by treatment with an alcohol and acid catalyst under dehydrating conditions. Alternatively reaction of 10 with a second ketone under suitable conditions (piperidine in toluene at reflux; or $TiCl_4/Zn$ in THF at reflux) affords alkylidene derivatives 12. Reaction of the isatin 10 with a grignard reagent or organolithium affords tertiary alcohols 13 (R=H). These alcohols may then be further functionalized by alkylation or acylation procedures.

Scheme 3

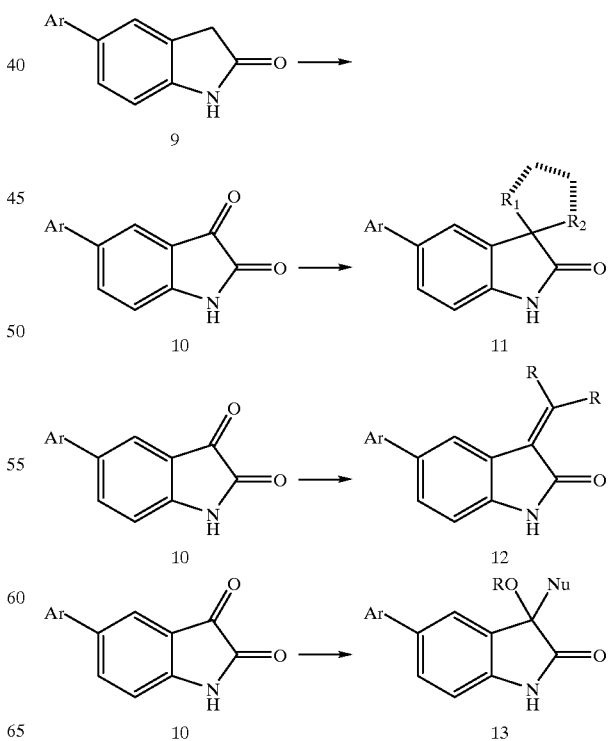

Scheme 4

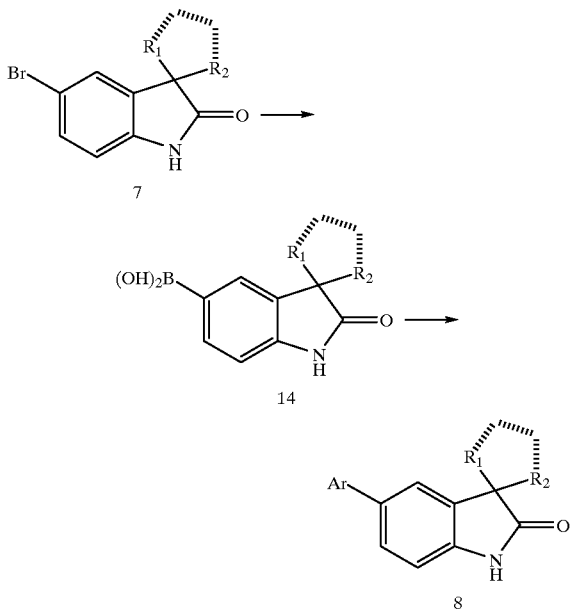

Treatment of the bromide 7 in an anhydrous solvent (e.g. THF, Et$_2$O) with a strong base (sodium hydride preferred, sodium hexamethyldisilazide, potassium hydride) followed by reaction at reduced temperature (−50 to −20° C.) with n-butyllithium and N,N,N',N'-tetramethylethylenediamine followed after a suitable period of time by a trialkylborate (trimethyl or triisopropylborate) gives after acidic work-up the boronic acid 14 (scheme 4). Compound 14 may then be reacted under palladium catalyzed conditions (tetrakis (triphenylphosphine)palladium(0), base (NaHCO$_3$, Na$_2$CO$_3$, K$_2$CO$_3$, triethylamine, CsF) solvent (toluene/EtOH/water, THF/water, dimethoxyethane/water, anhydrous dimethoxyethane) with an aryl bromide, aryl iodide, aryltrifluoromethane sulfonate of aryl fluorosulfonate, to provide the desired compounds 8.

An alternative strategy would be to prepare an organo zinc or magnesium reagent from compound 7 and react it in-situ with an aryl bromide, aryl iodide, aryltrifluoromethane sulfonate of arylfluorosulfonate, under palladium catalyzed conditions to afford compound 8. Such an organo zinc or magnesium species could be prepared by treatment of the bromide 7 in an anhydrous solvent (e.g. THF, Et$_2$O) with a strong base (sodium hydride preferred, sodium hexamethyldisilazide, potassium hydride) followed by reaction at reduced temperature (−50 to −20° C.) with n-butyllithium and N,N,N',N'-tetramethylethylenediamine followed after a suitable period of time by reaction with anhydrous zinc chloride or magnesium bromide.

The compounds of the present invention can be used in the form of salts derived from pharmaceutically or physiologically acceptable acids or bases. These salts include, but are not limited to, the following salts with inorganic acids such as hydrochloric acid, sulfuric acid, nitric acid, phosphoric acid and, as the case may be, such organic acids as acetic acid, oxalic acid, succinic acid, and maleic acid. Other salts include salts with alkali metals or alkaline earth metals, such as sodium, potassium, calcium or magnesium in the form of esters, carbamates and other conventional "pro-drug" forms, which, when administered in such form, convert to the active moiety in vivo.

This invention includes pharmaceutical compositions and treatments which comprise administering to a mammal a pharmaceutically effective amount of one or more compounds as described above as antagonists of the progesterone receptor.

The progesterone receptor antagonists of this invention, used alone or in combination, can be utilized in methods of contraception and the treatment and/or prevention of benign and malignant neoplastic disease. Specific uses of the compounds and pharmaceutical compositions of invention include the treatment and/or prevention of uterine myometrial fibroids, endometriosis, benign prostatic hypertrophy; carcinomas and adenocarcinomas of the endometrium, ovary, breast, colon, prostate, pituitary, meningioma and other hormone-dependent tumors. Additional uses of the present progesterone receptor antagonists include the synchronization of the estrus in livestock.

When the compounds are employed for the above utilities, they may be combined with one or more pharmaceutically acceptable carriers or excipients, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 500 mg/kg of animal body weight, preferably given in divided doses two to four times a day, or in a sustained release form. For most large mammals, the total daily dosage is from about 1 to 100 mg, preferably from about 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvents customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringe ability exits. It must be stable under conditions of manufacture and storage and must be preserved against the contaminating action of microorganisms such as bacterial and fungi. The carrier can be a solvent or dispersion medium containing, for example, water, ethanol (e.g., glycerol, propylene glycol and liquid polyethylene glycol), suitable mixtures thereof, and vegetable oil.

The present invention may be further understood by the following non-limiting examples.

EXAMPLE 1

5-(3-Nitro-phenyl)-1,3-dihydro-indol-2-one
5-(Bromo)-1,3-dihydro-indol-2-one

A solution of oxindole (2.0 g, 15.0 mmol) and sodium acetate (2.1 g, 25.5 mmol) in $CHCl_3$ (20 $cm^3$) was treated with bromine (2.4 g, 15.0 mmol) in $CHCl_3$ (10 $cm^3$). After 30 min. the mixture was allowed to warm to RT and stirred for 1 h. The reaction mixture was diluted with EtOAc (500 $cm^3$) and poured into water. The aqueous layer was extracted with EtOAc (×2), the combined organic layers were washed with water, sat. sodium hydrogen carbonate solution, brine, dried ($MgSO_4$), and evaporated to give the title compound (3.1 g, 14.6 mmol, 96 %) as an off-white solid which was used without further purification: mp. 221–223° C.; $^1$H NMR (DMSO-$d_6$) δ3.51 (s, 2H), 6.76 (d, 1H, J=8.1 Hz), 7.33(dd, 1H, J=8.1, 1.7 Hz), 7.37 (s, 1H), 10.49 (br s, 1H); $^{13}$C NMR (DMSO-$d_6$) δ36.10 (t), 111.21 (d), 113.16 (s), 127.54 (d), 128.3 (s), 130.40 (d), 143.34 (s), 176.24 (s); MS (EI) m/z 211, 213 $(M)^+$.

5-bromo-2-indolinone (1.08 g, 5.09 mmol) and tetrakistriphenyl phosphine Pd (0) (0.273 g) were stirred under an atmosphere of nitrogen in ethylene glycol dimethyl ether (35 mL). After 15 minutes, 3-nitrophenyl boronic acid (1.70 g, 10.2 mmol) was added, followed by potassium carbonate (4.24 g, 30.7 mmol) in water (15 mL). The reaction was heated to reflux overnight, cooled to room temperature and then filtered. Saturated ammonium chloride was added. The water layer was extracted with ethyl acetate (3×20 mnL). The combined organic layer was dried with $MgSO_4$, filtered, and solvent removed in vacuo. The product was purified by flash silica gel chromatography (3:2 hexane; ethyl acetate) to give 5-(3-Nitro-phenyl)-1,3-dihydro-indol -2-one (0.084 g, 65%), Mp=269° C.; $^1$H NMR (DMSO) δ10.5 (s, 1H), 8.38–8.36 (m:, 1H) 8.17–8.14 (m, 1H), 8.10–8.07 (m, 1H), 7.75–7.60 (m, 3H), 6.95 (d, 1H, J=8.1 Hz), 3.57 (s, 2H); IR (KBr) 3420, 3190, 1700 c/m$^-$; MS (EI) m/z 253 (M–H)$^-$; CHN calculated for $C_{14}H_{10}N_2O$: C, 66.14; H, 3.96; N, 11.02; Found: C, 64.59; H,4.16; N,9.43.

EXAMPLE 2

3-methyl-5-(3-nitrophenyl)-1,3-dihydroindol-2-one
5-bromo-3-methyl-indol-2-one

Under an atmosphere of nitrogen, bromine (0.96 g, 6.0 mmol) in acetic acid (5 $cm^3$) was added drop wise to a solution of 3-methyl-2-indolinone (0.8749 g, 6.0 mmol) (Kende, et al, Synth. Commun., 12, 1, 1982) and sodium acetate (0.50 g, 6.0 mmol) in acetic acid (10 $cm^3$). The reaction was stirred at room temperature for 3.5 h. Saturated sodium carbonate was added to quench the reaction. The water layer was extracted with EtOAc (×3), dried ($MgSO_4$), filtered, and evaporated to give the title compound (1.26 g, 93%), Mp=119–120° C.; $^1$H NMR (DMSO) δ1.32 (d, 3H, J=7.66 Hz), 3.45 (q, 1H, J=7.62 Hz), 6.77 (d, 1H, J=8.23 Hz), 7.46 (s, 1H), 7.36–7.33 (m, 1H), 10.4 (s, 1H); IR (KBr) 3200, 1725 cm$^{-1}$; MS (EI) m/z 224/226 (M–H)$^-$; CHN calculated for $C_9H_8BrNO$: C, 47.82; H, 3.57; N, 6.20; Found: C, 47.44; H, 3.42; N, 6.04.

5-Bromo-3-methyl-1,3-dihydro-indol-2-one (0.50 g, 2.22 mmol) and tetrakis(triphenylphosphine)palladium(0) (0.15 g) were stirred under an atmosphere of nitrogen in dimethoxyethane (18 $cm^3$). After 15 min., 3-nitrophenyl boronic acid (0.74 g, 4.45 mmol) was added, followed by potassium carbonate (1.86 g, 13.5 mmol) in water (7 $cm^3$). The reaction was heated to reflux for 8 h and then stirred at room temperature overnight. Saturated ammonium chloride was added; and the aqueous layer was extracted with EtOAc (×3). The combined organic layers were dried ($MgSO_4$), filtered, and evaporated. The residue was purified by column chromatography ($SiO_2$, EtOAc:hexane 1:2); eluted: 2:1 hexane; ethyl acetate, to give the title compound (0.30 g, 47 %), mp 200–203° C.; $^1$ H NMR (DMSO-$d_6$) δ1.41 (d, 3 H, J=7.61 Hz), 3.50 (q, 1H, J=7.60 Hz), 6.96 (d, 1H, J=8.08 Hz), 7.62 (d, 1H, J=8.06 Hz), 7.75–7.70 (m, 2H), 8.18–8.10 (m, 2H), 8.41–8.39 (m, 1H), 10.5 (s, 1H); IR (KBr) 3450, 1700 cm$^{-1}$; MS (EI) m/z 267 (M–H); Anal. Calc. for $C_{15}H_{12}N_2O_3+0.2C_4H_8O_2$: C, 66.61; H, 4.46; N, 9.83; Found: C, 66.26; H, 4.59; N, 10.06.

EXAMPLE 3

5-(3-Methoxy-phenyl)-3,3-dimethyl-13-dihydro-indol-2-one
5-bromo-1,3-dihydro-3,3-dimethyl-2H-indol-2-one 3,3-dimethyl-indol-2-one (0.65 g, 4.03 mmol) and sodium acetate (0.33 g, 4.07 mmol) were stirred in acetic acid (5 $cm^3$) then bromine (0.66 g, 4.13 mmol) in acetic acid (5 $cm^3$) was added drop-wise to the reaction mixture. The reaction was stirred for 50 min., and then poured into water. The mixture was basified with sodium carbonate and then extracted with ethyl acetate (×3), dried ($MgSO_4$), filtered, and evaporated to the title compound (0.89 g, 92%) $^1$H NMR (DMSO-$d_6$) δ1.21 (s, 6H), 6.76 (d, 1H, J=8.22 Hz), 7.29 (dd, 1H, J=2.12 Hz, 8.23 Hz), 7.49 (d, 1H, J=2.03 Hz), 10.4 (s, 1H).

5-bromo-1,3-dihydro-3,3-dimethyl-2H-indol-2-one (0.33 g, 1.38 mmol) and tetrakis(triphenylphosphine)palladium(0) (0.094 g) were stirred under an atmosphere of nitrogen in dimethoxyethane (12 $cm^3$). After 15 minutes, 3-methoxyphenylboronic acid (0.42 g, 2.76 mmol) was added, followed by potassium carbonate (1.15 g, 8.34 mmol) in water (5 $cm^3$). The reaction was heated to reflux for 5 hours, and then cooled to room temperature. Saturated aqueous ammonium chloride and EtOAc were added and the mixture was filtered. The aqueous layer was extracted with EtOAc (×2), and the combined organic layers were dried (MgSO$_4$), filtered, and evaporated. The residue was purified by column chromatography (SiO$_2$, EtOAc:hexane 1:3) to afford the title compound (0.11 g, 31%), mp=157–158° C.; $^1$H NMR (DMSO-d$_6$) δ3.34 (s, 6H), 3.82 (s, 3H), 6.87–6.93 (m, 2H), 7.20–7.15 (m, 2 H), 7.37–7.32 (m, 1H), 7.49–7.46 (m, 1H), 7.63 (d, 1H, J=1.14 Hz), 10.4 (s, 1H); MS (EI) m/z 266 (M−H)$^−$; Anal. Calc. for C$_{17}$H$_{17}$NO$_2$: C, 76.38; H, 6.41; N, 5.24; Found: C, 76.02; H, 6.49; N, 5.02.

EXAMPLE 4

5-(3-Chloro-phenyl)-3,3-dimethyl-1,3dihydro-indol-2-one 5-bromo-1,3-dihydro-3,3-dimethyl-2H-indol-2-one (0.98 g, 4.07 mol) and tetrakis(triphenylphosphine)palladium(0) (0.239 g) were stirred under an atmosphere of nitrogen in dimethoxyethane (35 cm$^3$). After 15 min., 3-chlorophenylboronic acid (1.27 g, 8.13 mol) was added, followed by potassium carbonate (3.40 g, 45 mmol) in water (15 cm$^3$). The reaction was heated to reflux for 2 hours and then stirred at room temperature overnight. The mixture was diluted with sat. ammonium chloride and extracted with EtOAc (×3). The combined organic layers were dried (MgSO$_4$), filtered, and evaporated. The residue was purified by column chromatography (SiO$_2$, EtOAc:hexane, 1:3) to afford the title compound (0.284 g, 25%): mp 188–189° C.,; $^1$H NMR (DMSO-d$_6$) δ3.34 (s, 6H), 6.93 (d, 1H, J=8.04 Hz), 7.38–7.35 (m, 1H), 7.53–7.43 (m, 2H), 7.61 (d, 1H, J=7.68 Hz), 7.70 (s, 2H), 10.40 (s, 1H); IR (KBr) 3420, 3150, 3050, 1700 cm$^{-1}$; MS (EI) m/z 270 (M−H)$^−$; Anal. Calc. for C$_{16}$H$_{14}$ClNO+0.1C$_4$H$_8$O$_2$: C, 70.21; H, 5.32; N, 4.99; Found: C, 70.3; H, 5.44; N, 4.93.

EXAMPLE 5

3,3-Dimethyl-5-(3-nitro-phenyl)-1,3-dihydro-indol-2-one 5-bromo-1,3-dihydro-3,3-dimethyl-2H-indol-2-one (1.02 g, 4.26 mmol) and tetrakis(triphenylphosphine)palladium(0) (0.244 g) were stirred under an atmosphere of nitrogen in dimethoxyethane (35 cm$^3$). After 15 minutes, 3-nitrophenylboronic acid (1.43 g, 2.56 mmol) was added, followed by potassium carbonate (3.54 g, 2.56 mmol) in water (15 cm$^3$). The reaction was heated to reflux for 2 hours and then stirred at room temperature overnight. Saturated ammonium chloride and EtOAc were added and the mixture was filtered. The aqueous layer was extracted with ethyl acetate (×2), and then the combined organic layers were dried (Na$_2$SO$_4$), filtered, and evaporated. The residue was purified by column chromatography (SiO$_2$, EtOAc:hexane, gradient elution) to afford the title compound (0.86 g, 67%) mp 234–235° C.; $^1$H NMR (DMSO-d$_6$) δ3.33 (s, 6H), 6.98 (d, 1H, J=8.06 Hz), 7.61 (dd, 1H, J=1.85, 8.03 Hz), 7.73 (t, 1H, J=7.98 Hz), 7.81 (d, 1H, J=1.63 Hz), 8.11–8.18 (m, 2H), 8.42–8.43 (m, 1H), 10.5 (s, 1H); MS (EI) m/z 281; Anal. Calc. for C$_{16}$H$_{14}$N$_2$O$_3$.0.2H$_2$O: C, 67.51; H, 4.92; N, 9.37; Found: C, 67.48; H, 5.17; N, 9.48.

EXAMPLE 6

5-(3-Chloro-phenyl)-3-ethyl-1,3dihydro-indol-2-one 3-Ethyl-indol-2-one

A solution of oxindole (40 g, 0.3 mol) in dry THF (400 ml) under N$_2$ was cooled to −25° C. and treated drop wise with n-butyl lithium (2.5M in hexanes, 240 ml, 0.6 mol). To the resulting solution was added N,N,N',N'-tetramethylethylenediamine (90.4 ml, 0.6 mol). After 30 min. iodoethane (48 ml, 0.6 mol) was added and the reaction mixture was allowed to warm to RT and stirred over night. The reaction mixture was poured into aqueous NH$_4$Cl solution, extracted with EtOAc (2×) and the combined organic layers were washed with dil. HCl, water, brine, dried (MgSO$_4$) and concentrated. The residual oil was triturated with hexane to afford the crude product (24.5 g, 51%). A sample (3 g) was recrystallized from EtOAc/hexane to obtain the title compound (1.4 g), mp. 100–101° C.; $^1$H-NMR (DMSO-d$_6$) δ0.76 (t, 3H, J=7.5 Hz), 1.8–2.0 (m, 2H), 3.38 (t, 3H, J=5.7 Hz), 6.8 (dt, 11H, J=7.69, 0.45 Hz), 6.93 (dt, 1H, J=7.45, 1.10 Hz), 7.15 (m, 1H), 7.22 (m, 1H), 10.3 (s, 1H); MS (ESI) m/z 270 [M+H].

5-Bromo-3-ethyloxindole

A solution of 3-ethyloxindole (6.0 g, 40 mmol) and sodium acetate (4 g, 48 mmol) in acetic acid (100 ml) was treated with bromine (6.4 g, 40 mmol). After 30 min. the mixture was diluted with water and extracted with EtOAc (2×); the combined organic layers were washed with water, sat. sodium hydrogen carbonate solution, and brine, dried (MgSO$_4$) and evaporated to afford the crude product (9.2 g, 96%). A sample was recrystallized from EtOAc/hexane to obtain the subtitled compound, mp. 130–132° C.; $^1$H-NMR (DMSO-d$_6$) δ0.74 (t, 3H, J=7.5 Hz), 1.8–2.0 (m, 2H), 3.45 (t, 1H, J=5.5 Hz,), 6.76 (d, 1H, J=8.35 Hz), 7.42 (m, 1H), 10.43 (s, 1H; MS (−ESI) m/z 238/240 (M−H).

A solution of 5-bromo-3-ethyl-oxindole (3.5 g, 14.6 mmol), 3-chlorophenylboronic acid (2.4 g, 15 mmol), potassium carbonate (4.5 g, 33 mmol) and tetrakis(triphenylphosphine)palladium(0) (0.87 g, 0.75 mmol) in dimethoxyethane (160 ml), ethanol (40 ml), and water (40 ml) was heated to reflux to 6 hours. After cooling to RT, the mixture was diluted with water and extracted with EtOAc (3×). The combined organic extracts were washed with water, then brine, dried (MgSO$_4$) and evaporated. The residue was purified by column chromatography (SiO$_2$, EtOAc:hexane 1:3) to afford the title compound (0.46 g, 12%), mp. 118–120° C.; $^1$H-NMR (DMSO-d$_6$) δ0.78 (t, 3H, J=7.25 Hz) 1.8–2.02 (m, 2H), 3.47 (t, 1H, J=5.71 Hz), 6.89 (d, 3H, J=8.1 Hz), 7.35 (n, 1H), 7.44 (t, 1H, J=7.91 Hz), 7.51 (m, 1H), 7.58 (m, 2H), 7.67 (t, 1H, J=1.76 Hz), 10.5 (s, 1H); MS (−ESI) m/z 270 (M−H).

EXAMPLE 7

5-(3-Chloro-phenyl)-3,3-diethyl-1,3-dihydro-indol-2-one

A solution of 3-ethylindol-2-one (16 g, 0.1 mol) in dry THF (200 ml) under N$_2$ was cooled to −25° C. and treated drop wise with n-butyllithium (2.5M in hexanes, 80 ml, 0.2 mol). To the resulting solution was added N,N,N',N'-tetramethylethylenediamine (30 ml, 0.2 mol). After 30 iodoethane (8 ml, 0.1 mol) was added and the reaction mixture was allowed to warm to RT and stirred over night. The reaction mixture was poured into an aqueous NH$_4$Cl solution, extracted with EtOAc (2×) and the combined organic layers were washed with dil. HCl, water, brine, dried (MgSO$_4$) and concentrated. The residual oil was triturated with hexane to afford the title product (9 g, 45%), mp. 156–159° C.; $^1$H NMR (DMSO-d$_6$) δ10.44 (s,1H), 7.70–7.69 (t,1H), 7.62–7.59 (m, 1H), 7.58 (d,1H J=1.7Hz), 7.53–7.50 (m, 1H), 7.45–7.41 (t,1H), 7.36–7.35 (m,1H), 7.34–7.33 (m,1H), 6.91–6.89 (d,1H, J=8.2 Hz), 1.87–1.80 (m,2H), 1.77–1.70 (m, 2H), 0.54–0.50 (t, 6H); MS (+ESI) m/z 190 (M+H).

5-Bromo-1,3-dihydro-3,3-diethyl-[2H]-indol-2-one

A solution of 3,3-diethylindol-2-one (8 g, 40 mmol) and sodium acetate (4 g, 48 mmol) in acetic acid (100 ml) was treated with bromine (6.4 g, 40 mmol). After 30 min. the mixture was diluted with water and extracted with EtOAc (2×); the combined organic layers were washed with water, sat. sodium hydrogen carbonate solution, then brine, dried (MgSO$_4$) and evaporated to afford the crude product (7.6 g, 75%). A sample was recrystallized from EtOAc/hexane to obtain the subtitled compound, m.p. 164–165° C.; $^1$H-NMR (DMSO-d$_6$) δ10.45 (s, 1H), 7.41–7.40(d, 1H, J=2.2Hz), 7.34–7.31 (m, 1H), 6.78–6.76 (d, 1H J=8.2 Hz), 1.78–1.65 (m, 4H), 0.50–0.46 (m, 6H); MS (-ESI) m/z 266/268 (M–H).

A solution of 5-bromo-1,3-dihydro-3,3-diethyl-[2H]-indol-2-one (2.7 g, 10 mmol), 3-chlorophenylboronic acid (1.6 g, 10 mmol), potassium carbonate (4 g, 30 mmol) and tetrakis(triphenylphosphine)palladium(0) (0.5 g, 0.4 mmol) in dimethoxyethane (100 ml), ethanol (25 ml), and water (25 ml) was heated to reflux for 6 hours. After cooling to RT, the mixture was diluted with water and extracted with EtOAc (2×). The combined organic extracts were washed with water, then brine, dried (MgSO$_4$) and evaporated. The residue was purified by column chromatography (SiO$_2$, EtOAc:hexane 1:3) to afford the title compound (0.8 g, 27%), mp. 195–197° C.; $^1$H-NMR (DMSO-d$_6$) δ7.70 (t, 1H, J=2 Hz), 7.62–7.60 (m, 1H), 7.58 (d, 1H), J=1.7 Hz), 7.52, (dd, 1H, J=8.1, 2 Hz), 7.43 (t, 1H, 7.9 Hz), 7.36–7.33 (m, 1H), 6.90 (d, 1H, J=8.1 Hz), 1.87–1.70 (m, 4H) and 0.52 (t, 6H, J=7.4 Hz); MS (+APCI) m/z 300/302 (M–H).

EXAMPLE 8

5-(3-Chloro-phenyl)-3-methoxy-3-methyl-1,3-dihydro-indol-2-one

A solution of 5-bromoisatin (5.0 g, 22 mmol) in dry THF (50 cm$^3$) under N$_2$ was cooled to 0° C. and treated drop-wise with methyl magnesium bromide (3M in diethylether, 14.7 cm$^3$, 44 mmol) and the mixture was allowed to warm up-to room temperature. The reaction was poured into sat. ammonium chloride solution, then extracted into EtOAc (×3). The combined organic layers were then washed with water, brine, dried (MgSO$_4$) and evaporated. The residue was then purified by column chromatography (SiO$_2$, EtOAc:hexane, gradient elution) to afford 5-bromo-3-hydroxy-3-methyl-1, 3-dihydro-indol-2-one (1.53 g, 6.32 mmol, 29%): $^1$H NMR (DMSO-d$_6$) δ1.38 (s, 3H), 5.99 (s, 1H), 6.77 (d, 1H, J=1.7 Hz), 7.38 (s, 1H, br); MS ((−) ESI) m/z 240/242 (M)$^-$.

5-bromo-3-hydroxy-3-methyl-1,3-dihydro-indol-2-one (1.0 g, 4.1 mmol) was dissolved in dry DMF (15 cm$^3$) cooled to 0° C. and treated with potassium tert-butoxide (1M in THF, 4.5 cm$^3$, 4.5 mmol). After 15 min. methyl-p-toluenesulfonate (0.93 g, 5 mmol) was added and the mixture was allowed to warm up-to room temperature. After 2 h the mixture was poured into saturated ammonium chloride solution and extracted with EtOAc (×2), then the combined organic layers were washed with water, sodium hydroxide (1N, ×2), water (×3), dried (MgSO$_4$) and evaporated. The residue was then purified by column chromatography (SiO$_2$, EtOAc: hexane, gradient elution) to afford 5-bromo-3-methoxy-3-methyl-1,3-dihydro-indol-2-one (0.56 g, 2.2 mmol, 53%): $^1$H NMR (CDCl$_3$) δ1.59 (s, 3H), 3.18 (s, 3H), 6.73 (d, 1H, J=8.2 Hz), 7.45 (dd, 1H, J=8.2, 2 Hz), 7.52 (d, 1H, J=2 Hz); MS (EI) m/z 225 (M)$^+$.

A solution of 5-bromo-3-methoxy-3-methyl-1,3-dihydro-indol-2-one (0.52 g, 2.0 mmol) and tetrakis (triphenylphosphine)palladium(0) (0.12 g, 0.1 mmol) was dissolved in dimethoxyethane (22 cm$^3$). After 15 min., 3-chlorophenylboronic acid (0.63 g, 4.1 mmol) and sodium carbonate (1.0 g) in water (10 cm$^3$) was added and the reaction was heated under reflux. After 2 h the mixture was cooled, poured into water and extracted with EtOAc (×2), the combined organic extracts were washed with sodium hydroxide solution (1N, ×2) water, brine, dried (MgSO$_4$) and evaporated. The residue was then purified by column chromatography (SiO$_2$, EtOAc:hexane, 5:1) to afford 5-(3-chloro-phenyl)-3-methoxy-3-methyl-1,3-dihydro-indol-2-one (0.17 g, 0.58 mmol, 29%): $^1$H NMR (CDCl$_3$) δ1.65 (s, 3H), 2.91 (s, 1H), 3.24 (s, 3H), 6.92 (d, 1H, J=8.1 Hz), 7.26–7.38 (m, 2H), 7.43–7.46 (m, 1H), 7.52–7.55 (m, 1H), 7.62 (d, 1H, J=1.8 Hz); MS ((+) APCI) m/z 288 (M +H)$^+$.

EXAMPLE 9

5-(3-Chloro-phenyl)-3-methoxy-3-prop-1-ynyl-1,3-dihydro-indol-2-one

To a solution of 5-bromoisatin (2.5 g, 11 mmol) in dry THF (100 cm$^3$) at −10° C. under a nitrogen atmosphere was added 1-propynylmagnesium bromide (0.5 M in THF, 47 cm$^3$, 23.5 mmol). After 1 h, the mixture was poured into saturated ammonium chloride and extracted with EtOAc (×3), washed with brine, dried (MgSO$_4$) and evaporated to afford 5-bromo-3-hydroxy-3-prop-1-ynyl-1,3-dihydroindol-2-one (2.83 g, 10.6 mmol, 97%) which was used without further purification: (CDCl$_3$) δ1.83 (s, 3H), 6.79 (d, 1H, J=8.0 Hz), 6.90 (s, 1H), 7.41–7.44 (m, 2H), 10.59 (s, 1H); MS ((−) ESI) m/z 264 (M–H)$^-$.

To a solution of 5-bromo-3-hydroxy-3-prop-1-ynyl-1,3-dihydroindol-2-one (1.0 g, 3.75 mmol) in dry DMF (15 cm$^3$) at 0° C., was added potassium tert-butoxide (1M in THF, 4.1 cm$^3$, 4.1 mmol). After 15 min. methyl p-toluenesulfonate (0.85 g, 4.6 mmol) was added and the mixture was allowed to warm up to room temperature. After 16 h the mixture was poured into saturated ammonium chloride, extracted with EtOAc (×3), washed with water, brine, dried (MgSO$_4$) and evaporated. The residue was purified by column chromatography (SiO$_2$, EtOAc:hexane 1:3) to afford 5-bromo-3-methoxy-3-prop-1-ynyl-1,3-dihydroindol-2-one (0.62 g, 2.21 mmol, 59%): (CDCl$_3$) δ inter alia 1.87 (s, 3H), 3.19 (s, 3H), 3.35 (s, 1H), 6.72 (d, 1H, J=8.3 Hz), 7.48 (dd, 1H, J=8.3, 2Hz), 7.63 (d, 1H, J=2Hz): MS (EI) m/z 279 (M)$^+$.

5-bromo-3-methoxy-3-prop-1-ynyl-1,3-dihydroindol-2-one (0.56 g, 2.0 mmol) and tetrakis(triphenylphosphine) palladium(0) (0.12 g, 0.10 mmol ) were stirred at room temperature in dimethoxyethane (22 cm$^3$). After 15 min. 3-chlorophenylboronic acid (0.63 g, 4.0 mmol) and sodium carbonate (1.06 g, 10 mmol) in water (11 cm$^3$) were added and the mixture heated under reflux. After 16 h, the mixture was cooled, poured into water and extracted with EtOAc (×3). The combined organic layers were washed with sodium hydroxide (1N, ×2), brine, dried (MgSO$_4$) and evaporated. The residue was subjected to column chromatography (SiO$_2$, EtOAc:hexane, gradient elution) and the product triturated with hexane to afford the title compound (0.095 g, 0.30 mmol, 15%) as a solid: mp.>190° C. (decomp.); (CDCl$_3$) δ1.88 (s, 3H), 3.25 (s, 3H), 3.30 (s, 1H), 6.91 (d, 1H, J=8.1 Hz), 7.29–7.39 (m, 2H), 7.44–7.47 (m, 1H), 7.54–7.57 (m, 2H), 7.74 (d, 1H, J=1.7 Hz); MS (EI) m/z 311 (M+).

EXAMPLE 10

5-(3-Chloro-phenyl)-1,3-dihydro-indol-2-one

A solution of the 5-bromoxindole (0.5 g, 2.4 mmol) and tetrakis(triphenylphosphine) palladium (0.14 g, 0.12 mmol) in dimethoxyethane (10 cm$^3$) was stirred under N$_2$ for 20 min. To this mixture was then added 3-chlorophenylboronic acid (0.44 g, 2.83 mmol) and sodium carbonate (0.75 g, 7.1 mmol) in water (4 cm$^3$). The solution was brought to reflux for 6 h then cooled to RT, poured into water and extracted with EtOAc (×3). The combined organic extracts were washed with water, brine, dried (MgSO$_4$), and evaporated. The residue was purified by column chromatography (SiO$_2$, ethyl acetate: hexane 1:3) to afford the title compound (0.49 g, 2.0 mmol, 86%) as a tan solid: mp. 169–171° C., $^1$H NMR (THF-d$_8$) δ3.45 (s, 2H), 6.85 (d, 1H J=8.1 Hz), 7.25 (d, J=8.0 Hz, 1H), 7.35 (dd, 7.8 Hz, 1H), 7.43 (d, J=8.1 Hz, 1H), 7.49 (d, J=7.8 Hz, 1H), 7.50 (s, 1H), 7.59 (dd, J=1.78, 1.78 Hz, 1H), 9.5 (br s, 1H); $^{13}$C NMR (THF-d$_8$) δ36.39 (t), 109.80, 123.97, 125.55, 127.19 (d), 127.68 (s), 130.89 (d), 133.73, 135.29, 144.23, 145.09, 176.45 (s); MS (EI) m/z 243, 245 (M)$^+$; Anal. (C$_{14}$H$_{10}$ClNO) C, H, N.

EXAMPLE 11

5'-(3-Chlorophenyl)spiro[1,3-dioxolane-2,3'-[3H]indol]-2'(1'H)-one

5-[3-Chloro-phenyl]-1H-indole-2,3-dione

A solution of 5-(3-Chloro-phenyl)-1,3-dihydro-indol-2-one (10.0 g, 41 mmol) in dioxane (200 cm$^3$) and SeO$_2$ (22.8 g, 205 mmol) was brought to reflux for 2 h then cooled to RT and concentrated onto Florisil. The Florisil was washed (acetone:CHCl$_3$ 1:9) and the combined organic extracts were evaporated. The residue was purified by column chromatography (SiO$_2$, acetone:CHCl$_3$ 1:8) to afford the subtitled compound (8 g, 31 mmol, 76%) as a tan solid: m.p. 256–258° C., $^1$H NMR (THF-d$_8$) δ6.96 (d, J=8.8 Hz, 1H), 7.33 (d, J=8.1 Hz, 1H), 7.4 (dd, J=7.7, 7.7 Hz, 1H), 7.56 (d, J=7.7 Hz, 1H), 7.68 (dd, J=1.84, 1.84 Hz, 1H), 7.83–7.86 (m, 2H), 10.05 (br s, 1H); $^{13}$C NMR (DMSO-d$_6$) δ113.30 (d), 119.08 (s), 123.44, 125.57, 126.65, 127.92, 131.41 (d), 133.88, 134.47 (s), 137.25 (d), 141.51, 150.99, 160.15, 184.83 (s); MS (EI) m/z 256 (M–H)$^+$; Anal. (C$_{14}$H$_8$ClNO$_2$-0.1 H$_2$O) C, H, N.

A solution of the 5-[3-chloro-phenyl]-1H-indole-2,3-dione (0.5 g, 1.9 mmol) in toluene (30 cm$^3$) and ethylene glycol (1.1 cm$^3$, 19.4 mmol) and pTsOH (0.04 g, 0.2 mmol) was brought to reflux with azeotropic removal of water for 12 h then cooled to RT. The reaction mixture was diluted with EtOAc (100 cm$^3$) and washed with water, sat. sodium hydrogen carbonate solution, brine, dried (MgSO$_4$), and evaporated to give an oily residue. The residue was purified by column chromatography (SiO$_2$, CH$_2$Cl$_2$) to afford the title compound (0.47 g, 1.6 mmol, 80%) as a tan solid: mp. 159–161° C.; $^1$H NMR (DMSO-d$_6$) δ4.29–4.39 (M, 4H), 6.93 (d, J=8.6 Hz, 1H), 7.4 (d, J=8.1 Hz, 1H), 7.46 (dd, J=7.9, 7.9 Hz, 1H), 7.7 (d, J=7.7 Hz, 1H), 7.68–7.71 (m, 3H), 10.55 (s, 1H); $^{13}$C NMR (DMSO-d$_6$) δ65.53 (t), 110.89, 123.25, 124.81 (d), 125.65 (s), 125.83, 126.79, 130.09, 130.61 (d), 132.96, 133.64, 141.53, 14267, 174.36 (s); MS (EI) m/z 301/303 (M)$^+$; Anal. (C$_{16}$H$_{12}$ClNO$_3$) C, H, N.

EXAMPLE 12

5'-(3-Chlorophenyl)spiro[1,3-dioxane-2,3-[3H]indol]-2'(1'H)-one

The title compound was prepared according to the procedure for example 11: m.p. 242–244° C.; $^1$H NMR (DMSO-d$_6$) δ1.7 (M, 1H), 2.2 (M, 1H), 3.95 (m, 2H), 4.78 (t, 2H), 6.9 (d, J=7.9 Hz, 1H), 7.39 (d, J=7.9 Hz, 1H), 7.46 (dd, J=7.9, 7.9 Hz, 1H), 7.59–7.68 (m, 3H), 10.59 (br s, 1H); $^{13}$C NMR (DMSO-d$_6$) δ25.19, 60.68 (t), 93.58 (s), 110.94, 122.93, 125.29, 126.29, 127.19 (d), 128.65 (s), 129.92, 131.07 (d), 133.16, 134.08, 141.61, 142.15, 173.29 (s); MS (EI) m/z 315/317 (M)$^+$; Anal. (C$_{17}$H$_{14}$ClNO$_3$) C, H, N.

EXAMPLE 13

5'-(3-nitrophenyl)spiro[cyclopentane-1,3'-[3H]indol]2'(1'H)-one Spiro[cyclopentane-1,3'-[3H]indol]-2'(1'H)-one To a −25° C. solution of oxindole (2.0 g, 15.0 mmol) in 40 (cm$^3$) of anhydrous THF under N$_2$ was added n-butyllithium (1.6 M in hexanes, 19.7 cm$^3$, 31.5 mmol) drop-wise. To the resulting milky solution was added N,N,N',N'-tetramethylethylenediamine (4.75 cm$^3$, 31.5 mmol). After 30 min. a solution of 1,4-diiodobutane (21.9 g, 70.6 mmol) in THF (3 cm$^3$) was added and the reaction mixture was allowed to warm to RT and stirred for 14 h. The reaction mixture was poured into water, extracted with EtOAc (×2), then the combined organic layers were washed with dil. HCl (pH 1), water (×2), dried (MgSO$_4$) and evaporated. The residue was purified by column chromatography (SiO$_2$, EtOAc:hexane 1:4) to afford the subtitled compound (1.4 g, 7.5 mmol, 50%) as a tan solid: $^1$H NMR (CDCl$_3$) δ1.8–2.2 (m, 8H), 6.94 (dd, J=7.5, 1.0 Hz, 1H), 7.01 (dd, J7.5, 1.0 Hz, 1H), 7.14–7.25 (m, 2H), 9.30 (br s, 1H).

5-Bromo-spiro[cyclopentane-1,3'-[3H]indol]-2'(1'H)-one A solution of spiro[cyclopentane-1,3'-[3H]indol]-2'(1'H)-one (0.27 g, 1.4 mmol) and sodium acetate (0.12 g, 1.46 mmol) in acetic acid (10 cm$^3$) was treated with bromine (0.24 g, 1.51 mmol) in acetic acid (2 cm$^3$). After 30 min. the mixture was poured into sat. sodium hydrogen carbonate solution and extracted with EtOAc (×2), the combined organic layers were washed with water, sat. sodium hydrogen carbonate solution, water, dried (MgSO$_4$), and evaporated to give the subtitled compound (0.37 g, 1.47 mmol, 96%) as an off-white solid which was used without further purification: $^1$H NMR (CDCl$_3$) δ1.8–2.27 (r, 8H), 6.79 (d, J=8 Hz, 1H), 7.30–7.39 (m, 2H), 8.63 (br s, 1H).

A solution of 5-bromo-spiro[cyclopentane-1,3'-[3H]indol]-2'(1'H)-one (0.3 g, 1.1 mmol) and tetrakis (triphenylphosphine)palladium(0) (0.07 g, 0.06 mmol) in dimethoxyethane (8 cm$^3$) was stirred under N$_2$ for 20 min. To this mixture was then added 3-nitrophenylboronic acid (0.23 g, 1.4 mmol) and sodium carbonate (0.36 g, 3.4 mmol) in water (3 cm$^3$). The solution was brought to reflux for 3 h then cooled to RT, poured into water and extracted with EtOAc (×3). The combined organic extracts were washed with water, brine, dried (MgSO$_4$), and evaporated. The residue was purified by column chromatography (SiO$_2$, ethyl acetate: hexane 1:3) to afford the title compound (0.21 g, 0.68 mmol, 62%) as a yellow solid: mp. 238–240 C.; $^1$H NMR (DMSO-d$_6$) δ1.89–1.99 (m, 8H), 6.96 (d, J=8.1 Hz, 1H), 7.58 (dd, J=8.1, 1.8 Hz, 1H), 7.66 (d, J=1.8 Hz, 1H), 7.71 (dd, J=8.0, 8.0 Hz, 1H), 8.13 (dd, J=7.0, 1.0 Hz, 2H), 8.4 (d, J=1.8 Hz, 1H), 10.42 ( br s, 1H); 13C NMR (dioxane-d$_8$) δ26.31, 38.13 (t), 53.85 (s), 108.9, 121.15, 121,33, 126.23, 129.38, 132.11 (d), 132.6, 138.32, 141.84, 142.74, 149.14, 182.68 (s); MS (EI) m/z 308 (M)$^+$.

EXAMPLE 14

3-(1',2'-Dihydro-2'-oxospiro[cyclohexane-1,3'-[3H]indol-5'-yl)benzaldehyde

Spiro[cyclohexane-1,3'-[3H]indol]-2'-(1'H)one

A solution of oxindole (25 g, 0.19 mol) in anhydrous tetrahydrofuran (800 cm$^3$) was cooled to −20° C., then n-butyllithium (2.5M in hexanes, 152 cm$^3$, 0.38 mol) was added slowly followed by N,N,N',N'-tetramethylethylenediamine (51 cm$^3$, 0.38 mol,). After 15 min. 1,5-diiodopentane (174 g, 0.54 mol) was added slowly and the mixture was allowed to warm to room temperature. After stirring for 16 h. saturated aqueous ammonium chloride solution (1L) and EtOAc (1L) were added. After 15 min. the layers were separated and the aqueous phase was extracted EtOAc (×2). The combined organic layers were extracted with hydrochloric acid (1N), then washed with brine (500 cm$^3$), dried (MgSO$_4$), and concentrated to obtain an oil. The oil was triturated with hexane (200 cm$^3$) and benzene (20 cm$^3$). The precipitate was collected and dried in vacuo to obtain the subtitled compound (26.3g, 69.6%) as colorless crystals: mp 110–114° C.; $^1$H NMR (DMSO-d$_6$) δ1.67 (m, 1H), 6.84 (d, 1H, J=8 Hz) 6.94 (t, 1H, J=8 Hz), 7.17 (t, 1H, J=8 Hz), 7.44 (d, 1H, J=8 Hz), 10.3 (s, 1H).

5'-Bromospiro[cyclohexane-1,3'-[3H]indol]-2'(1'H)-one

To a solution of spiro[cyclohexane-1,3'-[3H]indol]-2'(1'H)-one (17.6 g, 0.09 mol) in acetic acid (300 cm$^3$) was added sodium acetate (8.0 g, 0.1 mol) and bromine (14.6 g, 0.091 mmol) with stirring. After 30 min. at room temperature, the reaction mixture was partitioned between water and EtOAc. The aqueous phase was extracted twice with EtOAc. The combined organic layers were washed with water, dried (MgSO$_4$) and evaporated and the residue was triturated with hexane. The precipitate was collected, and dried in vacuo to obtain the subtitled compound (16.5g, 67%) as off-white crystals: mp 196–199° C.; $^1$H NMR (DMSO-d$_6$) δ1.62 (m, 10H), 6.8 (d, 1H, J=6.8 Hz), 7.36 (d, 1H, J=8.2, 1.8 Hz), 7.58 (dd, 1H, J=8.2, 1.8 Hz), 10.44 (s, 1H).

To a solution of 5'-bromospiro[cyclohexane-1,3'-[3H]indol]-2'(1'H)-one (1.00 g, 3.57 mmol) in dimethoxyethane (20 cm$^3$) was added tetrakis(triphenylphosphine)palladium (0.20 g, 0.17 mmol) under nitrogen. After 15 min. 3-formylphenylboronic acid (1.00 g, 6.93 g) was added followed by potassium carbonate (2.90 g, 21 mmol) in water (10 cm$^3$). After 20 h at reflux, the mixture was cooled, poured into water and extracted with EtOAc (×3). The combined organic extract was washed with sat. brine, dried (MgSO$_4$) and evaporated. The residue was purified by column chromatography (SiO$_2$, EtOAc:hexane, gradient elution) to afford the title compound (0.66 g, 2.15 mmol, 60%) as a white solid, 1H NMR (CDCl$_3$) δ1.65–1.85 (m, 6H), 1.86–2.08 (m, 4H), 7.22 (d, 1H, J=8 Hz), 7.48 (dd, 1H, J=8, 2 Hz), 7.61 (t, 1H, J=8 Hz), 7.66 (d, 1H, J=2 Hz), 7.81–7.88 ( m, 2H), 8.06 (t, 1H, J=2 Hz), 8.30 (s, 1H, br); MS ((+)ESI) m/z 306 (M +H)$^+$.

EXAMPLE 15

3-(1',2'-Dihydro-2'-oxospiro[cyclohexane-1,3'-[3H]indol-5'-yl)benzaldehyde oxime To a solution of 3-(1',2'-dihydro-2'-oxospirocyclohexane-1,3'-[3H]indol-5'-yl) benzaldehyde (0.59 g, 1.95 mmol) in EtOH: H$_2$O (10 cm$^3$,8:2) was added hydroxylamine hydrochloride (0.17 g, 2.5 mmol) and sodium acetate (0.20 g, 2.5 mmol). After 20 min. the mixture was concentrated, water was added, and extracted with EtOAc (×2). The combined organic layers were washed with sat. sodium hydrogen carbonate solution, water, sat. brine, dried (MgSO$_4$) and evaporated to afford the title oxime (0.63 g, 1.95 mmol, 100%) which was used without further purification, $^1$H NMR (CDCl$_3$) δ1.60–1.84 (m, 6H), 1.85–2.00 (m, 4H), 6.86 (d, 1H, J=8 Hz), 7.36 (dd, 1H, J=8, 2 Hz), 7.43–7.50 (m, 1H), 7.57–7.67 (m, 2H), 7.85 (s, 1H, br), 8.25 (s, 1H), 8.68 (s, 1H, br), 8.94 (s, 1H, br); MS ((-)ESI) m/z 319 (M–H)$^-$.

EXAMPLE 16

3-(1',2'-Dihydro-2'-oxospiro[cyclohexane-1,3'-[3H]indol-5'-yl)benzaldehyde methyloxime ether To a solution of 3-(1',2'-Dihydro-2'-oxospiro[cyclohexane-1,3'-[3H]indol-5'-yl)benzaldehyde (0.24 g, 0.79 mmol), and sodium acetate (0.083 g, 1.00 mmol) in EtOH:water (5 cm$^3$,8:2) was added methoxylamine hydrochloride (0.083 g, 1.00 mmol). After 30 min. the precipitate was isolated by filtration and washed with EtOH:water (8:2,×2), to afford the title compound (0.027 g, 0.08 mmol, 10%) as a white solid: mp 198–200 (decomp.): 1.58–2.07 (m, 10H), 4.00 (s, 3H), 6.98 (d, 1H, J=8 Hz), 7.42–7.49 (m, 2H), 7.53–7.58 (m, 2H), 7.64 (d, 1H, J=2 Hz), 7.75 (s, 1H), 8.07 (s, 1H, br), 8.15 (s, 1H); MS ((+)-ESI) m/z 335 (M +H)$^+$.

EXAMPLE 17

3-(1',2'-Dihydro-2'-oxosipiro[cyclohexane-1,3'-[3H]indol-5'-yl)pyridine carbonitrile A solution of 3-bromopyridine-5-carbonitrile (2.79 g, 15.26 mmol), hexamethylditin (5.00 g, 15.26 mmol) and tetrakis(triphenylphosphine)palladium(0) (0.20 g, 0.17 mmol) in anhydrous dimethoxyethane (30 cm$^3$) under N$_2$ was heated under reflux. After 16 h the mixture was concentrated and purified by column chromatography (SiO$_2$, EtOAc:hexane 5:95) to afford 3-cyanopyridine-5-trimethylstannane (2.82 g, 10.55 mmol, 69%): $^1$H NMR (CDCl$_3$) δ0.40 (s, 9H), 8.01 (m, 1H), 8.80 (m, 2H); MS ((+) APCI) m/z 269 (M +H)$^+$.

A solution of 5'-bromospiro[cyclohexane-1,3'-[3H]indol]-2'(1'H)-one (1.97 g, 7.05 mmol), 3-cyanopyridine-5-trimethylstannane (2.26 g, 8.46 mmol), bis(triphenylphosphine)palladium(II)chloride (0.33 g, 0.47 mmol) and lithium chloride (1.48 g, 35 mmol) in anhydrous toluene (30 cm$^3$) was heated under reflux. After 16 h the mixture was cooled, partitioned between EtOAc and water, the aqueous layer was re-extracted with EtOAc (×2), the combined organic extracts were washed with water, dried (MgSO$_4$) and evaporated. The residue was subjected to column chromatography (SiO$_2$, EtOAc:hexane, 1:2) and then further purified by preparative LC (Primesphere C18, 10 micron, 50×250 mm, MeCN: H$_2$O 1:1, 100 cm$_3$/min., RT 7.92 min.) to afford the title compound as white crystals (0.56 g, 1.84 mmol, 26%): mp. 232–234° C., $^1$H NMR (CDCl$_3$) δ1.68–1.89 (m, 6H), 1.93–2.13 (m, 4H), 7.12 (d, 1H, J=8 Hz), 7.49 (dd, 1H, J=8, 2 Hz), 7.66 (d, 1H, 2 Hz), 8.15 (t, 1H, J=2 Hz), 8.39 (s, 1H, br), 8.89 (d, 1H, J=2 Hz), 9.06 (d, 1H, J=2 Hz); MS ((+)-ESI) m/z 304 (M+H)$^+$.

EXAMPLE 18

5'-(Pyrimidin-5-yl)-spiro[cyclohexane]-1,3'-[3H]indol-2'(1H)-one

To a solution of 5'-bromospiro [cyclohexane-1,3'-[3H]indol]-2'-(1'H)-one (11 g, 0.04 mol) in dry tetrahydrofuran (200 cm$^3$) was added sodium hydride (60% dispersion in mineral oil, 1.6 g, 0.04 mol). After 30 min. stirring at room temperature, the mixture was cooled to −78° C. and butyl lithium (1.7M in hexanes, 23.2 cm$^3$,0.04 mol) was added slowly. After 30 min. di-iso-propylborate (25 cm$^3$,0.11 mol) was added and the mixture was allowed to warm to room temperature. After 2 hrs. hydrochloric acid (1N, 500 cm$^3$) and ethylacetate (500 cm$^3$) were added. The aqueous phase was extracted with ethylacetate, then the combined organic layers were washed with water, brine, dried (MgSO$_4$) and evaporated. The residue was triturated with hexane and the precipitate dried in vacuo to obtain (2'-oxo-2,3-dihydrospiro [cyclohexane-1,3'-[3H]indol]-5'-yl) boronic acid (8.3 g, 86%) as an off-white solid that was used without further purification. A sample that was further triturated with ethyl acetate had the following properties: mp. 255–260° C. dec.; $^1$H NMR (DMSO-d6) δ1.50 (m, 2H), 1.73 (m, 8H), 6.82 (d, 1H, J=7.72 Hz) 7.66 (d, 1H, J=7.72 Hz) 7.91 (s, 3H, br), 10.36 (s, 1H);MS ((−)ESI) m/z 244 [M−H].

A stirred mixture of 5-bromopyrimidine (3.2 g, 20 mmol) in toluene (20 cm$^3$), 2'-oxo-2,3-dihydrospiro[cyclohexane-1,3'-[3H]indol]-5'yl) boronic acid (0.49 g, 2.2 mmol) in ethanol (10 cm$^3$), potassium carbonate (0.28 g, 2.0 mmol) in water (10 cm$^3$) and tetrakis (triphenylphosphine)palladium (0) (0.15 g, 0.13 mol) was heated overnight under reflux and in an atmosphere of nitrogen. The reaction mixture was treated with 20 mL of sodium bicarbonate solution and was then extracted with ethyl acetate (2×50 mL). The combined organic phases were washed with saturated brine, dried (MgSO$_4$). Recrystallization from ethanol gave 0.13 g of pure product, mp 227–228° C. IR (KBr) 1700 cm−1 $^1$H-NMR (DMSO-d$_6$) δ10.48 (s, 1H), 9.13 (s,1H), 9.11 (s,2H), 7.86 (s, 1H) 7.63 (dd, 1H;J=1.5 Hz and 8.1 Hz), 6.98 (d, 1H, J=8.1 Hz), 6.98 (d, 1H, J=8.1) 1.75 (m, 10); MS (ESI) m/z 278 (M−H).

EXAMPLE 19

5-(3-chlorophenyl)spiro cyclohexane-1,3-[3H]indol]-2(1H)-one

Prepared according to the procedure for example 14: mp. 164–165° C., $^1$H NMR (CDCl$_3$) δ1.60–1.78 (m, 6H), 1.81–1.99 (m, 4H), 7.04 (d, J=8.1 Hz, 1H), 7.22–7.47 (m, 4H), 7.53 (s, 1H), 7.61 (s, 1H), 9.28 (br s, 1H); $^{13}$C-NMR (CDCl$_3$) δ20.17, 24.12, 31.92 (t), 47.22 (s), 109.21, 121.94, 124.06, 125.50, 125.79, 125.97, 126.38, 128.96 (d), 132.88, 133.59, 135.60, 139.14, 142.17, 182.89 (s); MS (EI) m/z 310, 312 (M−H)$^+$.

EXAMPLE 20

5'-(3Chloro-4-fluorophenyl)spiro[cyclohexane-1,3'-[3H]indol]-2'(1'H)-one

Prepared according to the procedure for example 18: mp 188–189° C.; $^1$H-NMR (CDCl$_3$) δ7.97 (s, 1H), 7.57–7.54 (m, 2H), 7.41–7.34 (m, 2H), 7.20 (t, 1H, J=8.7 Hz), 9.96 (d, 1H, J=8.1 Hz), 2.04–1.65 (m, 10H); MS ((+)APCI) m/z 330 [M+H]$^+$.

EXAMPLE 21

5'-(3-Fluorophenyl)spiro[cyclohexane-1,3'-[3H]indol]-2'(1'H)-one

Prepared according to the procedure for example 18: mp 171–172° C.; $^1$H-NMR (CDCl$_3$) δ8.43 (s, 1H), 7.62 (d, 1H, J=1.8 Hz), 7.42 (dt, 1H, J=6.2, 2.0 Hz), 7.39–7.37 (m, 1H), 7.33 (dt, 1H, J=5.1, 1.3 Hz), 7.26 (dq, 1H, J=5.9, 2.1 Hz) 7.05–6.99 (m, 2H), 2.03–1.64 (m, 10H); MS ((+)APCI) m/z 296 [M+H]$^+$.

EXAMPLE 22

5'-(3,5-Difluorophenyl)spiro[cyclohexane1,3'-[3H]indol]-2'(1'H)-one

Prepared according to the procedure for example 18: mp 180–183° C.; $^1$H-NMR (CDCl$_3$) δ8.35 (s, 1H), 7.59 (d, 1H, J=2.0 Hz), 7.40 (dd, 1H, J=6.2, 2.0 Hz), 7.10–7.03 (m, 2H), 6.99 (d, 1H, J=8.1 Hz), 7.76 (tt, 1H, J=4.3, 2.3 Hz), 2.05–1.62 (m, 10H); MS ((+)APCI) m/z 314 [M+H]$^+$.

EXAMPLE 23

5-(3,4-Difluorophenyl)spiro[cyclohexane-1,3-[3H]indol]-2(1H)-one

Prepared according to the procedure for example 14: mp. 187–189° C.; $^1$H-NMR (DMSO-d$_6$) δ1.5–2.0 (m, 10H), 6.9 (d, J=8.13 Hz, 1H), 7.40–7.51 (m, 3H), 7.66–7.76 (m, 2H), 10.4 (s, 1H); MS (−ESI) m/z 312 (M−H)$^−$.

EXAMPLE 24

5-[3-(Methylthio)phenyl]spiro [cyclo-hexane-1,3-[3H]indol]-2(1H)-one

Prepared according to the procedure for example 18: $^1$H NMR (CDCl$_3$) δ1.62–2.06 (m, 10H), 2.54 (s, 3H), 6.96 (d, J=8.0 Hz, 1H), 7.2–7.5 (m, 5H), 7.62 (s, 1H), 7.75 (s, 1H); $^{13}$C NMR (DMSO-d$_6$) δ16.37 (q), 21.62, 25.58, 33,37 (t), 48.67 (s), 110.55, 123.56, 124.36, 125.68, 126.94, 129.64 (d), 135.31, 136.91, 139.33, 140.27, 142.49, 184.29 (s); MS (EI) m/z 324 (M+H)$^+$.

EXAMPLE 25

5'-[3-(Methysulfinylphenyl]spiro[cyclohexane-1,3'-[3H]indol]-2'(1'H)-one

A solution of 5-[3-(Methylthio)phenyl]spiro[cyclo-hexane-1,3-[3H]indol]-2(1H)-one (0.15 g, 0.46 mmol) in methanol (6 cm$^3$) was treated with NaIO$_4$ (0.11 g, 0.51 mmol). The reaction was allowed to stir at RT overnight. The methanol was evaporated and the residue taken up in EtOAc (50 cm$^3$) and H$_2$O. The EtOAc layer was washed with brine, dried (MgSO$_4$), and evaporated. The residue was purified by column chromatography (SiO$_2$, CH$_2$Cl$_2$:methanol, 8:2) to afford the title compound (0.11 g, 0.32 mmol, 70%) as a white solid: mp. 190–191° C. $^1$H NMR (CDCl$_3$) δ1.65–2.05 (m, 10H), 2.80 (s, 3H), 7.02 (dd, J=8.0, 3.1 Hz, 1H), 7.46 (d, J=8.0 Hz, 1H), 7.52–7.75 (m, 4H), 7.0 (s, 1H), 8.7 (s, 1H); $^{13}$C NMR (DMSO-d$_6$) δ21.59, 25.54, 33.44 (t), 44.38 (q), 48.46 (s), 110.53, 12.05, 123,31, 127.08, 129.94, 130.15 (d), 134.17, 137.2, 140.73, 143.27, 146.61, 183.71 (s); MS (EI) m/z 339 (M)$^+$.

EXAMPLE 26

5-[3-(Methylsulfonyl)phenyl]spiro[cyclohexane-1,3-[3H]indol]-2(1H)-one

A solution of the 5-[3-(Methylthio)phenyl]spiro[cyclo-hexane-1,3-[3H]-indol]-2(1H)-one (0.15 g, 0.46 mmol) in CH$_2$Cl$_2$ (2 cm$^3$) was added to a solution of mCPBA (0.4 g, 2.3 mmol) in CH$_2$Cl$_2$ (5 cm$^3$) at RT. The reaction was allowed to stir overnight. The mixture was diluted with CH$_2$Cl$_2$ (50 cm$^3$) and washed with saturated bicarbonate solution, water, brine, dried (MgSO$_4$), and evaporated. The residue was crystallized (Hexane-EtOAc) to afford the title compound (0.132 g, 0.8 mmol, 80%) as an off white solid: mp. 240° C.; 1H NMR (CDCl$_3$) δ1.55–2.1 (m, 10H), 3.15 (s, 3H), 7.01 (d, J=8.1 Hz, 1H), 7.47 (dd, J=8.1, 1.5 Hz, 1H), 7.6–7.7 (m, 2H) 7.82–7.97 (m, 3H), 8.12 (s, 1H); $^{13}$C NMR (DMSO-d$_6$) δ21.54, 25.50, 33.45 (t), 44.97 (q), 48.44 (s), 110.60, 123.28, 125.92, 127.20, 128.52, 130.31 (d), 132.46, 133.65, 137.34, 140.70, 141.53, 143.25, 183.63 (s); MS (EI) m/z 356 (M+H)$^+$.

EXAMPLE 27

5'-(3-Chloro-5-fluorophenyl)spiro[cyclohexane-1,3'-[3H]indol]-2'(1'H)-one

Prepared according to the procedure for example 18: mp 178–180° C.; $^1$H-NMR (CDCl$_3$) δ8.50 (s, 1H), 7.57 (d, 1H, J=1.8 Hz), 7.39 (dd, 1H, J=6.2, 1.9 Hz), 7.33–7.32 (m, 1H), 7.15 (dq, 1H, J=5.7, 1.7, 0.7 Hz), 7.06 (dq, 1H, J=4.2, 1.9, 0.4 Hz), 7.00 (d, 1H, J=8.1 Hz), 2.05–1.64 (m, 10H); MS ((−)ESI) [M−H]$^−$@ m/z 328.

EXAMPLE 28

5-(3-Bromo-5-fluorophenyl)spiro[cyclohexane1,3-[3H]indol]2(1H)-one

Prepared according to the procedure for example 18: mp. 194–196° C.; $^1$H NMR (CDCl$_3$) δ1.66–2.04 (m, 10H), 7.00 (d, 1H, J=8.0 Hz), 7.17–7.28 (m, 2H), 7.41 (dd, 1H, J=8, 1.8 Hz), 7.49 (t, 1H, J=1.4 Hz), 7.58 (d, 1H, J=1.5 Hz) and 8.24 (s, 1H, br); MS ((+)-EI) m/z 373/375 [M$^+$].

EXAMPLE 29

5'-(3-Fluoro-5-methylphenyl)spiro[cyclohexane-1,3'-[3H]indol]-2'(1'H)-one

A solution of 3-fluoro-5-methoxybenzene trifluoromethanesulfonate (1.6 g, 5.8 mmol) and tetrakis-(triphenylphosphene)-palladium(0) (0.33 g, 286 mmol) in dimethoxyethane (50 mL) was stirred under N$_2$ for 20 minutes. To this mixture was then added lithium bromide (1.5 g, 172 mmol). This solution was stirred under N$_2$ for 10 minutes. To this mixture was then added (2'-oxo-2,3-dihydrospiro[cyclohexane-1,3'-[3H]-indol]-5'-yl) boronic acid (1.3 g, 5.7 mmol) and sodium carbonate (1.2 g, 11.5 mmol) in distilled water (5 mL). The solution was brought to reflux for 6 hours, cooled to room temperature, poured into distilled water and extracted with EtOAc (×3). The combined organic extracts were washed with 2N NaOH, water, brine, dried (MgSO$_4$), and evaporated. The residue was purified by column chromatography (SiO$_2$, EtOAc:Hexane 2:5) to afford the title compound (0.6 g, 32%) as an off-white solid: mp 180–182° C.; $^1$H-NMR (CDCl$_3$) δ8.21 (s, 1H), 7.60 (d, 1H, J=1.8 Hz), 7.41 (dd, 1H, J=6.2, 1.9 Hz), 6.97 (d, 1H, J=7.9 Hz), 6.88–6.86 (m, 1H), 6.84 (t, 1H, J=1.8 Hz), 6.59 (dt, 1H, J=6.2, 2.2 Hz), 3.86 (s, 3H), 2.00–1.62 (m, 10H); MS ((-ESI) [M–H]$^-$@ m/z 324.

EXAMPLE 30

5'-(3-Nitrophenyl)spiro[cyclohexane-1,3'-[3H]indol]-2'(1'H)-one

Prepared according to the procedure for example 14: mp. 196–198° C., $^1$H NMR (CDCl$_3$) δ1.67–1.81 (m, 6H), 1.82–2.05 (m, 4H), 7.04 (d, 1H, J=8 Hz), 7.48 (dd, 1H, J=8 and 1 Hz), 7.59 (d, 1H, J=8 Hz), 7.63–7.65 (m, 1H), 7.87–7.90 (m, 1H), 8.16–8.20 (m, 1H), 8.38 (s, br, 1H), 8.41 (t, 1H, J=2 Hz); MS ((–)ESI) m/z 321 (M–H)$^-$.

EXAMPLE 31

3-(1,2-Dihydro-2-oxospiro[cyclohexyane-1,3-[3H]indol]-5-yl)aniline

A solution of 5'-(3-Nitrophenyl)spiro[cyclohexane-1,3'-[3H]indol]-2'(1'H)-one (3.6 g, 11 mmol) in methanol (150 ml) was shaken with 10% palladium on charcoal (1 g) under a hydrogen atmosphere at 40 psi. The catalyst was filtered off and the solution was concentrated to obtain a residue. The residue was dissolved in ether and ethanolic hydrochloric acid was added. The solid thus obtained was recrystallized from methanol/ether to obtain the title compound (1.7 g, 47%): m.p. 275–278° C.; $^1$H-NMR (DMSO-d$_6$) δ1.5–2.0 (m, 10H), 6.98 (d, J=8.05 Hz, 1H), 7.26 (d, J=7.90 Hz, 1H), 7.45–7.62 (m, 4H), 7.67 (d, J=8.3 Hz, 1H), 9.0–11.0 (s, 2H, br), 10.5 (s, 1H), MS ((+)APCl) m/z 293 (M+H).

EXAMPLE 32

5-(3-Fluoro-5-nitrophenyl)spiro[cyclohexane-1,3-[3H]indol]-2(1H)-one

Prepared according to the procedure for example 18: mp. 191–193° C.; $^1$H NMR (CDCl$_3$) δ1.66–2.07 (m, 10H), 7.07 (d, 1H, J=8 Hz), 7.49 (dd, 1H, J=8, 1.8 Hz), 7.59–7.64 (m, 2H), 7.89 (dt, 1H, J=8.1, 2.1 Hz), 8.25 (s, 1H) and 8.54 (s, 1H); MS ((+)–APCI) m/z 341 [M+H]$^+$.

EXAMPLE 33

5'-(3-Hydroxyphenyl)spiro[cyclohexane-1,3'-[1,3H]indol]-2'(1'H)-one

Prepared according to the procedure for example 18: m.p. 213–216° C.; $^1$H NMR (CDCl$_3$) δ1.60–1.96 (m, 10H), 6.78–6.82 (m, 1H), 6.94 (d, 1H, J=8 Hz), 7.01–7.04 (m, 2H), 7.23 (t, 1H, J=7.7 Hz), 7.38 (d, 1H, J=8 Hz), 7.61 (s 8.91 (s, 1H) and 9.73 (s, 1H, br); MS ((+)-APCI) m/z 294 [M+H]$^+$.

EXAMPLE 34

4-(1,2-Dihydro-2-oxospiro[cyclohexane-1,3-[3H]indol]-5-yl)-2-thiophenecarbonitrile 3-(Trimethylstannyl)-2-thiophenecarbonitrile A solution of 3-bromo-2-thiophenecarbonitrile (0.8 g, 4.3 mmol), tetrakis(triphenylphosphine)palladium(0) (0.25 g, 0.2 mmol) and hexamethylditin (1.4 g, 4.3 mmol) in dimethoxyethane (5 cm$^3$) was heated under reflux for 14 hours then cooled to room temperature. The reaction mixture was absorbed onto florisil and purified by column chromatography (SiO$_2$, methylene chloride: hexane 1:9) to afford the title compound (1.04 g, 3.8 mmol, 90%) as a clear viscous oil: $^1$H NMR (CDCl$_3$) δ0.35 (s, 9H), 7.56 (d, J=0.9 Hz, 1H), 7.66 (d, J=0.9 Hz, 1H).

A solution of the 5'-bromospiro[cyclohexane-1,3'-[3H]indol]-2'(1'H)-one (0.53 g, 1.9 mmol), dichlorobis (triphenylphosphine) palladium(II) (0.1 g, 0.14 mmol) and triphenylarsine (0.14 g, 0.47 mmol) in dimethoxyethane (8 cm$^3$) was stirred under N$_2$ for 20 min. To this mixture was then added 3-(trimethylstannyl)-2-thiophenecarbonitrile (0.64 g, 2.35 mmol). The solution was brought to reflux for 32 h. After cooling to room temperature the reaction mixture was absorbed onto florisil and purified by column chromatography (SiO$_2$, ethyl acetate: hexane 2:3) to afford the title compound (0.43 g, 1.39 mmol, 74%) as an off white solid: $^1$H NMR (CDCl$_3$) δ1.56–2.1 (m, 10H), 6.97 (d, J=8.0 Hz, 1H), 7.39 (dd, J=8.03, 1.45 Hz, 1H), 7.57 (d, J=1.45 Hz, 1H), 7.59 (d, J=1.4 Hz, 1H), 7.84 (d, J=1.4 Hz, 1H), 8.32 (br s, 1H); 13C-NMR (CDCl$_3$) δ22.07, 26.56, 34.4 (t), 48.13 (s), 110.18 (d), 111.3, 114.75 (s), 122.92, 126.76 (d), 128.44 (s), 137.55 (d), 138.11, 142.71, 144.49, 182.13 (s); MS (EI) m/z 307 (M–H)+.

EXAMPLE 35

5-(2'-oxo-2',3'-dihydrospiro[cyclohexane-1,3'-[3H]indol]-5'yl-2-thiophenecarbonitrile 5-Bromo-2-thiophenecarbonitrile A mixture of 5-bromo-2-thiophenecarboxaldehyde (96.0 g, 500 mmol), hydroxylamine hydrochloride (111.9 g, 500 mmol), pyridine (500 mL), and ethanol (500 mL) was heated under nitrogen at reflux for two hours. The reaction mixture was cooled to ambient temperature and concentrated in vacuo to give an oil. The crude product was triturated twice with ice water and the solid obtained was collected on a filter. A mixture of a portion of the above solid (44.31 g, 215 mmol), copper (II) acetate monohydrate (4.2 g, 21 mmol) in acetonitrile (1.4L) was heated at reflux for three hours. The solvent was removed in vacuo and the residue was dissolved in ethyl acetate. The solution was washed with 5% aqueous sulfuric acid (2×30 mL), water (2×30 mL), brine (20 mL), and dried (MgSO$_4$). The solvent was removed in vacuo and the residue was dissolved in a ninimum amount of chloroform (1L) and allowed to crystallize. The crystal obtained was collected on a filter and the filtrate was concentrated and purified by a chromatography (silica gel, chloroform) to give the subtitled compound as an off-white solid (31.5 g combined, 58%).: IR (film) cm$^{-1}$ 2200; $^1$H-NMR (CDCl$_3$) δ7.39–7.38 (d, 1H, J=4.1 Hz), 7.10 (d, 1H, J=4.0 Hz); MS (EI) m/z 187 (M$^+$, 98%) 189(M$^+$, 100%).

The title compound was prepared according to the procedure for example 18 using 5-bromo-2-thiophenecarbonitrile and (2'-oxo-2',3'-dihydrospiro [cyclohexane -1,3'-[3H]indol]-5'-yl) boronic acid: mp. 225–228° C.; $^1$H NMR (DMSO-d$_6$) δ1.63 (m, 8H), 1.90 (m, 2H) 6.91 (d, 1H, J=8.13 Hz), 7.55 (dd, 1H, J=8.13, 1.76 Hz), 7.6 (d, 1H, J=4.17 Hz), 7.75 (d, 1H, J=1.76 Hz), 7.93 (d, 1H, J=4.17 Hz), 10.51 ) s, 1H); MS ((+)APCI) m/z 309 [M +H]$^+$.

EXAMPLE 36

4-Methyl-5-(2'-oxo-2',3'-dihydrospiro[cyclohexane-1,3'-[3H]indol]-5'-yl)-2-thiophene carbonitrile Prepared according to the procedure for example 18: mp. 200–203° C.; $^1$H NMR (DMSO-d$_6$) δ1.63 (m, 8H), 1.87 (m, 2H), 2.27 (s, 3H), 6.95 (d, 1H, J=8.13 Hz), 7.34 (dd, 1H, J=8.13, 1.98 Hz) 7.54 (d, 1H, J=1.98 Hz), 7.82 (s, 1H) 10.50 (s, 1H); MS ((+)APCI) m/z 323 [M +H]$^+$.

EXAMPLE 37

4-Ethyl-5-(2'-oxo-2',3'-dihydrospiro[cyclohexane-1, 3'-1,3H]indol-5'-yl)-2-thiophenecarbonitrile Prepared according to the procedure for example 18: mp 214–217° C. $^1$H NMR (DMSO-d$_6$) δ10.55 (s, 1H), 7.95 (s, 1H), 7.51 (s, 1H), 7.33–7.30 (m, 1H), 6.98–6.96 (d, 2H J=8.0 Hz), 2.67–2.62 (m, 2H), 1.89–1.86 (m, 2H), 1.69–1.55 (m, 8H), 1.20–1.15 (t, 3H); MS ((+)APCI) m/z 337 [M+H]$^+$. Anal.Calc. For C$_{20}$H$_{20}$N$_2$OS.1/2 H$_2$O: C, 69.54; H, 6.13; N, 8.11 . Found: C, 69.51 ; H, 6.06; N, 7.57.

EXAMPLE 38

5-(1',2'-Dihydro-2'-oxospiro[cyclohexane-1,3'-[3H] indol]-5'-yl)-thiophene-3-carbonitrile Prepared according to the procedure for example 18: mp. 188–190° C.; $^1$H-MNR (DMSO-d$_6$) δ1.5–2.0 (m, 10H), 6.89 (d, J=7.91 Hz, 1H), 7.49 (dd, J=7.91, 1.98 Hz, 1H), 7.75 (d, J=1.76 Hz, 1H), 7.86 (d, J=1.32 Hz, 1H), 8.44 (d, J=1.32 Hz, 1H); MS (-ESI) m/z 307 (M-H).

EXAMPLE 39

2-(1',2'-Dihydro-2'-oxospiro[cyclohexane-1,3'-[3H] indol]-5'-yl)-thiophene-2-carbonitrile Prepared according to the procedure for example 18: mp. 207–9° C.; $^1$H-NMR (DMSO-d$_6$) δ1.4–2.0 (m, 10H), 7.0 (d, J=8.13 Hz, 1H), 7.48 (d, J=5.27 Hz, 1H), 7.54 (dd, J=8.13 Hz, 1.98 Hz, 1H), 7.71 (d, J=5.49 Hz, 1H), 7.85 (d, J=1.76 Hz, 1H), 10.6 (s, 1H); MS (-ESI) m/z 307 (M-H).

EXAMPLE 40

5-(1',2'-Dihydro-2'-oxospiro[cyclohexane-1,3'-[3H] indol]-5'-yl)-3-furancarbonitrile Prepared according to the procedure for example 18: mp. 243–245° C. $^1$H-NMR (DMSO-d$_6$) δ10.48 (s, 1H), 8.62 (d, 1H J=0.7 Hz), 7.76 (d, 1H J=1.5 Hz), 7.58–7.55 (dd, 1H), 7.33 (d, 1H J=0.7 Hz), 6.92–6.90 (d, 1H J=8.1 Hz), 1.87–1.83 (m, 2H), 1.73–1.53 (m, 8H). MS ((+)EI) m/z 292 (M+).

EXAMPLE 41

5-(5-Chloro-2-thienyl)spiro[cyclohexane-1,3-[3H] indol]-2(1H)-one

Prepared according to the procedure for example 18: m.p. 191–192° C.; $^1$H NMR (CDCl$_3$) δ1.6–2.1 (m, 10H), 6.85–6.95 (m, 2H), 6.98 (d, J=4.0 Hz, 1H), 7.36 (dd, J=7.5, 1.6 Hz, 1H), 7.53 (d, J=0.9 Hz, 1H), 7.80 (br s, 1H),; $^{13}$C-NMR (THF-d $_8$) δ21.35, 25.33, 33.12 (t), 48.32 (s), 110.40, 121.66, 121.96, 125.44, 127.25 (d), 128.17, 128.43, 136.92, 140.20, 143.43, 183.72 (s); MS (EI) m/z 318 (M+H)$^+$.

EXAMPLE 42

5-(5-Acetyl-2-thienyl)spiro[cyclohexane-1,3-[3H] indol]-2(1H)-one

Prepared according to the procedure for example 18: m.p. 195–196° C., $^1$H NMR (CDCl$_3$) δ1.6–2.1 (m, 10H), 2.58 (s, 3H), 6.95 (d, J=8.1 Hz, 1H), 7.25 (d, J=4.0 Hz, 1H), 7.54 (dd, J=8.1, 1.7 Hz, 1H), 7.66 (d, J=4.0 Hz, 1H), 7.7 (d, J=1.7 Hz, 1H), 7.9 (br s, 1H),; $^{13}$C NMR (CDCl$_3$) δ22.24, 26.19 (t), 27.59 (q), 33.99 (t), 49.02 (s), 111.39, 123.45, 124.12, 127.02 (d), 128.59 (s), 134.79 (d), 137.92, 142.23, 143.41, 154.47, 184.51, 191.76 (s); MS (EI) m/z 326 (M+H)$^+$.

EXAMPLE 43

5-(2'-oxo-2',3'-dihydrospiro[cyclohexane-1,3'-[3H] indol]-5'yl-2-nitro-thiophene Prepared according to the procedure for example 11: mp. 242° C. (decomp.); $^1$H NMR (DMSO-d$_6$) δ1.62–1.67 (m, 6H), 1.90–1.99 (m, 2H), 6.94 (d, 1H, J=8.1 Hz), 7.64 (d, 1H, J=4.5 Hz), 7.67 (dd, 1H, J=8.2, 1.8 Hz), 7.86 (d, 1H, J=1.5 Hz), 8.15 (d, 1H, J=4.5 Hz), 10.62 (s, 1H); MS (EI) m/z 328 (M)$^-$.

EXAMPLE 44

5'-(5-Nitro-1H-pyrrol-2-yl)spiro[cyclohexane-1,3'-[3H]indol]-2'(1'H)-one 2-(1',2'-Dihydro-2'-oxospiro[cyclohexane-1,3'-[3H]indol]-5'-y-1H-pyrrole-1-carboxylic acid, tert-butyl ester To a solution of 5'-bromo-spiro[cyclohexane-1,3'-indolin]-2'-one (3.4 g, 12 mmol) in 1,2-DME (100 mL) under a nitrogen atmosphere was added tetrakis (triphenylphospine)palladium(0) (70 mg, 5 mol %). After 15 min, 2-borono -1H-pyrrole-1-carboxylic acid, 1-tert butyl ester (1.3 eq, 3.31 g, 15.6 mmol) and a solution of K$_2$CO$_3$ (2.3 eq, 3.83 g, 27.6 mmol) in water (5 mL) were added sequentially. The solution was heated to 80° C. for 3 h and allowed to cool. The reaction mixture was poured into water (200 mL) and extracted with EtOAc (2×100 mL). The organic layers were combined, washed with brine (150 mL) and dried over MgSO$_4$. The solution was filtered, concentrated in vacuo, and the residue was purified by flash column chromatography on silica gel (eluting with 30% EtOAc/hexane) to give subtitled compound: (3.4 g, 76%) as a white powder, mp 177° C. $^1$H NMR (CDCl$_3$; 300 MHz) δ1.38 (s, 9H), 1.59–1.93 (m, 10H), 6.18 (m, 1H), 6.23 ('t', 1H, 3 Hz), 6.91 (d, 1H, J=8 Hz), 7.21 (d, 1H, J=8 Hz), 7.34 (m, 1H), 7.44 (s, 1H), 8.33 (br s, 1H, D₂Oex). MS ((+)-APCI) m/z 367 [(M+H)⁺]. Anal. Calcd for $C_{22}H_{26}N_2O_3$: C, 72.11; H, 7.15; N, 7.64. Found: C, 71.7; H, 7.16; N, 7.5.

2-(1',2'-Dihydro-2'-oxospiro[cyclohexane-1,3'-[3H]indol]-5'-yl)-5-nitro-1H-pyrrole-1-carboxylic acid, tert-butyl carbamate To a solution of 2-(1',2'-dihydro-2'-oxospiro[cyclohexane-1,3'-[3H]indol]-5'-yl)-1H-pyrrole-1-carboxylic acid, tert-butyl ester (72 mg, 0.2 mmol) in MeCN (5 mL) at room temperature was added silver nitrate (1.05 eq, 35 mg, 0.2 mmol). After 5 min, acetyl chloride (1.0 eq, 15 mg, 0.2 mmol) in MeCN (5 mL) was added and the solution was allowed to stir for 16 h. Dichloromethane (10 mL) was added, and the solution was filtered through celite and washed sequentially with water, sat. NaHCO₃, water and brine (10 mL of each). The solution was dried over MgSO₄, filtered, and concentrated in vacuo. The residue was purified by flash column chromatography on silica gel (eluting with 40% EtOAc/hexane) to give the subtitled compound (56 mg, 70%) as a yellow oil which crystallized from acetone/hexane, mp 163° C. (dec).

2-(1',2'-Dihydro-2'-oxospiro[cyclohexane-1,3'-[3H]indol]-5'-yl)-5-nitro-1H -pyrrole-1-carboxylic acid, tert-butyl ester (0.31 g, 0.85 mmol) was placed in a 5 mL round bottomed flask stoppered with a rubber septum and equipped with nitrogen inlet and a needle to allow gaseous outflow. A vigorous flow of nitrogen was maintained as the flask was placed in an oil bath and heated to 200° C. After 5 min at this temperature, the flask was removed from the oil bath and allowed to cool. The black residue was washed into a larger flask with acetone and adsorbed onto a small amount of silica gel. Purification by flash column chromatography on silica gel (eluting with 40% EtOAc/hexane) gave the title carbamate (0.20 g, 85%) as a yellow oil which crystallized from acetone/hexane, mp 278° C. (dec). ¹H NMR (DMSO-d₆; 300 MHz) δ1.55–1.87 (m, 10H), 6.80 (d, 1H, J=4 Hz), 6.91 (d, 1H, J=8 Hz), 7.27 (d, 1H, J=4 Hz), 7.77 (dd, 1H, J=8, 1 Hz), 8.04 (d, 1H, J=1 Hz), 10.51 (s, 1H), 13.21 (br s, 1H). MS ((+)-APCI) m/z 312 [(M+H)⁺]. Anal. Calcd for $C_{17}H_{17}N_3O_3$: C, 65.58; H, 5.5; N, 13.5. Found: C, 65.57; H, 5.54; N, 13.44.

EXAMPLE 45

5'-(5-Nitro-1-methyl-pyrrol-2-yl)spiro[cyclohexane-1,3'-[3H]indol]-2'(1'H)-one

5'-(1-Methyl-pyrrol-2-yl)spiro[cyclohexane-1,3'-[3H]indol]-2'(1 'H)-one

A mixture of 5'-(1H-pyrrol-2-yl)spiro[cyclohexane-1,3'-[3H]indol]-2'(1')-one (0.46 g, 1.7 mmol) and potassium carbonate (5 eq, 1.18 g, 8.6 mmol) in DMF (2 mL) at room temperature was treated with a solution of iodomethane (3 eq, 0.32 g, 5.1 mmol) in DMF (1 mL). The solution was stirred 16 h at room temperature, then poured into water (10 mL). EtOAC (15 mL) was added, the layers were separated, and the aqueous layer was extracted with EtOAc (2×100 mL). The organic layers were combined, washed with brine (15 mL) and dried over MgSO₄. The solution was filtered, concentrated in vacuo, and the residue was purified by flash column chromatography on silica gel (eluting with 40% EtOAc/hexane) to give the subtitled compound (0.44 g, 76%) as a white powder, mp 148–9° C. ¹H NMR (DMSO-d₆; 400 MHz) δ1.50–1.62 (m, 3H), 1.62–1.82 (m, 5H), 1.83–1.94 (m, 2H), 3.11 (s, 3H), 6.08 (m, 1H), 6.42 (m, 1H), 6.79 (m, 1H), 6.97 (d, 1H, J=8.1 Hz), 7.51 (dd, 1H, J=8.1, 1.8 Hz), 7.70 (d. 1H, J=1.7 Hz), 11.20 (br s, 1H). Anal. Calcd for $C_{18}H_{20}N_2O_1$: C, 77.11; H, 7.19; N, 9.98. Found: C, 76.44; H, 7.21; N, 9.96.

A mixture of 5'-(1-methyl-pyrrol-2-yl)spiro[cyclohexane-1,3'-[3H]indol]-2'(1'H)-one (0.36 g, 1.3 mmol) and silver nitrate (1.1 eq, 0.24 g, 1.4 mmol) in acetonitrile (10 mL) at room temperature was treated with acetyl chloride (1.1 eq, 0.1 mL, 1.4 mmol). The mixture was stirred 1 h at this temperature and then dichloromethane (30 mL) was added and the mixture was filtered through celite. The organic phase was washed sequentially with water (20 mL), sat. aq. NaHCO₃ (20 mL), and brine (20 mL). The solution was dried over MgSO₄, filtered, and concentrated in vacuo. The residue was purified by flash column chromatography on silica gel (eluting with 40% EtOAc/hexane) to give the title compound (21 mg, 5%) as a yellow powder, mp 210° C. ¹H NMR (DMSO-d₆; 300 MHz) δ1.55–1.97 (m, 10H), 3.15 (s, 3H), 6.77 (dd, 1H, J=4.2, 2.3 Hz), 7.05 (d, 1H, J=8.2 Hz), 7.21 (dd, 1H, J=4.2, 2.3 Hz), 7.83 (dd, 1H, J=1.8, 8.2 Hz), 8.0 (d, 1H, J=1.8 Hz), 13.0 (br s, 1H). MS ((+)-APCI) m/z 326 [(M+H)⁺]. Anal. Calcd for $C_{18}H_{19}N_3O_3$: C, 65.45; H, 5.89; N, 12.91. Found: C, 64.66; H, 5.76; N, 12.52.

EXAMPLE 46

5'-(1H-Indol-4-yl)spiro[cyclohexane-1,3'-[3H]indol]-2'(1'H)-one

Prepared according to the procedure for example 18: mp 211–213° C.; ¹H-NMR (CDCl₃) δ8.32 (s, 1H), 7.84 (s, 1H), 7.81 (d, 1H, J=1.8 Hz), 7.55 (dd, 1H, J=6.2, 1.8 Hz), 7.40 (dt, 1H, J=6.2, 1.0 Hz), 7.29–7.28 (m, 1H), 7.27 (t, 1H, J=3.1 Hz), 7.18 (dd, 1H, J=6.4, 0.9 Hz), 7.00 (dd, 1H, J=7.5, 0.4 Hz), 6.72–6.71 (m, 1H), 2.00–1.59 (m, 10H); MS ((+)APCI) [M+H]⁺@ m/z 317.

EXAMPLE 47

3-(1',2'-Dihydro-2'-oxospiro[cyclohexane-1,3'-[3H]indol-5'-yl)benzonitrile

A solution of 3-(1',2'-Dihydro-2'-oxospiro[cyclohexane-1,3'-[3H]indol-5'-yl)benzaldehyde oxime (0.48 g, 1.49 mmol) in chloroform (10 cm³) was treated with selenium dioxide (0.38 g, 3.50 mmol) and heated under reflux. After 16 h, the mixture was concentrated and the residue purified by column chromatography (SiO₂, EtOAc:hexane 1:4) and the product re-crystallized from EtOAc-hexane to afford the title compound (0.161 g, 0.53 mmol, 35%) as a white solid: mp. 190–191° C.; ¹H NMR (CDCl₃) δ1.59–1.87 (m, 6H), 1.88–2.09 (m, 4H), 7.03 (d, 1H, J=8 Hz), 7.42 (dd, 1H, J=8, 2 Hz), 7.54 (t, 1H, J=8 Hz), 7.58–7.65 (m, 2H), 7.78 (dt, 1H, J=7, 2 Hz), 7.83 (m, 1H), 8.26 (s, 1H, br); MS ((+) ESI) m/z 303 (M+H)⁺.

EXAMPLE 48

3-(1,2-Dihydro-2-oxospiro[cyclohexane-1,3-[3H]indol]-5yl)-5-fluorobenzonitrile

To a solution of 3,5-dibromofluorobenzene in diethyl ether (100 cm³) at –78° C. was added n-butyl lithium (2.5 M, 8 cm³, 20 mmol) dropwise. After 30 min. the mixture was treated with DMF (20 cm3) in diethyl ether (10 cm3) and stirring was continued at –78° C. After 30 min. the mixture was quenched with dilute HCl aq., separated and the aqueous layer was extracted with EtOAc. The combined organic layers were combined, washed with water, brine, dried (MgSO₄) and evaporated to give 3-fluoro-5-bromobenzaldehyde (4.0 g, 19.7 mmol, 100%) as an oil: ¹H NMR (CDCl₃) δ inter alia 7.50–7.53 (m, 2H), 7.82 (s, 1H) and 9.93 (m, 1H); MS (EI) m/z 202, 204 [M⁺].

To a solution of the last cited compound (4.0 g, 19.7 mmol) in ethanol:water (8:2, 50 cm$^3$), was added sodium acetate (1.72 g, 21 mmol) and hydroxylamine hydrochloride (1.45 g, 21 mmol), and the mixture was heated under reflux. After 30 min., the mixture was cooled, evaporated and the residue partitioned between water and EtOAc. The aqueous layer was re-extracted with EtOAc and the combined organic layers were washed with water, saturated sodium hydrogen carbonate solution, brine, dried (MgSO$_4$) and evaporated to give 3-fluoro-5-bromobenzaldehyde oxime (3.76 g, 17.24 mmol, 87%) which was used without further purification: $^1$H NMR (CDCl$_3$) δ7.24–7.27 (m, 2H), 7.50 (s, 1H), 7.68 (s, 1H) and 8.04 (s, 1H); MS (EI) m/z 217 [M$^+$].

The above oxime (3.76 g, 17.24 mmol) and copper (II) acetate (370 mg) were dissolved in acetonitrile (100 cm$^3$) under nitrogen and heated under reflux. After 5 h, the mixture was evaporated, the residue taken into EtOAc, washed with sulfuric acid (1N), water, brine, dried (MgSO$_4$) and evaporated to give 3-fluoro-5-bromobenzonitrile (3.08 g, 15.39 mmol, 89%) which was used without further purification.

The above bromide (3.0 g, 15 mmol) and tetrakis (triphenylphosphine)palladium (0) (0.86 g, 0.75 mmol) were dissolved in dimethoxyethane (130 cm$^3$) under nitrogen. After 15 min. (2'-oxo-2,3-dihydrospiro[cyclohexane-1,3'-[3H]indol]-5'-yl) boronic acid (2.82 g, 11.5 mmol) and sodium carbonate (3.1 g, 29.3 mmol) dissolved in water (40 cm$^3$) were added, and the mixture heated under reflux. After 8 h the mixture was cooled, poured into water and extracted with EtOAc (x3). The combined organic layers were then washed with water, dried (MgSO$_4$) and evaporated. The residue was then purified by column chromatography (EtOAc:hexane, gradient elution), and the product recrystallized from methanol to give 3-(1,2-Dihydro-2-oxospiro[cyclohexane -1,3-[3H]indol]-5-yl)-5-fluorobenzonitrile (1.78 g, 5.55 mmol, 48%): mp 199–205° C.; $^1$H NMR (CDCl$_3$) δ1.64–2.03 (m, 10H), 7.03 (d, 1H, J=8 Hz), 7.31 (dt, 1H, J=7.7 and 1.6 Hz), 7.41 (dd, 1H, J=8, 1.7 Hz), 7.49 (dt, 1H, J=9.6, 2 Hz), 7.58 (d, 1H, J=2 Hz), 7.64 (s, 1H) and 8.37 (s, 1H): MS (EI) m/z 320 [M$^+$].

EXAMPLE 49

3-(1,2-Dihydro-2-oxospiro[cyclohexane-1,3-[3H] indol]-5-yl)-4-fluorobenzonitrile Prepared according to the procedure for example 18: mp. 205–206° C. $^1$H NMR (DMSO-d$_6$) δ10.47 (s,1H), 8.08–8.06 (dd, 1H), 7.89–7.85 (m, 1H), 7.65 (s, 1H), 7.54–7.49 (m, 1H), 7.43–7.40 (tt, 1H), 6.95–6.93 (d, 1H J=7.9 Hz), 1.97–1.83 (m, 2H), 1.69–1.55 (m, 8H); MS (EI) m/z 320 (M$^+$)

EXAMPLE 50

3-(1'-Diethoxymethyl-1',2'-dihydro-2'-oxospiro [cyclohexane-1,3'-[3H]indol]-5'-yl)-5-fluorobenzonitrile A solution of 3-(1',2'-dihydro-2'-oxospiro[cyclohexane-1, 3'-[3H]indol]-5'-yl)-5-fluorobenzonitrile (1.0 eq, 0.27 g, 0.84 mmol) in triethylorthoformate (2 mL, 12 mmol) was heated to 150° C. for 1 h. The reaction mixture was allowed to cool, the excess triethylorthoformate was removed in vacuo, and the residue was purified by flash column chromatography on silica gel (eluting with 10% EtOAc/hexane) to give the title compound (0.2 g, 56%) as a white powder, mp 146° C. $^1$H NMR (DMSO-d$_6$; 400 MHz) 671.13 (t, 6H, J=7 Hz), 1.60–1.96 (m, 10H), 3.48 (m, 2H), 3.66 (m, 2H), 6.17 (s, 1H), 7.35 (d, 1H, J=8.3 Hz), 7.68 (dd, 1H, J=2.0, 8.3 Hz), 7.77 (ddd, 1H, J=1.3, 2.4 Hz), 7.89 (d, 1H, J=2.0 Hz), 7.92 (dt, 1H, J=2.4, 10.5 Hz)8.08 (dd, 1H, J=1.3, 2.9 Hz). MS ((+)-EI) m/z 422 [M$^+$]. Anal. Calcd for C$_{25}$H$_{27}$FN$_2$O$_3$: C, 71.07; H, 6.44; N, 6.63. Found: C, 70.75; H, 6.48; N, 6.52.

EXAMPLE 51

3-(7'-Bromo-1',2'-dihydro-2'-oxospiro[cyclohexane-1,3'-[3H]indol]-5'-yl)-5-fluoro-benzonitrile A mixture of 3-(1',2'-dihydro-2-oxospiro[cyclohexane-1, 3'-[3H]indol]-5'-yl)-5-fluorobenzonitrile (0.40 g, 1.23 mmol) and potassium acetate (0.13 g, 1.3 mmol) in glacial acetic acid (3 mL) at room temperature was treated with a solution of bromine (1.05 eq, 0.21 g, 1.3 mmol) in a glacial acetic acid (3 mL). After stirring for 1 h the mixture was poured onto ice (20 g). The layers were separated and the aqueous layer was extracted with dichloro methane (2×10 mL). The organic layers were combined, washed sequentially with 10% aqueous sodium thiosulfate (20 mL), water (2××10 mL), saturated sodium bicarbonate (10 mL) and brine (15 mL) and dried over MgSO$_4$. The solution was filtered, concentrated in vacuo, and the residue was purified by flash column chromatography on silica gel (eluting with 30% EtOAc/hexane) to give the title compound (0.21 g, 43%) as an oil which crystallized upon addition of 10% EtOAc/hexanes, mp 217° C. $^1$H NMR (CDCl$_3$; 300 MHz) δ1.56–2.04 (m, 10H), 7.33 (dddd, 1H, J=1.25, 2.3, 3.6 and 9.0 Hz), 7.45 (m, 1H), 7.47 (m, 2H), 7.54 (m, 1H), 7.60 (m, 1H). MS ((−)-ESI) m/z 399 [M$^-$]. Anal. Calcd for C$_{20}$H$_{16}$BrFN$_2$O$_1$: C, 60.17; H, 4.04; N, 7.02. Found: C, 60.03; H, 4.08; N, 6.83.

EXAMPLE 52

3-(7'-Nitro-1',2'-dihydro-2'-oxospiro[cyclohexane-1, 3'-[3H]indol]-5'-yl)-5-fluoro-benzonitrile A mixture of 3-(1',2'-dihydro-2'-oxospiro[cyclohexane-1, 3'-[3H]indol]-5'-yl)-5-fluorobenzonitrile (0.19 g, 0.6 mmol) and silver nitrate 0.11 g, 0.6 mmol) in trifluoroacetic acid (5 mL) was stirred 1 h at room temperature and then poured onto ice (20 g). Ether (15 mL) was added, the layers were separated, and the aqueous layer was extracted with ether (3×10 mL). The organic layers were combined and washed sequentially with water (2×20 mL), saturated aqueous NaHCO$_3$ (20 mL) and brine (15 mL) and dried over MgSO$_4$. The solution was filtered, concentrated in vacuo, and the residue was purified by flash column chromatography on silica gel (eluting with 20% EtOAc/hexane) to give the title compound (0.2 g, 94%) as a white powder, mp 196° C. $^1$H NMR (DMSO-d$_6$; 400 MHz) δ1.46–1.58 (m, 1H), 1.62–1.77 (m, 5H), 1.83 (m, 2H), 1.92–2.20 (m, 2H), 7.85 (dddd, 1H, J=1.3, 2.4, 3.7 and 8.6 Hz), 8.12 (dddd, 1H, J=1.8, 2.4, 4.2 and 10.5 Hz), 8.23 (m, 2H), 8.36 (d, 1H, J=2.0 Hz), 11.17 (bs, 1H). MS ((−)-APCI) m/z 365 [M$^-$]. Anal. Calcd for C$_{20}$H$_{16}$FN$_3$O$_3$: C, 65.75; H, 4.41; N, 11.5. Found: C, 65.4; H, 4.54; N, 11.3.

EXAMPLE 53

3-(7'-Amino-1',2'-dihydro-2'-oxospiro[cyclohexane-1,3'-[3H]indol]-5'-yl)-5-fluoro-benzonitrile To a solution of 3-(7'-nitro-1', 2'-dihydro-2'-oxospiro-[cyclohexane-1,3'-[3H]indol]-5'-yl)-5-fluorobenzonitrile (1.0 eq, 0.16 g, 0.4 mmol) in glacial acetic acid (4 mL) at room temperature was added a solution of tin (II) chloride dihydrate (0.25 g, 1.1 mmol) in hydrochloric acid (2 mL). The yellow mixture was boiled for 30 min at which point the yellow color disappeared. After cooling to room temperature, 1N HCl (10 mL) and ether (20 mL) were added. The layers were separated and the aqueous phase was extracted with ether (2×mL). The organic layers were combined, washed sequentially with water (2×20 mL), saturated aqueous $NaHCO_3$ (20 mL), and brine (20 mL). The solution was dried over $MgSO_4$, filtered, and concentrated in vacuo. The residue was purified by flash column chromatography on silica gel (eluting with 40% EtOAc/hexane) to give the title compound (70 mg, 500%) as an oil which crystallized upon addition of 10% EtOAc/hexanes, mp 241–3° C. $^1$H NMR (DMSO-$d_6$; 400 MHz) δ1.50–1.75 (m, 8H), 1.82–1.95(m, 2H), 4.98 (s, 2H), 6.90 (d, 1H, J=1.8 Hz), 7.09 (d, 1H, J=1.5 Hz), 7.75 (m, 2H), 7.90 ('s', 1H), 9.96 (bs, 1H). MS ((+)-APCI) m/z 336 [(M+H)$^+$]. Anal. Calcd for $C_{20}H_{18}FN_3O$: C, 71.63; H, 5.41; N, 12.18. Found: C, 71.16; H, 5.58; N, 12.18.

EXAMPLE 54

5-(3-cyano-4-fluorophenyl)spiro[cyclohexane-1,3-[3H]indol]-2(1H)-one

Prepared according to the procedure for example 18: mp. 239–242° C.; $^1$H NMR (CDCl$_3$) δ1.64–1.82 (m, 6H), 1.88–2.04 (m, 2H), 7.00 (d, 1H, J=8 Hz), 7.29–7.31 (m, 1H), 7.36 (dd, 1H, J=8.8, 2 Hz), 7.54 (d, 1H, J=1.5 Hz), 7.73–7.78 (m, 2H) and 8.19 (s, 1H, br); MS ((+)-APCI) m/z 321 [M+H]$^+$.

EXAMPLE 55

5'-(3-Chlorophenyl)spiro[4,4-dimethylcyclohexane-1,3'-3H]indol]-2'(1'H)-one

A solution of 3,3-dimethylglutaric anhydride in dry THF (60 cm$^3$) was added over 30 min. to lithium aluminum hydride in dry THF (300 cm$^3$) under nitrogen at 0° C. The mixture was then brought gradually up-to reflux. After 3 h, the mixture was cooled, treated with water (3.3 cm$^3$), sodium hydroxide solution (15%, 3.3 cm$^3$) and water (9.9 cm$^3$). The mixture was then filtered, the precipitate extracted with EtOAc (×3), and the combined organics evaporated to afford 3,3-dimethyl-1,5-pentanediol (quantitative yield); $^1$H NMR (CDCl$_3$) δ0.95 (s, 6H), 1.57 (t, 4H, J=6.3 Hz), 3.75 (t, 4H,J=6.3 Hz).

A solution of 3,3-dimethyl-1,5-pentanediol (8.4 g, 63.5 mmol) in dry pyridine (180 cm$^3$) was cooled to 0° C. under nitrogen and treated over 5 h with a solution of p-toluenesulfonyl chloride (26.7 g, 140 mmol) in dry pyridine (100 cm$^3$). The mixture was then allowed to warm up to room temperature. After 16 h, the mixture was poured into ice/water and extracted with EtOAc (×3). The combined organics were washed with dil. HCl (30%), saturated sodium hydrogen carbonate, brine, dried (MgSO$_4$) and evaporated to afford 1,5-bis-(3,3-dimethylpentane)-p-toluenesulfonate (19.8 g, 45 mmol) which was used without further purification: $^1$H NMR (CDCl$_3$) δ inter alia 0.85 (s, 6H), 1.56. (t, 4H, J=7.0 Hz), 2.45 (s, 6H), 4.02 (t, 4H, J=7.0 Hz), 7.35 (d, 4H, J=8.0 Hz), 7.77 (d, 4H, J=8.0 Hz); MS ((+) APCI) m/z 441 (M+H)$^+$.

A solution of 1,5-bis-(3,3-dimethylpentane)-p-toluenesulfonate (53.0 g, 120 mmol) and sodium iodide (72.0 g, 480 mmol) was dissolved with stirring in dry acetone (500 cm$^3$). After 16 h at reflux the mixture was cooled, poured into water and extracted with diethylether (×3). The combined organic extracts were washed with water, dried (MgSO$_4$), and evaporated to afford 3,3-dimethyl-1,5-diiodopentane (41.3 g, 117 mmol) as a yellow oil that was used without further purification: $^1$H NMR (CDCl$_3$) δ inter alia 0.90 (s, 6H), 1.87–1.91 (m, 4H), 3.09–3.15 (m, 4H).

A solution of oxindole (2.0 g, 15 mmol) dissolved in dry THF (50 cm$^3$) under nitrogen was cooled to –60° C. and treated with n-butyllithium (2.5 M in hexanes, 15 cm$^3$, 37.5 mmol) followed by N,N,N'N'-tetramethylethylenediamine (5.66 g, 37.5 mmol). After 20 min. 3,3-dimethyl-1,5-diiodopentane (15.8 g, 45 mmol) in dry THF (10 cm$^3$) was added and the mixture was allowed to warm up to room temperature. After 16 h, the mixture was poured into water, extracted with EtOAc (×3), washed with water, dilute HCl (10%), water, brine, dried (MgSO$_4$) and evaporated. The residue was then subjected to column chromatography (SiO$_2$, EtOAc:hexane, 1:6) to afford spiro[4,4-dimethylcyclohexane-1',3'-[3H]indol]-2'(1'H)-one (0.37 g, 1.62 mmol, 11%): $^1$H NMR (CDCl$_3$) δ1.08 (s, 3H), 1.10 (s, 3H), 1.23–1.30 (m, 2H), 1.54–1.68 (m, 4H), 1.94–2.04 (m, 2H), 6.94 (d, 1H, J=7.7 Hz), 7.01 (t, 1H, J=7.6 Hz), 7.20 (t, 1H, J=7.7 Hz), 7.42 (d, 1H, J=7.4 Hz), 8.76 (s, 1H, br); MS (EI) m/z 229 (M)$^+$.

To a solution of the last cited compound (0.37 g, 1.62 mmol) and sodium acetate (0.14 g, 1.7 mmol) in acetic acid (5 cm$^3$) was added bromine (0.27 g, 1.7 mmol) in acetic acid (2 cm$^3$). After 30 min. the mixture was poured into sodium hydroxide solution (2N) and extracted with dichloromethane (×2). The organic extracts were washed with water, dried (MgSO$_4$) and evaporated to afford 5'-bromospiro[4,4-dimethylcyclohexane-1',3'-[3H]indol]-2'(1'H)-one (0.435 g, 1.41 mmol, 87%) which was used without further purification: $^1$H NMR (CDCl$_3$) δ1.08 (s, 3H), 1.49–1.64 (m, 4H), 1.69–1.74 (m, 2H), 1.89–1.98 (m, 2H), 6.77 (d, 1H, J=8.2 Hz), 7.33 (dd, 1H, J=8.2, 1.8 Hz), 7.48 (d, 1H, J=1.7 Hz), 7.71 (s, 1H, br); MS ((+)APCI) m/z 308 (M +H)$^+$.

The last cited compound (0.56 g, 1.81 mmol) and tetrakis (triphenylphosphine) palladium(0) (0.1 g, 0.08 mmol) were dissolved in dimethoxyethane (20 cm$^3$) under nitrogen. After 20 min. 3-chlorophenylboronic acid (0.57 g, 3.64 mmol) and sodium carbonate (0.97 g, 9.15 mmol) were added and the mixture heated under reflux. After 16 h the mixture was cooled, poured into water and extracted with EtOAc (×2). The combined organic layers were washed with sodium hydroxide (2N), water, brine, dried (MgSO$_4$) and evaporated. The residue was then subjected to column chromatography (SiO$_2$, EtOAc: hexanes, 1:5) to afford the title compound which was triturated with hexane to give a solid (0.26 g, 0.77 mmol, 43%): mp. 184–185° C.; $^1$H NMR (CDCl$_3$) δ1.11 (s, 6H), 1.57–1.80 (m, 6H), 1.45–2.03 (m, 2H), 6.98 (d, 1H, J=8.0 Hz), 7.29–7.44 (m, 4H), 5.52–7.55 (m, 2H), 8.12 (s, 1H, br); MS ((+)APCI) m/z 340 (M +H)$^+$.

EXAMPLE 56

5'-(3-Nitrophenyl)spiro[4,4-dimethylcyclohexane-1', 3'-[3H]indol]-2'(1'H)-one

To a solution of 5'-bromospiro[4,4-dimethylcyclohexane-1',3'-[3H]indol]-2'(1'H)-one (0.29 g, 0.95 mmol) in dimethoxyethane (15 cm$^3$) was added tetrakis (triphenylphosphine)palladium(0) (0.053 g, 0.046 mmol). After 20 min. 3-nitrophenylboronic acid (0.32 g, 1.9 mmol) and sodium carbonate (0.5 g, 4.75 mmol) in water (7.5 cm$^3$)

and the mixture heated under reflux. After 16 h, the mixture was cooled, poured into water and extracted with EtOAc (×2). The combined organic layers were washed with sodium hydroxide solution (2N), water, brine, dried (MgSO$_4$) and evaporated. The residue was then subjected to column chromatography (SiO$_2$, EtOAc: hexanes, gradient elution), then the product was triturated with hexane to afford the title compound (0.12 g, 0.35 mmol, 37%) as a yellow solid: mp. 230–231° C.; $^1$H NMR (CDCl$_3$) δ1.18–1.24 (m, 6H), 1.57–1.86 (m, 6H), 1.94–2.03 (m, 2H), 7.03 (d, 1H, J=8.0 Hz), 7.48 (d, 1H, J=8.0 Hz), 7.59–7.64 (m, 2H), 7.87 (d, 1H, J=7.7 Hz), 8.06 (s, 1H, br), 8.19 (d, 1H, J=7.7 Hz), 8.40 (s, 1H); MS ((+)APCI) m/z 351 (M+H)$^+$.

EXAMPLE 57

2,3,5,6-Tetrahydro-5-(3-nitrophenyl)spiro[3H-indole-3,4-[4H]pyran]-2(1H)-one

To a solution of sodium iodide (64 g, 0.43 mol) in acetone under N$_2$ was added 2-bromoethyl ether (20 g, 0.086 mol), causing a white solid to precipitate. After 16 h the mixture was filtered and the filtrate concentrated. Dichloromethane was added to the residue which was filtered, the cake further washed with dichloromethane, the combined organic layers were dried (MgSO$_4$) and evaporated to give 2-iodoethyl ether (26.61 g, 0.0816 mol, 95%) as a colorless oil: $^1$H NMR (CDCl$_3$) δ3.26 (t, 2H, J=7 Hz), 3.78 (t, 2H, J=7 Hz).

A solution of oxindole (5.00 g, 37.5 mmol) in anhydrous THF under N$_2$ was cooled to −20° C. n-butyllithium (2.5 M in hexanes, 30 cm$^3$, 75.1 mmol) was added drop-wise followed by N,N,N'N'-tetramethylethylenediamine (11.4 cm$^3$). After 20 min. a solution of 2-iodoethyl ether (36 g, 112 mmol) in anhydrous THF (20 cm$^3$) was added slowly. The mixture was allowed to warm to room temperature, then after 16 h was brought to reflux. After 5 h the mixture was cooled then poured into water, extracted with EtOAc (×2), the combined organic layers were washed with dil. HCl (pH 1), water (×2), dried (MgSO$_4$) and evaporated. The residue was purified by column chromatography (SiO$_2$, acetone: hexane 1:5) to afford the title compound (0.78 g, 3.82 mmol, 10%) as a white solid: $^1$H NMR (CDCl$_3$) δ1.84–1.95 (m, 4H), 3.91–3.96 (m, 2H), 4.21–4.27 (m, 2H), 6.89–6.92 (m, 1H), 7.06 (t, 1H, J=7, 1 Hz), 7.22 (t, 1H, J=7, 1 Hz), 7.35–7.38 (m, 1H).

A solution of the above product (0.78 g, 3.82 mmol) and sodium acetate (0.32 g, 4.02 mmol) in acetic acid (10 cm$^3$) was treated with bromine (0.64 g, 4.02 mmol) in acetic acid (2 cm$^3$). After 30 min. the mixture was poured into sat. sodium hydrogen carbonate solution and extracted with EtOAc (×2) washed with water, sat. sodium hydrogen carbonate solution, water, dried (MgSO$_4$), and evaporated to give the title compound (0.59 g, 2 mmol, 54%) as an off-white solid which was used without further purification: $^1$H NMR (CDCl$_3$) δ1.83–2.00 (m, 4H), 3.91–4.03 (m, 2H), 4.22–4.32 (m, 2H), 6.86 (d, 1H, J=7 Hz), 7.38–7.45 (m, 1H), 7.52 (d, 1H, J=1 Hz), 8.36 (s, 1H, br); MS ((+)ESI) m/z 282 (M+H)$^+$.

A solution of the above product (0.58 g, 2.04 mmol) and tetrakis(triphenylphosphine)palladium (0.11 g, 0.09 mmol) in dimethoxyethane (16 cm$^3$) was stirred under N$_2$ for 20 min. To this mixture was then added 3-nitrophenylboronic acid (0.63 g, 4.06 mmol) and potassium carbonate (1.68 g) in water (7 cm$^3$). After 3 h at reflux the mixture was cooled, poured into water and extracted EtOAc (×3). The combined organic extracts were washed with water, brine, dried (MgSO$_4$) and evaporated. The residue was then subjected to column chroratography (SiO$_2$, EtOAc: hexane, 1:2) to provide the title compound (0.19 g, 0.58 mmol, 28%). A sample which was further purified by preparative LC (Primesphere C18, 10 micron, 50×250 mm, MeCN: H$_2$O 46:54, 100 cm$^3$/min., RT 7.57 min.) had the following properties: mp >250° C., $^1$H NMR (acetone-d$_6$) δ1.78–1.88 (m, 2H), 1.92–2.01 (m, 2H), 3.85–3.94 (m, 2H), 4.12–4.23 (2H), 7.08–7.13 (m, 1H), 7.62–7.69 (m, 1H), 7.70–7.79 (m, 1H), 7.92–7.97 (m, 1H), 8.13–8.23 (m, 2H), 8.45–8.51 (m, 1H), 9.55 (s, 1H, br); MS (EI) m/z 341 (M)$^+$.

EXAMPLE 58

5'-(5-Chloro-3-methylbenzo[b]thien-2-yl)spiro [cyclo-hexane-1,3'-[3H]indol]-2'(1'H)-one A solution of the 2-bromo-5-chloro-3-methylbenzo[b]-thiophene (0.28 g, 1.1 mmol) and tetrakis-(triphenylphosphine) palladium (0.13 g, 0.1 mmol) in dimethoxyethane (8 cm3) was stirred under N$_2$ for 20 min. To this mixture was then added (2'-oxo-2,3-dihydrospiro [cyclohexane-1,3'-[3H]indol]-5'-yl) boronic acid (0.32 g, 1.3 mmol) and sodium carbonate (0.35 g, 3.3 mmol) in water (4 cm$^3$). The solution was brought to reflux for 12 h then cooled to RT, poured into water and extracted with EtOAc (3×50 cm$^3$). The combined organic extracts were washed with water, brine, dried (MgSO$_4$), and evaporated. The residue was purified by column chromatography (SiO$_2$, CH$_2$Cl$_2$) to afford the title compound (0.18 g, 0.47 mmol, 45%) as a white solid: mp. 256–258° C., $^1$H NMR (DMSO-d$_6$) δ1.47–1.97 (m, 10H), 2.42 (s, 3H), 6.99 (d, J=8.0 Hz, 1H), 7.39 (d, J=1.6 Hz, 1H), 7.42 (d, J=1.2 Hz, 1H), 7.6 (s, 1H), 7.85 (d, J=1.9 Hz, 1H), 7.99 (d, J=8.5 Hz, 1H), 10.53 (s, 1H); $^{13}$C NMR (DMSO-d$_6$) δ12.84 (q), 20.96, 25.08, 32.88 (t), 47.23 (s), 109.98, 121.99, 124.25, 124.71, 125.01 (d), 126.47, 126.59, 129.17, 130.01, 136.51, 140.42, 141.79, 142.76, 181.74 (s); MS (EI) m/z 380 (M−H)$^+$.

EXAMPLE 59

5-(3-Fluoro-4-nitrophenyl)spiro[cylohexane-1,3-[3H]indol]-2(1H)-one

The title compound was prepared from (2'-oxo-2,3-dihydrospiro[cyclohexane-1,3'-[3H]indol]-5'-yl)boronic acid (3.2 g, 12.5 mmol) and 4-bromo-2-fluoro-nitrobenzene (3 g, 13.6 mmol) as described for example 18 (0.7 g, 16%) as a yellow solid: mp. 213–215° C.; $^1$H NMR (DMSO-d$_6$) δ1.5–1.8 (m, 8H), 1.8–2.0 (m, 2H), 6.96 (d, 1H, J=8.13 Hz), 7.68 (dd, 1H, J=8.13, 1.76 Hz), 7.74 (dd, 1H, J=8.68, 1.76 Hz), 7.86 (d, 1H, J=1.98 Hz), 7.92 (dd, 1H, J=13.4, 1.76 Hz), 8.18 (t, 1H, J=8.46 Hz) and 10.52 (s, 1H); MS (EI) m/z=340 (M$^+$).

EXAMPLE 60

4-(1,2-Dihydro-2-oxospiro[cyclohexane-1,3-[3H]indol]-5-yl)-2 furancarbonitrile

A solution of 3-bromo-5-cyano-furan (0.75 g, 4.4 mmol), and tetrakis(triphenylphosphine)palladium(0) (0.4 g) in ethylene glycol dimethyl ether (20 cm$^3$) was stirred under N$_2$ for 20 minutes. To this mixture was then added (spiro [cyclohexane-1,3'-[3H]indol]-2'(1'H)-one-5-yl) boronic acid (1.6 g, 6.5 mmol) and sodium acetate (1.4 g, 13.1 mmol) in water (5 cm$^3$). The solution was brought to reflux for 18 hours and then cooled to room temperature, poured into 2N NaOH and extracted with EtOAc (×3). The combined extracts were washed with water, brine, dried (MgSO$_4$), and evaporated. The residue was purified by column chromatography (SiO$_2$, EtOAc, hexane) to afford the title compound (0.45 g, 36%) as an off-white solid. mp: 240–242° C.; $^1$H NMR (DMSO-d$_6$) δ10.4 (s, 1H), 8.5 (s, 1H), 8.2 (s, 1H), 7.7 (s, 1H), 7.5 (dd, 1H, J=1.5 6.5 Hz), 6.9 (d, 1H, J=8.0 Hz), 2.0–1.6 (m, 10H); MS (EI) M$^+$ @ m/z 292.

EXAMPLE 61

5-[4Fluoro-3-(trifluoromethyl)phenyl]spiro [cyclohexane-1,3-[3H]indol]-2(1H)-one The title compound was prepared from (2'-oxo-2,3-dihydrospiro[cyclohexane-1,3'-[3H]indol]-5'-yl)boronic acid (2.5 g, 10 mmol) and 5-bromo-2-fluoro-trifluoromethylbenzene (2 g, 8 mmol) as described for example 18, to afford the title compound (0.87 g, 30%) as a solid: mp: 222° C.; $^1$H NMR (DMSO-d$_6$) δ1.5–1.8 (m, 8H), 1.8–2.0 (m, 2H), 6.92 (d, 1H, J=8.13 Hz), 7.51 (dd, 1H, J=8.13, 1.76 Hz), 7.55 (dd, 1H, J=10.54, 9.01 Hz) 7.72 (d, 1H, J=1.76 Hz), 7.90 (dd, 1H, J=7.03, 2.20 Hz), 7.98 (m, 1H) and 10.39 (s, 1H); MS (EI) m/z 363 (M$^+$).

EXAMPLE 62

5-[4-Fluoro-3-nitrophenyl]spiro[cyclohexane-1,3-[3H]indol]-2(1H)-one

The title compound was prepared from (2'-oxo-2,3-dihydrospiro[cyclohexane-1,3'-[3H]indol]-5'-yl)boromic acid (2.8 g, 11 mmol) and 5-bromo-2-fluoro-nitrobenzene (2.7 g, 12.2 mmol) as described for example 18, to afford the title compound (2.5 g, 66%) as a solid: mp. 243–245° C.; $^1$H NMR (DMSO-d$_6$) δ1.8–2.0 (m, 2H), 1.5–1.8 (m, 8H), 6.94 (d, 1H, J=8.13 Hz), 7.55 (dd, 1H, J=8.01, 1.87 Hz), 7.63 (dd, J=10.98, 8.79 Hz), 8.07 (m, 1H), 8.30 (dd, 1H, J=7.14, 2.53 Hz) and 10.43 (s, 1H); MS (ESI (neg)) m/z 339 (M–H)$^-$.

EXAMPLE 63

5'-(4-Cyano-3-fluorophenyl)-spiro[cyclohexane-1,3'-[3H]indol]-2'(1'H)-one

A solution of 4-cyano-3-fluoro-bromobenzene (0.76 g, 3.8 mmol), and tetrakis(triphenylphosphine)palladium(0) (0.3 g) in ethylene glycol dimethyl ether (15 cm$^3$) was stirred under N$_2$ for 20 minutes. To this mixture was then added (spiro[cyclohexane-1,3'-[3H]indol]-2'(1'H)-one-5-yl) boronic acid (1.4 g, 5.7 mmol) and sodium acetate (1.2 g, 11.4 mmol) in water (5 cm$^3$). The solution was brought to reflux for 18 hours and then cooled to room temperature, poured into 2N NaOH and extracted with EtOAc (×3). The combined extracts were washed with water, brine, dried (MgSO$_4$), and evaporated. The residue was purified by column chromatography (SiO$_2$, EtOAc, hexane) to afford the title compound (0.45 g, 37%) as an off-white solid. mp: 258–260° C.; $^1$H NMR (DMSO-d$_6$) δ8.8 (s, 1H), 7.7–7.6 (m, 2H), 7.5 (td, 2H, J=0.9. 1.5, 5.7 Hz), 7.4 (dd, 1H, J=1.5, 8.8 Hz), 7.0 (d, 1H, J=8.1 Hz), 2.0–1.6 (m, 10H); MS (–)APCI [M–H]$^-$ @ m/z 319.

EXAMPLE 64

2-fluoro-4-(1',2'-Dihydro-2'-oxospiro[cyclohexane-1,3'-[3H]indol-5'-yl) benzaldehyde oxime A solution of 3-fluoro-4-bromobenzaldehyde oxime (0.5 g, 2.2 mmol), and tetrakis(triphenylphosphine)palladium(0) (0.2 g) in ethylene glycol dimethyl ether (10 cm$^3$) was stirred under N$_2$ for 20 minutes. To this mixture was then added (spiro[cyclohexane-1,3'-[3H]indol]-2'(1'H)-one-5-yl) boronic acid (0.8 g, 3.3 mmol) and sodium acetate (0.7 g, 6.5 mmol) in water (5 cm$^3$). The solution was brought to reflux for 18 hours and then cooled to room temperature, poured into 2N NaOH and extracted with EtOAc (×3). The combined extracts were washed with water, brine, dried (MgSO$_4$), and evaporated. The residue was purified by column chromatography (SiO$_2$, EtOAc, hexane) to afford the title compound (0.25 g, 34%) as an off-white solid. mp: 240–242° C.; $^1$H NMR (DMSO-d$_6$) δ11.6 (s, 1H), 10.4 (s, 1H), 8.2 (s, 1H), 7.8–7.7 (m, 2H), 7.6–7.5 (m, 3H), 6.9 (d, 1H, J=8.1 Hz), 2.0–1.6 (m, 10H); MS (EI) M$^+$ @ m/z 338.

EXAMPLE 65

5-(2'-oxo-2',3'-dihydrospiro[cyclopentane-1,3'-[3H] indol]-5'yl-2-nitrothiophene A solution of 2-bromo-5-nitrothiophene (0.6 g, 2.9 mmol), and tetrakis(triphenylphosphine)palladium(0) (0.2 g) in ethylene glycol dimethyl ether (20 cm$^3$) was stirred under N$_2$ for 20 minutes. To this mixture was then added (spiro[cyclopentane-1,3'-[3H]indol]-2'(1'H)-one-5-yl) boronic acid (1.0 g, 4.3 mmol) and sodium acetate (1.0 g, 10.0 mmol) in water (5 cm$^3$). The solution was brought to reflux for 18 hours and then cooled to room temperature, poured into 2N NaOH and extracted with EtOAc (×3). The combined extracts were washed with water, brine, dried (MgSO$_4$), and evaporated. The residue was purified by column chromatography (SiO$_2$, EtOAc, hexane) to afford the title compound (0.87 g, 96%) as a yellow solid. mp: 264–266° C.; $^1$H NMR (DMSO-d$_6$) δ10.6 (s, 1H), 8.1 (d, 1H, J=4.5 Hz), 7.7 (d, 1H, J=1.8 Hz) 7.6 (m, 2H), 6.9 (d, 1H, J=8.1 Hz), 2.0–1.9 (m, 8H); MS (EI) M$^+$ @ m/z 314.

EXAMPLE 66

5-(3-Chloro-4-fluoro-phenyl)-3,3-dimethyl1,3-dihydro-indol-2-one

A solution of 5-bromo-3,3-dimethyl-1,3-dihydro-indol-2-one (0.35 g, 1.46 mmol) and tetrakis(triphenylphosphine) palladium (0.13 g, 0.11 mmol) in dimethoxyethane (10 cm3) was stirred under N$_2$ for 20 min. To this mixture was then added 3-chloro-4-fluorobenzene boronic acid (0.26 g, 1.49 mmol) and potassium carbonate (0.62 g, 4.5 mmol) in water (5 cm3). The solution was brought to reflux for 16 h then cooled to RT, poured into saturated ammonium chloride and extracted with EtOAc (×3). The combined organic extracts were dried (MgSO$_4$), and evaporated. The residue was purified by column chromatography (SiO$_2$, ethyl acetate: hexane 1:3) to afford the title compound (0.124 g, 0.43 mmol, 30%) as a white solid: mp. 206.5–207.8° C., $^1$H NMR (DMSO-d$_6$) δ1.3 (s, 6H), 6.93 (d, J=8.1 Hz, 1H), 7.45 (dd, J=8.9, 8.9 Hz, 1H), 7.5 (dd, J=8.1, 1.8 Hz, 1H), 7.6 (ddd, J=8.9, 7.1, 2.2 Hz, 1H), 7.7 (d, J=1.8 Hz, 1H), 7.8 (dd, J=7.1, 2.2 Hz, 1H), 10.5 (s, 1H); MS (EI) m/z 289/291 (M)$^+$.

EXAMPLE 67

3-(3,3-Dimethyl-2-oxo-2,3-dihydro-1H-indol-5-yl)-benzonitrile (2'-oxo-[2,3-dihydro-3,3-dimethyl-1,3'-[3H]indol]-5'-yl) boronic acid To a solution of 5'-bromo-3,3-dimethyl-[1,3'-[3H]indol]-2'-(1'H)-one (3.5 g, 14.6 mmol) in dry tetrahydrofuran (60 cm$^3$) was added of sodium hydride (60% dispersion in mineral oil, 0.59 g, 14.6 mmol). After 30 min. stirring at room temperature, the mixture was cooled to −78° C. and n-butyl lithium (2.5 M in hexanes, 5.9 cm$^3$, 14.6 mmol) was added slowly. After 30 min. tri-isopropyl borate (9 cm$^3$, 38.9 mmol) was added and the mixture was allowed to warm to room temperature. After 8 hrs. hydrochloric acid (1N, 200 cm$^3$) and ethylacetate (200 cm$^3$)was added and the mixture stirred for 20 min. The aqueous phase was extracted with ethylacetate, then the combined organic layers were washed with water, brine, dried (Na$_2$SO$_4$) and evaporated. The residue was triturated with hexane and the precipitate dried in vacuo to obtain (2'-oxo-[2,3-dihydro-3,3-dimethyl -1,3'-[3H]indol]-5'-yl) boronic acid (1.8 g, 8.8 mmol, 60%) as a yellow-white solid that was used without further purification. $^1$H NMR (DMSO-d$_6$) δ1.23 (s, 6H), 6.81 (d, J=7.8 Hz, 1H) 7.63 (d, J=7.8 Hz, 1H) 7.66 (s, 1H), 7.84 (s, 2H) 8.69 (s, 1H).

A solution of 3-bromobenzonitrile (0.30 g, 1.65 mmol) and tetrakis(triphenylphosphine) palladium (0.13 g, 0.1 mmol) in dimethoxyethane (10 cm3) was stirred under N$_2$ for 20 min. To this mixture was then added the (2'-oxo-[2, 3-dihydro-3,3-dimethyl -1,3'-[3H]indol]-5'-yl) boronic acid, (0.41 g, 2.0 mmol) and potassium carbonate (0.86 g, 6.2 mmol) in water (5 cm3). The solution was brought to reflux for 16 h then cooled to room temperature, poured into saturated ammonium chloride and extracted with EtOAc (×3). The combined organic extracts were dried (MgSO$_4$), and evaporated. The residue was purified by column chromatography (SiO$_2$, ethyl acetate: hexane 1:2.5) to afford the title compound (0.22 g, 0.68 mmol, 51%) as a white solid: mp. 200.2–202.0° C., $^1$H NMR (DMSO-d$_6$) δ1.32 (s, 6H), 6.96 (d, J=8.1 Hz, 1H), 7.58 (dd, J=8.1, 1.8, 1H), 7.63 (dd, J=7.8, 7.8 Hz, 1H), 7.75–7.78 (m, 2H), 7.98 (d, J=8.0 Hz, 1H), 8.15 (s, 1H), 10.49 (s, 1H); MS (EI) m/z 263 (M+H)+.

EXAMPLE 68

2-fluoro-3-(1',2'-Dihydro-2'-oxospiro[cyclohexane-1, 3'-[3H]indol-5'-yl)benzaldehyde oxime A solution of 3-bromo-2-fluorobenzoic acid (0.219 g, 1 mmol) in dry methanol (5 ml) under nitrogen was treated with trimethylorthoformate (0.22 ml, 2 mmol) and p-toluenesulfonic acid (catalytic amount), and then heated under reflux. After 16 h, the mixture was evaporated and the residue partitioned between water and Et$_2$O. The organic layer was washed with sat. sodium hydrogen carbonate solution, water, brine, dried (MgSO$_4$) and evaporated to give methyl 3-bromo-2-fluorobenzoate (0.195 g, 0.84 mmol, 84%): $^1$H NMR (CDCl$_3$) δ7.90–7.85 (m, 1H), 7.71–7.65 (m, 1H), 7.10 (dt, 1H, J=8.0, 1.0 Hz) and 3.94 (s, 3H): MS (EI) 232 (M$^+$).

A solution of the last cited compound (3.077 g, 13.2 mmol) in dry toluene (80 ml) at −78° C. under nitrogen was treated with di-iso-butylaluminum hydride in toluene (1M, 15.7 ml, 15.7 mmol). After 1 h at −78° C., the mixture was quenched with aqueous HCl (3M, 16 ml). The mixture was warmed to room temperature (RT), partitioned between EtOAc/H$_2$O, the aqueous layer was re-extracted with EtOAc, and the combined organic layers were washed with water, dried (MgSO$_4$) and evaporated to afford 3-bromo-2-fluorobenzaldehyde (2.63 g, 12.9 mmol, 98%), which was used without further purification: $^1$H NMR (CDCl$_3$) δ10.35 (s, 1H), 7.82 (m, 2H), 7.18 (t, 7.8 Hz).

A mixture of the last cited compound (2.63 g, 12.9 mmol), hydroxylamine hydrochloride (1.0 g, 14 mmol) and potassium acetate (1.37 g, 14 mmol) was placed in ethanol/H$_2$O (60 ml, 8:2) and the mixture was heated under reflux. After 30 min. the mixture was cooled, evaporated and partitioned between EtOAc and water. The organic layer was washed with brine, dried (MgSO$_4$) and evaporated to give afford 3-bromo-2-fluorobenzaldoxime which was used without further characterization.

The title compound was prepared from 3-bromo-2-fluorobenzaldoxime (0.40 g, 1.83 mmol) and (spiro [cyclohexane-1,3'-[3H]indol]-2'(1'H)-one-5-yl) boronic acid as described in example 18, to afford the product (0.094 g, 0.27 mmol, 15% yield) as a white solid: mp. 213–217° C.; $^1$H NMR (CDCl$_3$) δ10.95 (s, 1H), 9.65 (s, 1H), 8.41 (s, 1H), 7.76 (t, 1H, J=7.1 Hz), 7.59 (s, 1H), 7.43–7.33 (m, 3H), 7.19 (t, 1H, J=7.7 Hz), 6.98 (d, 1H, J=8 Hz) and 1.91–1.60 (m, 10H); MS ((+) ESI) m/z=339 [M+H]$^+$.

EXAMPLE 69

5(3,3-Dimethyl-2-oxo-2,3dihydro-1H-indol-5-yl)-4methyl thiophene-2-carbonitrile

5-Bromo-4-methyl-2-thiophene carboxaldehyde

To a solution of diethylamine (28 g, 0.383 mol) in anhydrous THF (400 mL) was added at −40° C. under nitrogen a solution of n-BuLi (2.5 M, 153 mL, 0.383 mol) in hexane. After addition, the solution was stirred at −40° C. under nitrogen for 30 minutes, cooled to −78° C. and treated dropwise with a solution of 2-bromo-3-methylthiophene (45 g, 0.254 mol) in anhydrous THF (450 mL). The reaction solution was stirred at −78° C. for 30 minutes and treated with anhydrous DMF (100 mL). The mixture was allowed to warm to ambient temperature and was quenched with 1N aqueous hydrochloride solution (1L). The solution was extracted with ethyl acetate(3×450 mL). The extracts were washed with water, brine and dried (MgSO$_4$). After removal of solvent in vacuo, the subtitled compound was obtained as a white solid (46 g, 88.3%). A sample of the product was crystallized from hexane: mp 63–65° C.; IR (KBr) 1654 cm$^{-1}$. $^1$H-NMR (CDCl$_3$) δ9.75 (s, 1H), 7.45 (s, 1H), 2.26 (s, 3H); MS (EI) m/z 204/206 (M$^+$). Anal. Calc. For C$_6$H$_5$BrOS: C, 35.14; H, 2.46. Found: C, 35.00; H, 2.44.

5-Bromo-4-methyl-2-thiophenecarbonitrile

Prepared from 5-bromo-4-methyl-2-thiophene carboxaldehyde using the procedure of Example 35. White solid: mp 40–42° C.; IR (KBr) 2200 cm$^{-1}$; $^1$H-NMR (CDCl$_3$) δ7.29 (s, 1H), 2.21 (s, 3H). MS (EI) m/z 201/203 (M$^+$, 98%/100%); Anal. Calc. For C$_6$H$_4$BrNS: C, 35.66; H, 1.99; N, 6.93. Found: C, 36.00; H, 2.14; N, 6.76.

Prepared according to the procedure for example 18 using (2'-oxo-[2, 3-dihydro-3,3-dimethyl -1,3'-[3H]indol]-5'-yl) boronic acid (357 mg, 1.7 mmol) and 5-bromo-4-methylthiophene-2-carbonitrile (295 mg, 1.5 mmol) to afford the title compound (227 mg, 0.8 mmol, 55%) as a white solid: mp. 192.3–193° C., $^1$H NMR (DMSO-d$_6$) δ1.29 (s, 6H), 2.29 (s, 3H), 6.97 (d, J=8.0 Hz, 1H), 7.34 (dd, J=8.0, 1.8 Hz, 1H), 7.49 (d, J=1.7 Hz, 1H), 7.84 (s, 1H), 10.57 (s, 1H); MS (EI) m/z 282 (m)$^+$.

EXAMPLE 70

5-(3-Chloro-5-fluoro-phenyl)-3,3-dimethyl-1,3-dihydro-indol-2-one

Prepared according to the procedure for example 18 for using (2'-oxo-[2,3-dihydro-3,3-dimethyl -1,3'-[3H]indol]-5'-yl) boronic acid (345 mg, 1.7 mmol) and 1-bromo-3-chloro-5-fluorobenzene (295 mg, 1.4 mmol) to afford the title compound (245 mg, 0.85 mmol, 60%) as a white solid: mp. 205.9–206.8° C. $^1$H NMR (DMSO-d$_6$) δ1.31 (s, 6H), 6.93 (d, J=8.1Hz), 7.35 (d, J=8.6 Hz, 1H), 7.5–7.6 (m, 2H), 7.6 (s, 1H), 7.78 (d, J=1.4 Hz, 1H), 10.49 (s, 1H); MS (EI) m/z 290 (M+H)$^+$.

EXAMPLE 71

5-(3-Fluoro-5-nitro-phenyl)-3,3-dimethyl-1,3-dihydro-indol-2-one

Prepared according to the procedure for example 18 using (2'-oxo-[2,3-dihydro-3,3-dimethyl -1,3'-[3H]indol]-5'-yl)

boronic acid (272 mg, 1.3 mmol) and 1-fluoro-3-iodo-5-nitrobenzene (299 mg, 1.1 mmol) to afford the title compound (192 mg, 0.64 mmol, 57%) as a yellow solid: mp. 231.2–232.7° C., $^1$H NMR (DMSO-d$_6$) δ1.33 (s, 6H), 6.97 (d, J=8.1 Hz, 1H), 7.67 (dd, J=8.1, 1.7 Hz, 1H), 7.88 (d, J=1.6 Hz, 1H), 8.0–8.1 (m, 2H), 8.32 (s,1H), 10.55 (s, 1H);MS (ESI) m/z 301 (M+H)$^+$.

EXAMPLE 72

4-(3,3-Dimethyl-2-oxo-2,3-dihydro-1H-indol-5-yl)-furan-2-carbonitrile

Prepared according to the procedure for example 18 using (2'-oxo-[2,3-dihydro-3,3-dimethyl -1,3'-[3H]indol]-5'-yl) boronic acid (354 mg, 1.7 mmol) and 4-bromo-furan-2-carbonitrile (200 mg, 1.2 mmol) to afford the title compound (76 mg, 0.3 mmol, 26%) as a white solid: mp. 199.6–201.4° C., $^1$H NMR (DMSO-d$_6$) δ1.28 (s, 6H), 6.89 (d, J=8.0 Hz, 1H), 7.48 (dd, J=8.0, 1.8 Hz, 1H), 7.65 (d, J=1.5 Hz, 1H), 8.1 (s, 1H), 8.5 (s, 1H), 10.46 (s, 1H); MS (ESI) m/z 251 (M–H)$^-$.

EXAMPLE 73

4-Methyl-5-(2'-oxo-2',3'-dihydrospiro[cyclopentane-1,3'-[3H]indol-5'-yl)-2-thiophene carbonitrile (Spiro[cyclopentane-1,3'-[3H]indol]-2'(1'H)-one-5-yl) boronic acid To a solution of 5-bromo-spiro[cyclopentane-1,3'-[3H]indol]-2'(1'H)-one (13.1 g, 53 mmol) in anhydrous THF (300 cm$^3$) under N$_2$, was added sodium hydride (60% in mineral oil, 2.1 g, 53 mmol). After 30 minutes, the reaction mixture was cooled to −78° C. and butyl lithium (2.5 M in hexanes, 22 cm$^3$, 53 mmol) was added slowly. After 30 minutes, tris-iso-propylborate (34 cm$^3$, 146 mmol) was added, and the reaction mixture was slowly brought to room temperature, and stirred for 14 hours. The reaction mixture was poured into 1N HCl and extracted with EtOAc (×3). The organic layers were collected and washed with 1N HCl, water, dried (MgSO$_4$) and evaporated to give the subtitled compound (7.8 g, 64%) as a tan solid which was used without further purification. $^1$H NMR (DMSO-d$_6$) δ10.3 (s, 1H), 7.9 (s, 1H), 7.7–7.6 (m, 2H), 6.8 (d, 1H, J=7.7 Hz), 3.4 (s, 1H), 2.0–1.7 (m, 8H); MS (FI-POS) m/z @ 231.

A solution of 2-bromo-5-cyano-3-methylthiophene (0.63 g, 3.1 mmol), and tetrakis(triphenylphosphine)palladium(0) (0.2 g) in ethylene glycol dimethyl ether (20 cm$^3$) was stirred under N$_2$ for 20 minutes. To this mixture was added (spiro[cyclopentane-1,3'-[3H]indol]-2'(1'H)-one-5-yl) boronic acid (1.0 g, 4.7 mmol) and sodium carbonate (1.0 g, 9.4 mmol) in water (5 cm$^3$). The solution was brought to reflux for 18 hours and then cooled to room temperature, poured into 2N NaOH and extracted with EtOAc (×3). The combined extracts were washed with water, brine, dried (MgSO$_4$), and evaporated. The residue was purified by column chromatography (SiO$_2$, EtOAc, hexane) to afford the title compound (0.6 g, 62%) as a pale-yellow solid. mp: 135–136° C.; $^1$H NMR (DMSO-d$_6$) δ10.5 (s, 1H), 7.8 (s, 1H), 7.4–7.3 (m, 2H), 7.0 (d, 1H, J=8.0 Hz), 2.3 (s, 3H), 2.0–1.8 (m, 8H); MS [M–H]$^-$=307.

EXAMPLE 74

5'-(4-Cyano-3-fluorophenyl)-spiro[cyclopentane-1,3'-[3H]indol]-2'(1'H)-one

A solution of 4-cyano-3-fluoro-bromobenzene (0.63 g, 3.1 mmol), and tetrakis(triphenylphosphine)palladium(0) (0.2 g) in ethylene glycol dimethyl ether (20 cm$^3$) was stirred under N$_2$ for 20 minutes. To this mixture was then added (spiro[cyclopentane-1,3'-[3H]indol]-2'(1'H)-one-5-yl) boronic acid (1.0 g, 4.7 mmol) and sodium carbonate (1.0 g, 9.4 mmol) in water (5 cm$^3$). The solution was brought to reflux for 18 hours and then cooled to room temperature, poured into 2N NaOH and extracted with EtOAc (×3). The combined extracts were washed with water, brine, dried (MgSO$_4$), and evaporated. The residue was purified by column chromatography (SiO$_2$, EtOAc, hexane) to afford the title compound (0.35 g, 36%) as a yellow solid. mp: dec. @ 235° C.; $^1$H NMR (DMSO-d$_6$) δ10.5 (s, 1H), 7.9 (t, 1H, J=7.6 Hz), 7.9 (dd, 1H, J=1.4, 10.2 Hz), 7.3 (td, 2H, J=1.6, 6.5 Hz), 7.6 (dd, 1H, J=1.9, 6.3 Hz), 6.9 (d, 1H, J=8.1 Hz), 2.0–1.9 (m, 8H); MS [M–H]$^-$=305.

EXAMPLE 75

5'-(3-cyano-4-fluorophenyl)-spiro[cyclopentane-1,3'-[3H]indol]-2'(1'H)-one

A solution of 3-cyano-4-fluoro-bromobenzene (0.63 g, 3.1 mmol), and tetrakis(triphenylphosphine)palladium(0) (0.2 g) in ethylene glycol dimethyl ether (20 cm$^3$) was stirred under N$_2$ for 20 minutes. To this mixture was then added (spiro[cyclopentane-1,3'-[3H]indol]-2'(1'H)-one-5-yl) boronic acid (1.0 g, 4.7 mmol) and sodium acetate (1.0 g, 9.4 mmol) in water (5 cm$^3$). The solution was brought to reflux for 18 hours and then cooled to room temperature, poured into 2N NaOH and extracted with EtOAc (×3). The combined extracts were washed with water, brine, dried (MgSO$_4$), and evaporated. The residue was purified by column chromatography (SiO$_2$, EtOAc, hexane) to afford the title compound (0.10 g, 10%) as white crystals. mp: 264–266° C.; $^1$H NMR (DMSO-d$_6$) δ10.4 (s, 1H), 8.3 (dd, 1H, J=2.4, 3.7 Hz), 8.1–8.0 (m, 1H), 7.6–7.5 (m, 2H), 7.5 (dd, 1H, J=1.9, 6.3 Hz), 6.9 (d, 1H, J=8.1 Hz), 2.0–1.9 (m, 8H); MS [M–H]$^-$=305.

EXAMPLE 76

5'-(3-Chloro-4fluorophenyl)-spiro[cyclopentane-1,3'-[3H]indol]-2'(1'H)-one

A solution of 3-chloro-4-fluoro-bromobenzene (0.4 cm$^3$, 0.66 g, 3.1 mmol), and tetrakis(triphenylphosphine)palladium(0) (0.2 g) in ethylene glycol dimethyl ether (20 cm$^3$) was stirred under N$_2$ for 20 minutes. To this mixture was then added (spiro[cyclopentane-1,3'-[3H]indol]-2'(1'H)-one-5-yl) boronic acid (1.0 g, 4.7 mmol) and sodium carbonate (1.0 g, 9.4 mmol) in water (5 cm$^3$). The solution was brought to reflux for 18 hours and then cooled to room temperature, poured into 2N NaOH and extracted with EtOAc (×3). The combined extracts were washed with water, brine, dried (MgSO$_4$), and evaporated. The residue was purified by column chromatography (SiO$_2$, EtOAc, hexane) to afford the title compound (0.65 g, 66%) as a pale-yellow solid. mp: 202–204° C.; $^1$H NMR (DMSO-d$_6$) δ10.4 (s, 1H), 7.9 (dd, 1H, J=2.3, 4.9 Hz), 7.7–7.6 (m, 1H), 7.6 (d, 1H, J=1.5 Hz), 7.5 (s, 1H) 7.4 (d, 1H, J=1.8 Hz), 6.9 (d, 1H, J=8.0 Hz), 2.0–1.9 (m, 8H); MS [M–H]$^-$=314.

EXAMPLE 77

5'-(3-Cyanophenyl)-spiro[cyclopentane-1,3'-[3H]indol]-2'(1'H)-one

A solution of 3-bromobenzonitrile (0.5 g, 2.6 mmol), and tetrakis(triphenylphosphine)palladium(0) (0.2 g) in ethylene glycol dimethyl ether (20 cm³) was stirred under N₂ for 20 minutes. To this mixture was then added (spiro [cyclopentane-1,3'-[3H]indol]-2'(1'H)-one-5-yl) boronic acid (0.9 g, 3.9 mmol) and sodium carbonate (0.8 g, 7.8 mmol) in water (5 cm³). The solution was brought to reflux for 18 hours and then cooled to room temperature, poured into 2N NaOH and extracted with EtOAc (×3). The combined extracts were washed with water, brine, dried (MgSO₄), and evaporated. The residue was purified by column chromatography (SiO₂, EtOAc, hexane) to afford the title compound (0.30 g, 40%) as an off-white solid. mp: 217–219° C.; ¹H NMR (DMSO-d₆) δ10.4 (s, 1H), 8.2 (s, 1H), 8.0 (d, 1H, J=8.1 Hz), 7.8 (d, 1H, J=7.7 Hz), 7.6 (m, 2H), 7.5 (dd, 1H, J=1.8, 6.3 Hz), 6.9 (d, 1H, J=8.1 Hz), 2.0–1.9 (m, 8H); MS [M−H]⁻=287.

EXAMPLE 78

5-(1,2-Dihydro-2-oxospiro[cyclopentane-1,3-[3H] indol]-5-yl)-2-thiophenecarbonitrile A solution of 2-bromo-5-cyanothiophene (0.5 g, 2.6 mmol), and tetrakis(triphenylphosphine)palladium(0) (0.2 g) in ethylene glycol dimethyl ether (20 cm³) was stirred under N₂ for 20 minutes. To this mixture was then added (spiro[cyclopentane-1,3'-[3H]indol]-2'(1'H)-one-5-yl) boronic acid (0.9 g, 3.9 mmol) and sodium carbonate (0.8 g, 7.8 mmol) in water (5 cm³). The solution was brought to reflux for 18 hours and then cooled to room temperature, poured into 2N NaOH and extracted with EtOAc (×3). The combined extracts were washed with water, brine, dried (MgSO₄), and evaporated. The residue was purified by column chromatography (SiO₂, EtOAc, hexane) to afford the title compound (0.3 g, 40%) as a yellow solid. mp: 248° C.; ¹H NMR (DMSO-d₆) δ10.4 (s, 1H), 8.5 (d, 1H, J=1.4 Hz), 8.3 (d, 1H, J=1.4 Hz), 7.6 (s, 1H), 7.5 (dd, 1H, J=1.7, 6.4 Hz), 6.9 (d, 1H, J=8.1 Hz), 2.0–1.8 (m, 8H); MS [M−H]⁻=293.

EXAMPLE 79

5-(3,3-Dimethyl-2-oxo-2,3-dihydro-1H-indol-5-yl)-furan-2-carbonitrile

A solution of 5-cyano-2-bromofuran (0.5 g, 2.6 mmol), and tetrakis(triphenylphosphine)palladium(0) (0.2 g) in ethylene glycol dimethyl ether (20 cm³) was stirred under N₂ for 20 minutes. To this mixture was then added (spiro [cyclopentane-1,3'-[3H]indol]-2'(1'H)-one-5-yl) boronic acid (0.9 g, 3.9 mmol) and sodium carbonate (0.8 g, 7.8 mmol) in water (5 cm³). The solution was brought to reflux for 18 hours and then cooled to room temperature, poured into 2N NaOH and extracted with EtOAc (×3). The combined extracts were washed with water, brine, dried (MgSO₄), and evaporated. The residue was purified by column chromatography (SiO₂, EtOAc, hexane) to afford the title compound (0.35 g, 49%) as an off-white solid. mp: 193–194° C.; ¹H NMR (DMSO-d₆) δ10.6 (s, 1H), 7.7 (d, 2H, J=3.3 Hz), 7.6 (dd, 1H, J=1.6, 6.6 Hz), 7.1 (d, 1H, J=3.8 Hz), 6.9 (d, 1H, J=8.1 Hz), 2.0–1.8 (m, 8H); MS [M−H]⁻=277.

EXAMPLE 80

5'-(3-Cyano-5-fluorophenyl)-spiro[cyclopentane-1, 3'-[3H]indol]-2'(1'H)-one

A solution of 3-cyano-5-fluoro-bromobenzene (0.5 g, 2.6 mmol), and tetrakis(triphenylphosphine)palladium(0) (0.2 g) in ethylene glycol dimethyl ether (20 cm³) was stirred under N₂ for 20 minutes. To this mixture was then added (spiro[cyclopentane-1,3'-[3H]indol]-2'(1'H)-one-5-yl) boronic acid (0.9 g, 3.9 mmol) and sodium carbonate (0.8 g, 7.8 mmol) in water (5 cm³). The solution was brought to reflux for 18 hours and then cooled to room temperature, poured into 2N NaOH and extracted with EtOAc (×3). The combined extracts were washed with water, brine, dried (MgSO₄), and evaporated. The residue was purified by column chromatography (SiO₂, EtOAc, hexane) to afford the title compound (0.35 g, 44%) as white needles. mp: 235–237° C.; ¹H NMR (DMSO-d₆) δ10.5 (s, 1H), 8.1 (s, 1H), 8.0 (dt, 1H, J=1.7, 2.0, 7.0 Hz), 7.8–7.7 (m, 2H), 7.6 (dd, 1H, J=1.8, 6.4 Hz), 6.9 (d, 1H, J=8.1 Hz), 2.0–1.9 (m, 8H); MS (EI) M⁺ @ m/z 306.

EXAMPLE 81

3-(1',2'-Dihydro-2'-oxospiro[cyclohexane-1,3'-[3H] indol-5'-yl)phenylacetonitrile Prepared from 3-bromophenylacetonitrile and 2'-oxo-2', 3,-dihydrospiro[cyclohexane-1,3'-[3H]indol]-5'-yl)boronic acid according to the procedure for example 18 to afford the title compound as a white powder; mp. 190–193° C.; ¹H-NMR (DMSO-d₆) δ10.42 (s, 1H), 7.67 (d, 1H, J=1.39 Hz), 7.58 (d, 2H J=6.87 Hz), 7.46 (m, 2H), 7.31 (d, 1H J=7.6 Hz), 6.94 (d, 1H, J=8.05) 4.10 (s, 2H) 2.04–1.50 (m, 10H); MS m/z 316 (M+.). Anal. Calc. For C₂₁H₂₀N₂O₂ 0.2H2O: C, 78.82, H, 6.42, N, 8.75. Found: C, 78.73, H, 6.44, N, 8.52.

EXAMPLE 82

3-(3,3-Dimethyl-2-oxo-2,3-dihydro-1H-indol-5-yl)-fluoro-benzonitrile

Prepared according to the procedure for example 18 using (2'-oxo-[2,3-dihydro-3,3-dimethyl-1,3'-[3H]indol]-5'-yl) boronic acid (640 mg, 3.1 mmol) and 5-bromo-3-cyano-fluorobenzene (423 mg, 21.2 mmol) to afford the title compound (261 mg, 0.93 mmol, 44%) as a yellow solid: mp. 231.2–232.3° C., ¹H NMR (DMSO-d₆) δ1.32 (s, 6H), 6.95 (d, J=8.0 Hz, 1H), 7.64 (dd, J=8.1, 1.8 Hz, 1H), 7.76 (d, J=8.4 Hz, 1H), 7.85 (d, J=1.6 Hz, 1H), 7.93 (d, J=8.6 Hz, 1H), 8.07 (s, 1H), 10.52 (s, 1H); MS (EI) m/z 280 (M)⁺.

EXAMPLE 83

3,3-Dimethyl-5-(5-nitro-thiophene-2-yl)-1,3-dihydro-indol-2-one

Prepared according to the procedure for example 18 using (2'-oxo-[2,3-dihydro-3,3-dimethyl -1,3'-[3H]indol]-5'-yl) boronic acid (384 mg, 1.9 mmol) and 2-bromo-5-nitrothiophene (300 mg, 1.4 mmol) to afford the title compound (270 mg, 0.9 mmol, 65%) as a yellow brown solid: mp. 223–225° C., ¹H NMR (CDCl₃) δ1.5 (s, 6H), 6.99 (d, J=8.1 Hz, 1H), 7.18 (d, J=4.3 Hz, 1H), 7.44 d, J=1.7 Hz, 1H), 7.51 (dd, J=8.1, 1.9 Hz, 1H), 7.91 (d, J=4.3 Hz, 1H), 8.07 (br s, 1H); MS (EI) m/z 288 (M)⁺.

EXAMPLE 84

2-(3,3-Dimethyl-2-oxo-2,3-dihydro-1H-indol-5yl)-pyrrole-1-carboxylic acid tert-butyl ester Prepared according to the procedure for example 18 using 5'-bromo-3,3-dimethyl-[1,3'-[3H]indol]-2'-(1'H)-one (1.24 g, 5.2 mmol) and N-BOC-pyrrole-2-boronic acid (1.5 g, 5.93 mmol) to afford the title compound (506 mg, 1.5 mmol, 30 %) as off-white solid: mp. 168.4–170.2° C., $^1$H NMR (DMSO-d$_6$) δ1.26 (s, 6H), 1.28 (s, 9H), 6.1 (dd, J=3.2, 1.8 Hz, 1H), 6.2 (dd, J=3.2, 3.2 Hz, 1H), 6.8 (d, J=7.9 Hz, 1H), 7.1 (dd, J=7.9, 1.6 Hz, 1H), 7.2 (d, J=1.6 Hz, 1H), 7.3 (dd, J=3.2, 1.8 Hz, 1H), 10.4 (s, 1H); MS (APCI) m/z 327 (M+H)+.

EXAMPLE 85

2-(3,3-Dimethyl-2-oxo-2,3-dihydro-1H-indol-5-yl)-2-nitro-pyrrole

To a solution of 2-(3,3-Dimethyl-2-oxo-2,3-dihydro-1H-indol-5-yl)-pyrrole-1-carboxylic acid tert-butyl ester (0.90 g, 2.8 mmol) in acetonitrile (anhydrous, 40 mL) at −15° C. was added silver nitrate (0.49 g, 2.9 mmol) followed by acetyl chloride (0.21 mL, 2.95 mmol). The reaction was allowed to warm to room temperature and stirred 16 h. Dichloromethane (250 mL) was added to the reaction mixture; filtered through celite and washed with water, saturated sodium bicarbonate, water then brine dried over magnesium sulfate, filtered and concentrated in vacuo. Purification via flash column chromatography on silica gel (2:3 ethyl acetate/hexane) gave 2-(3,3-Dimethyl-2-oxo-2,3-dihydro-1H-indol-5-yl)-2-nitro-pyrrole-1-carboxylic acid tert-butyl ester as a yellow solid: $^1$H NMR (CDCl$_3$) δ1.43 (s, 6H), 1.48 (s, 9H), 6.3 (d, J=4.1 Hz, 1H), 7.0 (d, J=8.0 Hz, 1H), 7.2 (d, J=4.1 Hz, 1H), 7.34 (d, J=1.7 Hz, 1H), 7.4 (dd, J=8.0, 1.7 Hz, 1H), 8.2 (s, 1H).

2-(3,3-Dimethyl-2-oxo-2,3-dihydro-1H-indol-5-yl)-2-nitro-pyrrole-1-carboxylic acid tert-butyl ester, was placed in a 50 mL round bottomed flask under nitrogen. A vigorous flow of nitrogen was maintained as the flask was placed in an oil bath and heated to 160° C. After 10 min at this temperature, the flask was removed from the oil bath and allowed to cool. The black residue was washed into a larger flask with acetone and adsorbed onto a small amount of florisil. Purification by flash column chromatography on silica gel (1:2 EtOAc:hexane) to afford the title compound (76 mg, 15%) which was triturated from ether/hexane to provide a greenish-yellow solid, mp 293.9–294.2° C. (dec). $^1$H NMR (DMSO-d$_6$) δ1.3 (s, 6H), 6.77 (d, J=4.3 Hz, 1H), 6.91 (d, J=8.1 HZ, 1H), 7.26 (d, J=4.3 Hz, 1H), 7.78 (dd, J=8.1, 1.8 Hz, 1H), 7.96 (d, J=1.8 Hz, 1H), 10.55 (s, 1H), 13.12 (s, 1H); MS (ESI) m/z 270 (M−H)$^-$.

EXAMPLE 86

5-(3,3-Dimethyl-2-oxo-2,3-dihydro-1H-indol-5-yl)-thiophene2-carbonitrile

Prepared according to the procedure for example 18 using (2'-oxo-[2, 3-dihydro-3,3-dimethyl-1,3'-[3H]indol]-5'-yl) boronic acid (570 mg, 2.8 mmol) and 5-bromo-thiophene-2-carbonitrile (350 mg, 1.9 mmol) to afford the title compound (299 mg, 1.1 mmol, 60%) as an off-white solid: mp. 255–256° C., $^1$H NMR (CDCl$_3$) δ$^1$H NMR (CDCl$_3$) δ1.46 (s, 6H), 6.97 (d, J=8.1 Hz, 1H), 7.21 (d, J=3.9 Hz, 1H), 7.39 (d, J=1.3 Hz, 1H), 7.47 (dd, J=8.1, 1.8 Hz, 1H), 7.58 (d, J=3.9 Hz, 1H), 8.14 (s, 1H); MS (EI) m/z 268 (M)$^+$.

EXAMPLE 87

3(3,3-Dimethyl-2-oxo-2,3-dihydro-1H-indol-5-yl)-2-fluoro-benzonitrile

Prepared according to the procedure for example 18 using (2'-oxo-[2,3-dihydro-3,3-dimethyl-1,3'-[3H]indol]-5'-yl) boronic acid (300 mg, 1.5 mmol) and 4-bromo-2-fluoro-benzonitrile (240 mg, 1.2 mmol) to afford the title compound (185 mg, 0.66 mmol, 55%) as an off white solid: mp. 270–272° C., $^1$H NMR (DMSO-d$_6$) δ1.31 (s, 6H), 6.96 (d, J=8.1 Hz, 1H), 7.67 (dd, J=8.1, 1.8 Hz, 1H), 7.74 (dd, J=8.2, 1.5 Hz, 1H), 7.85 (s, 1H), 7.89 (d, J=1.3 Hz, 1H), 7.96 (dd, J=7.5, 7.5, 1H), 10.56 (s, 1H); MS (ESI) m/z 279 (M−H)$^-$.

EXAMPLE 88

Pharmacology

The biological activity for the compounds of the current invention was evaluated in the in-vitro and in-vivo assays described below. In-vitro potencies lie in the range 0.01 nM–10,000 nM, and in-vivo potencies in the range 1 μg/kg to 100 mg/kg.

A. In-vitro Biology

The in-vitro biology is determined by (1) competitive Radioligand Binding: using the A-form of the human progesterone receptor with progesterone as the radioligand; (2) co-transfection assay, which provides functional activity expressed as agonist EC50 and Antagonist IC50 values; (3) a T47D cell proliferation, which is a further functional assay which also provides agonist and antagonist data; and (4) T47D cell alkaline phosphatase assay, which is a further functional assay which also provides agonist and antagonist data.

1. hPR Binding Assay

This assay is carried out in accordance with: Pathirana, C.; Stein, R. B.; Berger, T. S.; Fenical, W.; Ianiro, T.; Mais, D. E.; Torres, A.; Glodman, M. E., *Nonsteroidal human progesterone receptor modulators from the marine alga cymoplia barbata*, J. Steroid Biochem. Mol. Biol., 1992, 41, 733–738.

2. PRE-luciferase Assay in CV-1 Cells

The object of this assay is to determine a compound's progestational or antiprogestational potency based on its effect on PRE-luciferase reporter activity in CV-1 cells co-transfected with human PR and PRE-luciferase plasmids. The materials methods used in the assay are as follows.

a. Medium:

The growth medium was as follows: DMEM (Bio Whittaker) containing 10% (v/v) fetal bovine serum (heat inactivated), 0.1 mM MEM non-essential amino acids, 100 U/ml penicillin, 100 mg/ml streptomycin, and 2 mM GlutaMax (GIBCO, BRL). The experimental medium was as follows: DMEM (Bio Whittaker), phenol red-free, containing 10% (v/v) charcoal-stripped fetal bovine serum (heat-inactivated), 0.1 mM MEM non-essential amino acids, 100 U/ml penicillin, 100 mg/ml streptomycin, and 2 mM GlutaMax (GIBCO, BRL).

b. Cell Culture, Transfection Treatment, and Luciferase Assay

Stock CV-1 cells are maintained in growth medium Co-transfection is done using 1.2×10$^7$ cells, 5 mg pLEM plasmid with hPR-B inserted at Sph1 and BamH1 sites, 10 mg pGL3 plasmid with two PREs upstream of the luciferase sequence, and 50 mg sonicated calf thymus DNA as carrier DNA in 250 ml. Electroporation is carried out at 260 V and 1,000 mF in a Biorad Gene Pulser II. After electroporation, cells are resuspended in growth medium and plated in 96-well plate at 40,000 cells/well in 200 μl. Following overnight incubation, the medium is changed to experimental medium Cells are then treated with reference or test compounds in experimental medium. Compounds are tested for antiprogestational activity in the presence of 3 nM progesterone. Twenty-four hr. after treatment, the medium is discarded, cells are washed three times with D-PBS (GIBCO, BRL). Fifty μl of cell lysis buffer (Pronmega, Madison, Wis.) is added to each well and the plates are shaken for 15 min in a Titer Plate Shaker (Lab Line Instrument, Inc.). Luciferase activity is measured using luciferase reagents from Promega.

c. Analysis of Results

Each treatment consists of at least 4 replicates. Log transformed data are used for analysis of variance and nonlinear dose response curve fitting for both agonist and antagonist modes. Huber weighting is used to downweight the effects of outliers. $EC_{50}$ or $IC_{50}$ values are calculated from the retransformed values. JMP software (SAS Institute, Inc.) is used for both one-way analysis of variance and non-linear response analyses.

d. Reference Compounds

Progesterone and trimegestone are reference progestins and RU486 is the reference antiprogestin. All reference compounds are run in full dose-response curves and the $EC_{50}$ or $IC_{50}$ values are calculated.

TABLE 1

Estimated $EC_{50}$, standard error (SE), and 95% confidence intervals (CI) for reference progestins from three individual studies

| Compound | Exp. | EC50 (nM) | SE | 95% CI lower | 95% CI upper |
|---|---|---|---|---|---|
| Progesterone | 1 | 0.616 | 0.026 | 0.509 | 0.746 |
| | 2 | 0.402 | 0.019 | 0.323 | 0.501 |
| | 3 | 0.486 | 0.028 | 0.371 | 0.637 |
| Trimegestone | 1 | 0.0075 | 0.0002 | 0.0066 | 0.0085 |
| | 2 | 0.0081 | 0.0003 | 0.0070 | 0.0094 |
| | 3 | 0.0067 | 0.0003 | 0.0055 | 0.0082 |

TABLE 2

Estimated $IC_{50}$, standard error (SE), and 95% confident interval (CI) for the antiprogestin, RU486 from three individual studies

| Compound | Exp. | IC 50 (nM) | SE | 95% CI lower | 95% CI upper |
|---|---|---|---|---|---|
| RU486 | 1 | 0.028 | 0.002 | 0.019 | 0.042 |
| | 2 | 0.037 | 0.002 | 0.029 | 0.048 |
| | 3 | 0.019 | 0.001 | 0.013 | 0.027 |

Progestational activity: Compounds that increase PRE-luciferase activity significantly (p<0.05) compared to vehicle control are considered active.

Antiprogestational activity: Compounds that decrease 3 nM progesterone induced PRE-luciferase activity significantly (p<0.05)

$EC_{50}$: Concentration of a compound that gives half-maximal increase PRE-luciferase activity (default-nM) with SE.

$IC_{50}$: Concentration of a compound that gives half-maximal decrease in 3 nM progesterone induced PRE-luciferase activity (default-nM) with SE.

3. T47D Cell Proliferation Assay

The objective of this assay is the determination of progestational and antiprogestational potency by using a cell proliferation assay in T47D cells. A compound's effect on DNA synthesis in T47D cells is measured. The materials and methods used in this assay are as follows.

a. Growth Medium

DMEM:F12 (1:1) (GIBCO, BRL) supplemented with 10% (v/v) fetal bovine serum (not heat-inactivated), 100 U/ml penicillin, 100 mg/ml streptomycin, and 2 mM GlutaMax (GIBCO, BRL).

b. Treatment Medium

Minimum Essential Medium (MEM) (#51200-038GIBCO, BRL) phenol red-free supplemented with 0.5% charcoal stripped fetal bovine serum, 100 U/ml penicillin, 200 mg/ml streptomycin, and 2 mM GlutaMax (GIBCO, BRL).

c. Cell Culture

Stock T47 D cells are maintained in growth medium For BrdU incorporation assay, cells are plated in 96-well plates (Falcon, Becton Dickinson Labware) at 10,000 cells/well in growth medium. After overnight incubation, the medium is changed to treatment medium and cells are cultured for an additional 24 hr before treatment. Stock compounds are dissolved in appropriate vehicle (100% ethanol or 50% ethanol/50% DMSO), subsequently diluted in treatment medium and added to the cells. Progestin and antiprogestin reference compounds are run in full dose-response curves. The final concentration of vehicle is 0.1%. In control wells, cells receive vehicle only. Antiprogestins are tested in the presence of 0.03 nM trimegestone, the reference progestin agonist. Twenty-four hours after treatment, the medium is discarded and cells are labeled with 10 mM BrdU (Amersharn Life Science, Arlington Heights, Ill.) in treatment medium for 4 hr.

d. Cell Proliferation Assay

At the end of BrdU labeling, the medium is removed and BrdU incorporation is measured using a cell proliferation ELISA kit (#RPN 250, Amersham Life Science) according to manufacturer's instructions. Briefly, cells are fixed in an ethanol containing fixative for 30 min. followed by incubation in a blocking buffer for 30 min to reduce background. Peroxidase-labeled anti-BrdU antibody is added to the wells and incubated for 60 min. The cells are rinsed three times with PBS and incubated with 3,3'5,5'-tetramethylbenzidine (TMB) substrate for 10–20 min depending upon the potency of tested compounds. Then 25 μl of 1 M sulfuric acid is added to each well to stop color reaction and optical density is read in a plate reader at 450 nm within 5 min.

e. Analysis of Results

Square root-transformed data are used for analysis of variance and nonlinear dose response curve fitting for both agonist and antagonist modes. Huber weighting is used to downweight the effects of outliers. $EC_{50}$ or $IC_{50}$ values are calculated from the retransformed values. JMP software (SAS Institute, Inc.) is used for both one-way analysis of variance and non-linear response analyses in both single dose and dose response studies.

f. Reference Compounds

Trimegestone and medroxyprogesterone acetate (MPA) are reference progestins and RU486 is the reference antiprogestin. All reference compounds are run in full dose-response curves and the $EC_{50}$ or $IC_{50}$ values are calculated.

TABLE 3

Estimated $EC_{50}$, standard error (SE), and 95% confidence intervals (CI) for individual studies

| Compound | Exp | $EC_{50}$ (nM) | SE | 95% CI lower | 95% CI upper |
|---|---|---|---|---|---|
| Trimegestone | 1 | 0.017 | 0.003 | 0.007 | 0.040 |
| | 2 | 0.014 | 0.001 | 0.011 | 0.017 |

TABLE 3-continued

Estimated $EC_{50}$, standard error (SE), and
95% confidence intervals (CI) for individual studies

| Compound | Exp | $EC_{50}$ (nM) | SE | 95% CI lower | 95% CI upper |
|---|---|---|---|---|---|
| MPA | 3 | 0.019 | 0.001 | 0.016 | 0.024 |
|  | 1 | 0.019 | 0.001 | 0.013 | 0.027 |
|  | 2 | 0.017 | 0.001 | 0.011 | 0.024 |

TABLE 4

Estimated $IC_{50}$, standard error, and
95% confident interval for the antiprogestin, RU486

| Compound | Exp | $IC_{50}$ (nM) | SE | 95% CI lower | 95% CI upper |
|---|---|---|---|---|---|
| RU486 | 1 | 0.011 | 0.001 | 0.008 | 0.014 |
|  | 2 | 0.016 | 0.001 | 0.014 | 0.020 |
|  | 3 | 0.018 | 0.001 | 0.014 | 0.022 |

$EC_{50}$: Concentration of a compound that gives half-maximal increase in BrdU incorporation with SE; $IC_{50}$: Concentration of a compound that gives half-maximal decrease in 0.1 trimegestone induced BrdU incorporation with SE 4. T47D Cell Alkaline Phosphatase Assay The purpose of this assay is to identify progestins or antiprogestins by determining a compound's effect on alkaline phosphatase activity in T47D cells. The materials and methods used in this assay are as follows.

a. Culture Medium

DMEM:F12 (1:1) (GIBCO, BRL) supplemented with 5% (v/v) charcoal stripped fetal bovine serum (not heat-inactivated), 100 U/ml penicillin, 100 µg/ml streptomycin, and 2 mM GlutaMax (GIBCO, BRL).

b. Alkaline Phosphatase Assay Buffer

I. 0.1 M Tris-HCl, pH 9.8, containing 0.2% Triton X-100
II. 0.1 M Tris-HCl, pH 9.8 containing 4 mM p-nitrophenyl phosphate (Sigma).

c. Cell Culture and Treatment

Frozen T47D cells were thawed in a 37° C. water bath and diluted to 280,000 cells/ml in culture medium. To each well in a 96-well plate (Falcon, Becton Dickinson Labware), 180 µl of diluted cell suspension was added. Twenty µl of reference or test compounds diluted in the culture medium was then added to each well. When testing for progestin antagonist activity, reference antiprogestins or test compounds were added in the presence of 1 nM progesterone. The cells were incubated at 37° C. in a 5% $CO_2$/humidified atmosphere for 24 hr.

d. Alkaline Phosphatase Enzyme Assay

At the end of treatment, the medium was removed from the plate and fifty µl of assay buffer I was added to each well. The plates were shaken in a titer plate shaker for 15 min. Then 150 µl of assay buffer II was added to each well. Optical density measurements were taken at 5 min intervals for 30 min at a test wavelength of 405 nM.

e. Analysis of Results

Analysis of Dose-response Data

For reference and test compounds, a dose response curve is generated for dose (X-axis) vs. the rate of enzyme reaction (slope) (Y-axis). Square root-transformed data are used for analysis of variance and nonlinear dose response curve fitting for both agonist and antagonist modes. Huber weighting is used to downweight the effects of outliers. $EC_{50}$ or $IC_{50}$ values are calculated from the retransformed values. JMP software (SAS Institute, Inc.) is used for both one-way analysis of variance and non-linear dose response analyses in both single dose and dose response studies.

f. Reference Compounds:

Progesterone and trimegestone are reference progestins and RU486 is the reference antiprogestin. All reference compounds are run in fill dose response curves and the $EC_{50}$ or $IC_{50}$ values are calculated.

TABLE 5

Estimated $EC_{50}$, standard error (SE), and
95% confidence intervals (CI) for reference
progestins from three independent experiments

| Compound | Exp. | EC50 (nM) | SE | 95% CI lower | 95% CI upper |
|---|---|---|---|---|---|
| Progesterone | 1 | 0.839 | 0.030 | 0.706 | 0.996 |
|  | 2 | 0.639 | 0.006 | 0.611 | 0.669 |
|  | 3 | 1.286 | 0.029 | 1.158 | 1.429 |
| Trimegestone | 1 | 0.084 | 0.002 | 0.076 | 0.091 |
|  | 2 | 0.076 | 0.001 | 0.072 | 0.080 |
|  | 3 | 0.160 | 0.004 | 0.141 | 0.181 |

TABLE 6

Estimated $IC_{50}$, standard error, and
95% confident interval for the reference antiprogestin
RU486 from three independent experiments

| Compound | Exp | IC 50 (nM) | SE | 95% CI lower | 95% CI upper |
|---|---|---|---|---|---|
| RU486 | 1 | 0.103 | 0.002 | 0.092 | 0.115 |
|  | 2 | 0.120 | 0.001 | 0.115 | 0.126 |
|  | 3 | 0.094 | 0.007 | 0.066 | 0.134 |

B. In-vivo Biology

The primary in-vivo assay is the rat decidualization model which may be used to determine progestational effects of both agonists and antagonists. The secondary in-vivo assay is the rat ovulation inhibition model which is under development and hence the protocol is un-available.

1. Rat Decidualization Assay

The objective of this procedure is used to evaluate the effect of progestins and antiprogestins on rat uterine decidualization and compare the relative potencies of various test compounds. The materials and methods used in this assay are as follows.

a. Methods

Test compounds are dissolved in 100% ethanol and mixed with corn oil (vehicle). Stock solutions of the test compounds in oil (Mazola™) are then prepared by heating (~80° C.) the mixture to evaporate ethanol. Test compounds are subsequently diluted with 100% corn oil or 10% ethanol in corn oil prior to the treatment of animals. No difference in decidual response was found when these two vehicles were compared.

b. Animals (RACUC protocol #5002)

Ovariectomized mature female Sprague-Dawley rats (~60-day old and 230 g) are obtained from Taconic (Taconic Farms, N.Y.) following surgery. Ovariectomy is performed at least 10 days prior to treatment to reduce circulating sex steroids. Animals are housed under 12 hr light/dark cycle and given standard rat chow and water ad libitum.

c. Treatment

Rats are weighed and randomly assigned to groups of 4 or 5 before treatment. Test compounds in 0.2 ml vehicle are administered by subcutaneous injection in the nape of the neck or by gavage using 0.5 ml. The animals are treated once daily for seven days. For testing antiprogestins, animals are given the test compounds and a $EC_{50}$ dose of progesterone (5.6 mg/kg) during the first three days of treatment. Following decidual stimulation, animals continue to receive progesterone until necropsy four days later.

d. Dosing

Doses are prepared based upon mg/kg mean group body weight. In all studies, a control group receiving vehicle is included. Determination of dose-response curves is carried out using doses with half log increases (e.g. 0.1, 0.3, 1.0, 3.0 mg/kg.).

e. Decidual Induction

Approximately 24 hr after the third injection, decidualization is induced in one of the uterine horns by scratching the antimesometrial luminal epithelium with a blunt 21 G needle. The contralateral horn is not scratched and serves as an unstimulated control. Approximately 24 hr following the final treatment, rats are sacrificed by $CO_2$ asphyxiation and body weight measured. Uteri are removed and trimmed of fat. Decidualized (D-horn) and control (C-horn) uterine horns are weighed separately.

f. Analysis of Results

The increase in weight of the decidualized uterine horn is calculated by D-horn/C-horn and logarithmic transformation is used to maximize normality and homogeneity of variance. The Huber M-estimator is used to down weight the outlying transformed observations for both dose-response curve fitting and one-way analysis of variance. JMP software (SAS Institute, Inc.) is used for both one-way ANOVA and non-linear dose-response analyses.

g. Reference Compounds

All progestin reference compounds were run in full dose-response curves and the $EC_{50}$ for uterine wet weight were calculated.

TABLE 7

Estimated $EC_{50}$, standard error (SE), and 95% confidence intervals for individual studies

| Compound | Exp | $EC_{50}$ (mg/kg. s.c.) | SE | 95% CI lower | 95% CI upper |
|---|---|---|---|---|---|
| Progesterone | 1 | 5.50 | 0.77 | 4.21 | 7.20 |
|  | 2 | 6.21 | 1.12 | 4.41 | 8.76 |
| 3-Ketodesogestrel | 1 | 0.11 | 0.02 | 0.07 | 0.16 |
|  | 2 | 0.10 | 0.05 | 0.11 | 0.25 |
|  | 3 | 0.06 | 0.03 | 0.03 | 0.14 |
| Levonorgestrel | 1 | 0.08 | 0.03 | 0.04 | 0.16 |
|  | 2 | 0.12 | 0.02 | 0.09 | 0.17 |
|  | 3 | 0.09 | 0.02 | 0.06 | 0.13 |
|  | 4 | 0.09 | 0.02 | 0.06 | 0.14 |
| MPA | 1 | 0.42 | 0.03 | 0.29 | 0.60 |
|  | 2 | 0.39 | 0.05 | 0.22 | 0.67 |
|  | 3 | 0.39 | 0.04 | 0.25 | 0.61 |

TABLE 8

Estimated average $EC_{50}$, standard error, and 95% confidence intervals for dose-response curves of 3 reference compounds

| Compound | $EC_{50}$ (mg/kg, s.c.) | SE | 95% CI lower | 95% CI upper |
|---|---|---|---|---|
| Progesterone | 5.62 | 0.62 | 4.55 | 7.00 |
| 3-Ketodesogestrel | 0.10 | 0.02 | 0.07 | 0.14 |
| Levonorgestrel | 0.10 | 0.01 | 0.08 | 0.12 |

TABLE 9

Estimated $IC_{50}$, standard error, and 95% confident interval for the antiprogestin, RU 486

| Compound | Exp. | $IC_{50}$ (mg/kg, p.o.) | SE | 95% CI lower | 95% CI upper |
|---|---|---|---|---|---|
| RU 486 | 1 | 0.21 | 0.07 | 0.05 | 0.96 |
|  | 2 | 0.14 | 0.02 | 0.08 | 0.27 |

Concentration: Compound concentration in assay (default-mg/kg body weight)

Route of administration: Route the compound is administered to the animals

Body weight: Mean total animal body weight (default-kg)

D-horn: Wet weight of decidualized uterine horn (default-mg)

C-horn: Wet weight of control uterine horn (default-mg)

Decidual response: $[(D-C)/C] \times 100\%$

Progestational activity: Compounds that induce decidualization significantly (p<0.05) compared to vehicle control are considered active Antiprogestational activity: Compounds that decrease $EC_{50}$ progesterone induced decidualization significantly (p<0.05)

$EC_{50}$ for uterine weight: Concentration of compound that gives half-maximal increase in decidual response (default-mg/kg)

$IC_{50}$ for uterine weight: Concentration of compound that gives half-maximal decrease in $EC_{50}$ progesterone induced decidual response (default-mg/kg)

Data for Representative Compounds

| Example # | Ki/nM | CV-1 IC50/nM | Decid. IC50 mg/kg |
|---|---|---|---|
| 34 | 19 | 14 | 50% @ 10 |
| 35 | 22 | 19 | 50% @ 10 |
| 80 |  |  | 70% # 3 |
| 77 |  |  | 60% @ 3 |
| 44 | 123 | 20 | 50% @ 3 |
| 73 |  |  | 50% @ 3 |
| 36 | 4.8 | 9 | 50% @ 10 |
| 32 | 9 | 1 | 60% @ 10 |
| 47 | 18 | 7 | 50% @ 10 |

EXAMPLE 89

4-(1,2-Dihydro-2-oxospiro[cyclohexane-1,3-[3H]indol]-5-yl)-2-fluorobenzeneacetonitrile Prepared from 4-bromo-2-fluorophenylacetonitrile and (2'-oxo-2',3'-dihydrospiro[cyclohexane-1,3'-[3H]indol]-5'- yl) boronic acid according to the procedure for example 18 to afford the title compound as a white solid; mp. 180–183° C.; $^1$H-NMR (DMSO-d$_6$) δ10.4 (s, 1H), 7.7 (s, 1H), 7.6–7.7 (m, 4H) 6.9 (d, 1H, J=8.1 Hz), 4.1(s, 2H), 1.9 (m, 2H), 1.7–1.6 (m, 8H). MS (APCI (–)) m/z 333 [M–H]$^-$ Anal. calc. for C$_{21}$H$_{19}$FN$_2$O. 0.5 H$_2$O: C, 73.49, H, 5.87, N, 8.20. Found: C, 73.55, H, 5.50, N, 7.36.

EXAMPLE 90

5(3-Fluoro-4-methoxyphenyl)spiro[cyclohexane-1,3-[3H]indol]-2(1H)-one

Prepared from 4-bromo-2-fluoroanisole and (2'-oxo-2',3'-dihydrospiro[cyclohexane-1,3'-[3H]indol]-5'-yl) boronic acid according to the procedure for example 18 to afford the title compound as a white solid, nip. 178–180° C.; $^1$H-NMR (DMSO-d6) δ10.4 (s, 1H), 7.65 (d, 1H, J=1.1 Hz), 7.5–7.4 (m, 3H), 7.2(t, 1H, J=8.9 Hz), 6.9 (d, 1H, J=8 Hz), 3.9(s, 3H), 1.9 (m, 2H) 1.7–1.6 (m, 8H); MS (APCI (–)) m/z 324 [M–H]$^-$; Anal. Calc. For C$_{20}$H$_{20}$FNO$_2$. :C, 73.83, H, 6.20, N, 4.30. Found: C, 73.55, H, 6.23, N, 4.40.

EXAMPLE 91

5-(3-Chlorophenyl)spiro[cyclobutane-1,3-[3H]indole]-2(1H)-one

5-Bromospiro[cyclobutane-1,3-[3H]indol]-2(1H)-one.

To a stirred solution of spiro[cyclobutane-1,3'-[3H]indol]-2'(1'H)-one (J. Med. Chem. 1987, 824–9) (1.0 g, 6 mmol) in glacial acetic acid (10 mL) was added dropwise at room temperature a solution of bromine (0.30 mL, 6 mmol) in glacial acetic acid (6 mL). After stirring for 10 min, anhydrous sodium acetate (0.47 g, 6 mmol) was added and the solution was concentrated in vacuo. The residue was dissolved in ethyl ether (50 mnL) and washed sequentially with water (50 mL), aqueous saturated sodium bicarbonate solution (50 mL), water (50 mL) and brine (30 mL). The organic layer was dried over magnesium sulfate, filtered and concentrated in vacuo. Crystallization from ethyl ether yielded the product as a white fluffy solid (1.1 g, 73%), mp 235–7° C.; $^1$H NMR (DMSO-d$_6$, 300 MHz) δ2.15–2.41 (m, 6H), 6.74 (d, 1H, J=8.2 Hz), 7.33 (dd, 1H, J=2, 8.2 Hz), 7.75 (d, 1H, J=2 Hz), 10.36 (bs, 1H); MS (EI) m/z 251 [M$^+$]; Anal. Calcd for C$_{11}$H$_{10}$BrNO: C, 52.41; H, 4.00; N, 5.56. Found: C, 51.98; H, 4.24; N, 5.42.

To a solution of 5-bromospiro[cyclobutane-1,3-[3H]indol]-2(1H)-one (0.6 g, 2 mmol) in ethylene glycol dimethyl ether (50 mL) under a nitrogen atmosphere was added tetrakis(triphenylphosphine)palladium(0) (140 mg, 0.1 mmol). To the solution was added sequentially 3-chlorophenyl boronic acid (0.48 g, 3 mmol) and potassium carbonate (0.76 g, 5 mmol) in water (5 mL). The mixture was heated to 80° C. for 3 h and allowed to cool. The reaction mixture was poured into water (100 mL) and extracted with ethyl acetate (3×100 mL). The organic layers were combined, washed with brine (50 mL) and dried over magnesium sulfate. The solution was filtered, concentrated in vacuo, and the residue was purified by HPLC (Zorbax PRO, C18, 10u, 15A, 50×250 mm; 35% Water/65% AcCN; 254 NM; AMB. temp.) to give the title compound (200 mg, 35%) as a white powder, mp 199.5–201° C. $^1$H NMR (DMSO-d$_6$, 300 MHz) δ2.21–2.28 (m, 2H), 2.40–2.45 (m, 4H), 6.87 (d, 1H, J=8.1 Hz), 7.37 ('d', 1H), 7.44–7.52 (m, 2H), 7.65 (bd, 1H, J=7.8 Hz), 7.76 (bs, 1H), 7.92 (bs, 1H), 10.35 (s, 1H). MS (EI) m/z 283 [M$^+$]. Anal. Calcd for C$_{17}$H$_{14}$ClNO: C, 71.96; H, 4.97; N, 4.94. Found: C, 70.75; H, 5.07; N, 4.68.

EXAMPLE 92

5-(3-Chlorophenyl)spiro[cyclopropane-1,3-[3H]indole]-2(1H)-one

To 5-(3-chloro-phenyl)-1,3-dihydro-indol-2-one (1.2 g, 5 mmol) in tetrahydrofuran (25 mL, anhydrous) at –20° C. was added slowly n-butyllithium (2.5 M solution in hexanes, 3.93 mL, 9.8 mmol), followed by N,N,N',N'-tetramethylethylenediamine (1.48 mL, 9.8 mmol). After 15 min, 1,2-dibromoethane (1.27 mL, 15 mmol) was added slowly and the mixture was allowed to reach room temperature. After 5 days, saturated aqueous ammonium chloride solution (50 mL) and ethyl acetate (50 mL) were added. The layers were separated and the aqueous phase was extracted with ethyl acetate (2×25 mL). The organic layers were combined, washed with 1 N HCl (25 mL) and brine (25 mL), and dried over magnesium sulfate. The solution was filtered and concentrated in vacuo. The residue was purified by flash column chromatography (40% ethyl acetate/hexane) on a pad of silica gel to give the product (40 mg) as white crystals, mp 212–214° C.; $^1$H NMR (CDCl$_3$, 300 MHz) δ1.59–1.63 (m, 2H), 1.80–1.84 (m, 2H), 7.00–7.03 (m, 2H), 7.28–7.42 (m, 4H), 7.51 ('t', 1H), 7.85 (bs, 1H). MS (EI) m/z 269 [M$^+$]. Anal. Calcd for C$_{16}$H$_{12}$ClNO: C, 71.25; H, 4.48; N, 5.19. Found: C, 70.78; H, 4.88; N, 5.10.

EXAMPLE 93

2-Nitro-5-(1.2-dihydro-2-oxospiro[cyclobutane-1,3-[3H]indol]-5-yl)1H-pyrrole-1-carboxylic acid, tert-butyl ester 1-t-Butoxycarbonylpyrrole-2-boronic acid.

To 1-tert-butyl pyrrolecarboxylate (Aldrich, 25 g, 0.15 mol, 1.0 eq) in THF at –78° C. (anhydrous, 250 mL) was added LDA (2 M solution in heptane/THF/ethylbenzene, 82 mL, 1.1 eq). After stirring for 30 min at –78° C., trimethylborate (85 mL, 0.750 mol, 5.0 eq) was added. After stirring at –78° C. for 1 h, the dry ice bath was removed and the reaction was allowed to come to room temperature overnight. HCl (0.25 N, 200 mL) was added to the reaction and the THF was removed in vacuo. The aqueous layer was extracted with ethyl ether (3×300 mL). The combined ether layers were washed with water (2×200 mL), then with brine (200 mL), and dried over magnesium sulfate. The solution was filtered and concentrated in vacuo. When the product began to crystallize on the rotary, the flask was removed and allowed to stand. The crystals were filtered and washed with ice-cold ethyl ether to give the product (14 g, 44%) as a white solid. Several crystallizations of filtrate from cold ether gave more product (4.5 g, 14%).

5-(1,2-dihydro-2-oxospiro[cyclobutane-1,3-[3H]indol]-5-yl)-1H-pyrrole-1-carboxylic acid, tert-butyl ester To a solution of 5-Bromospiro[cyclobutane-1,3-[3H]indol]-2(1H)-one (WAY-163202) (0.6 g, 2.4 mmol) in ethylene glycol dimethyl ether (50 mL) under a nitrogen atmosphere was added tetrakis(triphenylphosphine)palladium(0) (140 mg, 0.1 mmol). To the solution was added sequentially 1-t-butoxycarbonylpyrrole-2-boronic acid (0.65 g, 3.1 mmol) and potassium carbonate (0.75 g, 5.4 mmol) in water (5 mL). The mixture was heated to 80° C. for 3 h and allowed to cool. The reaction mixture was poured into water (100 mL) and extracted with ethyl acetate (3×100 mL). The organic layers were combined, washed with brine (50 mL) and dried over magnesium sulfate. The solution was filtered, concentrated in vacuo, and the residue was purified by flash column chromatography to give the product (0.7 g, 86%) as a tan powder, mp 163–165° C. $^1$H NMR (DMSO-d$_6$, 400 MHz) δ1.3 (s, 9H), 2.16–2.49m, 6H), 6.19 (dd, 1H, J=1.8, 3.2 Hz), 6.24 (t, 1H, J=3.3 Hz), 6.76 (d, 1H, J=8.1Hz), 7.09 (dd, 1H, J=1.8, 8.0 Hz), 7.30 (dd, 1H, J=1.8, 3.3), 7.48 (d, 1H, J=1.8 Hz), 10.24 (s, 1H) MS (APCI) m/z 339 [M+H]$^+$. Anal. Calcd for C$_{20}$H$_{22}$N$_2$O$_3$: C, 70.99; H, 6.55; N, 8.28. Found: C, 69.51; H, 6.38; N, 7.69.

To a solution of 5-(1,2-dihydro-2-oxospiro[cyclobutane-1,3-[3H]indol]-5-yl)-1H-pyrrole-1-carboxylic acid, tert-butyl ester (0.97 g, 2.9 mmol) in acetonitrile (50 mL) and dichloromethane (5 mL) at −20° C. was added silver nitrate (0.51 g, 3.0 mmol). After 20 min, acetyl chloride (0.20 mL, 2.9 mmol) in acetonitrile (3 mL) was added and the solution was allowed to come to room temperature. After 24 h, the reaction mixture was diluted with dichloromethane (100 mL) and filtered through celite. The filtrate was poured into water (100 mL) and the layers were separated. The organic layer was washed with brine (50 mL) and dried over magnesium sulfate. The solution was filtered, concentrated in vacuo and the residue was purified by flash column chromatography on silica gel (40% ethyl acetate/hexane) to give the title compound (415 mg, 37%) as a yellow powder, rmp 265° C. (dec.). $^1$H NMR (DMSO-d$_6$; 400 MHz) δ1.45 (s, 9H), 2.17–2.48 (m, 6H), 6.60 (d, 1H, J=4.2 Hz), 6.90 (d, 1H, J=8.1Hz), 7.35 (dd, 1H, J=2.0, 8.1Hz), 7.46 (d, 1H, J=4.2 Hz), 7.70 ('d', 1H, J=1.8 Hz), 10.50 (s, 1H). MS (ESI) m/z 382 [M−H]$^-$. Anal. Calcd for C$_{20}$H$_{21}$N$_3$O$_5$: C, 62.65; H, 5.52; N, 10.96. Found: C, 62.58; H, 5.60; N, 10.91.

EXAMPLE 94

Nitro-5-(1,2-dihydro-2-oxospiro[cyclopentane-1,3-[3H]indol]-5-yl)-1H-pyrrole-1-carboxylic acid, tert-butyl ester To a solution of 5-(1,2-dihydro-2-oxospiro[cyclopentane-1,3-[3H]indol]-5-yl)-1H-pyrrole-1-carboxylic acid, tert-butyl ester (1.5 g, 4.0 mmol) in acetonitrile (50 mL) and dichloromethane (5 mL) at −20° C. was added silver nitrate (0.76 g, 4.5 mmol). After 20 min acetyl chloride (0.30 mL, 4.0 mmol) in acetonitrile (3 mL) was added and the solution was allowed to come to room temperature. After 24 h, the reaction mixture was diluted with dichloromethane (100 mL) and filtered through celite. The filtrate was poured into water (100 mL) and the layers were separated. The organic layer was washed with brine (50 mL) and dried over magnesium sulfate. The solution was filtered, concentrated in vacuo and the residue was purified by flash column chromatography on silica gel (40% ethyl acetate/hexane) to give the title compound (650 mg, 41%) as a yellow powder, mp 150–153° C. $^1$H NMR (DMSO-d$_6$; 400 MHz) δ1.42 (s, 9H), 1.77–2.00 (m, 8H), 6.55 (d, 1H, J=4.2 Hz), 6.93 (d, 1H, J=8.0 Hz), 7.33 (dd, 1H, J=1.7, 8.0 Hz), 7.37 ('d', 1H, J=1.7 Hz), 7.43 (d, 1H, J=4.2 Hz), 10.53 (s, 1H). MS ((−) APCI) m/z 396 [M−H]$^-$. Anal. Calcd for C$_{21}$H$_{23}$N$_3$O$_5$: C, 63.47; H, 5.83; N, 10.57. Found: C, 62.95; H, 5.52; N, 10.32.

EXAMPLE 95

5-(5-Nitro-1H-pyrrol-2-yl)spiro[cyclobutane-1,3-[3H]indol]-2(1H)-one

2-Nitro-5-(1,2-dihydro-2-oxospiro[cyclobutane-1,3-[3H]indol]-5-yl)-1H-pyrrole-1-carboxylic acid, tert-butyl ester (350 mg, 0.91 mmol) was placed in a 25 mL round bottomed flask stoppered with a rubber septum and equipped with nitrogen inlet and a needle to allow gaseous outflow. A vigorous flow of nitrogen was maintained as the flask was placed in an oil bath and heated to 150° C. After 20 min at this temperature, the flask was removed from the oil bath and allowed to cool. The residue was dissolved in acetone and was purified by flash column chromatography (40% ethyl acetate/hexane) on a pad of silica gel. Further purification by HPLC gave the title compound (100 mg, 39%) as a bright yellow powder, mp 250° C. (dec.); $^1$H NMR (DMSO-d$_6$, 400 MHz) δ2.18–2.48 (m, 6H), 6.77 (dd, 1H, J=2.4, 4.4 Hz), 6.83 (d, 1H, J=8.1 Hz), 7.25 (dd, 1H, J=2.4, 4.3 Hz), 7.73 (dd, 1H, J=2.0, 8.1 Hz), 8.23 ('d', 1H, J=1.8 Hz), 10.41 (bs, 1H), 13.13 (s, 1H); MS (ESI) m/z 282 [M−H]. Anal. Calcd. For C$_{15}$H$_{13}$N$_3$O$_3$: C, 63.60; H, 4.63; N, 14.83. Found: C, 62.59; H, 4.58; N, 14.28.

EXAMPLE 96

5-(5-Nitro-1H-pyrrol-2-yl)spiro[cyclopentane-1,3-[3H]indol]-2(1H)-one

2-Nitro-5-(1,2-dihydro-2-oxospiro[cyclopentane-1,3-[3H]indol]-5-yl)-1H-pyrrole-1-carboxylic acid, tert-butyl ester (580 mg, 1.5 mmol) was placed in a 25 mL round bottomed flask stoppered with a rubber septum and equipped with nitrogen inlet and a needle to allow gaseous outflow. A vigorous flow of nitrogen was maintained as the flask was placed in an oil bath and heated to 150° C. After 20 min at this temperature, the flask was removed from the oil bath and allowed to cool. The residue was dissolved in acetone and was purified by flash column chromatography (40% ethyl acetate/hexane) on a pad of silica gel. Further purification by HPLC gave the title compound (300 mg, 67%) as a yellow powder, mp 275° C. (dec.). $^1$H NMR (DMSO-d$_6$, 400 MHz) δ1.78–2.07 (m, 8H), 6.77 (dd, 1H, J=2.4, 4.2 Hz), 6.86 (d, 1H, J=8.2 Hz), 7.24 (dd, 1H, J=2.4, 4.2 Hz), 7.71 (dd, 1H, J=1.8, 8.2 Hz), 7.87 ('d', 1H, J=1.8 Hz), 10.47 (bs, 1H), 13.12 (s, 1H). MS (ESI) m/z 296 [M−H]$^-$. Anal. Calcd. For C$_{16}$H$_{15}$N$_3$O$_3$: C, 64.64; H, 5.09; N, 14.13. Found: C, 63.82; H, 5.20; N, 13.73.

EXAMPLE 97

5-(1,2-dihydro-2-oxospiro[cyclopentane-1,3-[3H]indol]-5-yl)-1H-pyrrole-1-carboxylic acid, tert-butyl ester A solution of 5'-Bromospiro[cyclopentane-1,3'-[3H]indol]-2'(1H)-one (2.0 g, 7.5 mmol) and tetrakis(triphenylphosphine)palladium(0) (430 mg, 0.3 mmol) in ethylene glycol dimethyl ether (50 mL) was stirred under a flow of nitrogen for 15 min. To the solution was added sequentially 1-t-butoxycarbonylpyrrole-2-boronic acid (2.1 g, 9.7 mmol) and potassium carbonate (2.4 g, 17 mmol) in water (10 mL). The mixture was heated to 80° C. for 3 h and allowed to cool. The reaction mixture was poured into water (50 mL) and extracted with ethyl acetate (3×50 mL). The organic layers were combined, washed with brine (30 mL) and dried over magnesium sulfate. The solution was filtered and concentrated in vacuo. Crystallization from 20% ethyl acetate/hexane gave the product (2.2 g, 83%) as a white powder, mp 179–180.5° C. $^1$H NMR (DMSO-d$_6$, 400 MHz) δ1.30 (s, 9H), 1.75–1.98 (m, 8H), 6.16 (dd, 1H, J=1.8, 3.3 Hz), 6.22 ('t', 1H, J=3.3, 3.3 Hz), 6.79 (d, 1H, J=7.9 Hz), 7.08 (dd, 1H, J=1.8, 7.9 Hz), 7.14 ('d', 1H, J=1.5 Hz), 7.28 (dd, J=1.9, 3.3 Hz), 10.30 (s, 1H); MS (EI) m/z 352 [M$^+$]; Anal. Calcd for C$_{21}$H$_{24}$N$_2$O$_3$: C, 71.57; H, 6.86; N, 7.95. Found: C, 71.08; H, 6.83; N, 7.74.

To a solution of 5-(1,2-dihydro-2-oxospiro[cyclopentane-1,3-[3H]indol]-5-yl)-1H-pyrrole-1-carboxylic acid, tert-butyl ester (WAY-163755) (2.2 g, 6.0 mmol) in THF (anhydrous, 25 mL) was added at −78° C. chlorosulfonyl isocyanate (0.63 mL, 7.0 mmol). After 90 min, dimethylformamide (11 mL, 140 mmol) was added and the reaction was allowed to warm to room temperature. The reaction mixture was poured into water (50 mL) and extracted with ethyl acetate (2×50 mL). The organic layers were combined, washed with brine (50 mL), dried over magnesium sulfate, filtered and concentrated in vacuo. Purification via flash column chromatography on silica gel (30% ethyl acetate/hexane) gave the title compound (1.7 g, 75%) as white crystals, mp 167–9° C.; $^1$H NMR (DMSO-d$_6$, 400 MHz) δ1.34 (s, 9H), 1.75–1.98 (m, 8H), 6.39 (d, 1H, J=3.7 Hz), 6.84 (d, 1H, J=7.9 Hz), 7.17 (dd, 1H, J=1.8, 7.9 Hz), 7.28 ('t', 2H), 10.41 (s, 1H); MS (ESI) m/z 376 [M–H]$^-$. Anal. Calcd. for C$_{22}$H$_{23}$N$_3$O$_3$: C, 70.01; H, 6.14; N, 11.13. Found: C, 69.67; H, 6.38; N, 11.04.

EXAMPLE 98

5-(1,2-Dihydro-2-oxospiro[cyclohexane-1,3-[3H]indol]-5-yl)-4-propyl-2-thiophenecarbonitrile The title compound was prepared in a manner similar to example 69 from 5bromo-4-n-propyl thiophene-2-carbonitrile (1.17 g, 5 mmol), ( 1,2-dihydro-2-oxospiro[cyclohexane-1,3-[3H]indol)-5-boronic acid (1.24 g, 5 mmol), tetrakis(triphenylphosphine) palladium, potassium carbonate (2.75 g,21 mmol), water (10mL ), and dimethoxyethane (50 mL) heated at reflux over night, to afford the title compound (0.7 g, 40%): m.p. 168–171° C.; $^1$H NMR (DMSO-d$_6$) δ10.56 (s, 1H), 7.93 ( s, 1H ) 7.52–7.51 (d, 1H, J=1.5 Hz), 7.33–7.29 (dd, 1H, J=1.6 Hz), 7.00–6.96 (d, 1H, J=8.0 Hz), 2.62–2.57 (t, 2H), 1.86 (m, 2H), 1.70–1.56 (m, 11H), 0.88–0.84 (t, H); MS m/z (APCI (+)) 351 [M+H]$^+$. IR (KBr) 1620, 1700, 2200 cm$^{-1}$; Anal. Calc. For C$_{21}$H$_{22}$N$_2$OS 1/2 H$_2$O: C, 70.2; H, 6.39; N, 7.79. Found. C, 70.67; H,6.34; N,7.62.

EXAMPLE 99

5-(1,2-Dihydro-2-oxospiro[cyclohexane-1,3-[3H]indol]-5-yl)4-n-butyl-2-thiophenecarbonitrile The title compound was prepared in a manner similar to example 69 from 5-bromo-4-n-butyl thiophenecarbonitrile[1] (1.24 g, 5.1 mmol), (1,2-dihydro-2-oxospiro[cyclohexane-1,3-[3H] indol)-5-boronic acid (1.24 g, 5.05 mmol), tetrakis (triphenylphosphine) palladium (0.25 g), potassium carbonate (2.75 g, 21 mmol), water (10 mL),and dimethoxyethane (50 mL) heated at reflux for 5 hours to afford the title compound (1 g, 54%), mp.130–132° C. $^1$H NMR ( DMSO-d$_6$) δ10.56 (s, 1H), 7.92 (s, 1H) , 7.52–7.51 (d, 1H, J=1.2 Hz), 7.32–7.29 (dd, 1H, J=1.5 Hz), 6.98–6.96 (d, 1H, J=8.0 Hz), 2.64–2.59 (t, 2H), 1.99–1.86 (m, 2H), 1.7–1.50 (m, 11H), 1.32–1.22 (m, 2H), 0.86–0.82 (t, 3H ); MS (APCI (+)) m/z 365 [M+H]$^+$; IR (KBr) 1620, 1700; 2200 cm$^{-1}$; Anal. Calc. For C$_{22}$H$_{24}$N$_2$OS 1/4 H$_2$O. C, 71.61; H, 6.69; N, 7.59. Found: C, 71.13; H, 6.61; N, 6.91.

EXAMPLE 100

5-(3-Chlorophenyl)-4-methylspiro[cylohexane-1,3-3H]indol]-2(1H)-one

To a –25° C. solution of 4-methyl-2-oxindole (3.0 g, 20.2 mmol) (Tett, 1966, 22, 10, 3337-43) in of anhydrous THF (100 mL) under N$_2$ is added N,N,N',N'-tetramethylethylenediamine (8.0 mL, 51.0 mmol) followed by dropwise addition of n-butyl lithium (10.0 M in hexanes, 5.1 mL, 51.0 mmol). After 30 min. a solution of 1,5-diiopentane (9.2 mL, 61.0 mmol) in 3 (mL) of THF was added and the reaction mixture was allowed to warm to RT and stir for 14 h. The reaction mixture was poured into water, extracted with EtOAc (×2), the combined organic layers were washed with dil. HCl (pH 1), water (×2), dried (MgSO4) and evaporated. The residue was purified by column chromatography (SiO$_2$, ethyl acetate: hexane 1:4) to afford the product (3.2 g, 15 mmol, 74%) as a tan solid: $^1$H NMR (CDCl$_3$) δ1.2–1.45 (m, 1H), 1.55–1.75 (m, 4H), 1.85–1.95 (d, J=13 Hz, 1H), 2.05–2.35 (m, 4H), 2.47 (s, 3H), 6.72 (dd, J=8.1, 1.0 Hz, 1H), 6.95 (dd, J=8.1, 8.0 Hz, 1H), 7.32 (dd, J=8.0, 1.0 Hz, 1H), 8.6 (br s, 1H).

5-Bromo-4-methylspiro[cyclohexane-1,3-[3H]indol]-2 (1H)-one.

A solution of the above oxindole (0.44 g, 2.0 mmol) in CHCl$_3$ (10 mL) with sodium acetate (0.28 g, 3.4 mmol) is cooled to 0° C. and treated with bromine (0.11 mL, 2.0 mmol) in CHCl$_3$ (4 mL). After 30 min. the mixture is warmed to RT and stirred an additional hour. The reaction mixture is poured into sat. sodium hydrogen carbonate solution and extracted with EtOAc (×2), the combined organic layers were washed with water, sat. sodium hydrogen carbonate solution, water, dried (MgSO4), and evaporated to give an off-white solid which was purified by column chromatography (SiO$_2$, ethyl acetate: hexane 2:4) to afford (0.2 g, 0.7 mmol, 35%) of the product: $^1$H NMR (CDCl$_3$) δ1.2–1.45 (m, 1H), 1.55–1.75 (m, 4H), 1.85–1.95 (d, J=13 Hz, 1H), 2.05–2.35 (m, 4H), 2.47 (s, 3H), 6.62 (d, J=8.0 Hz, 1H), 7.4 (d, J=8.0, Hz, 1H), 8.47 (br s, 1H).

5-(3-chlorophenyl)-4-methylspiro[cyclohexane-1,3-[3H]indol]-2(1H)-one

A solution of the above 5-bromo-4-methyl-oxindole (0.1 g, 0.34 mmol) and tetrakis(triphenylphosphine) palladium (0.05 g, 0.04 mmol) in dimethoxyethane (10 mL) was stirred under N$_2$ for 20 min. To this mixture was then added 3-chlorophenylboronic acid (0.065 g, 0.41 mmol) and sodium carbonate (0.1 g, 1.0 mmol) in water (3 mL). The solution was brought to reflux for 6 h then cooled to RT, poured into water and extracted with EtOAc (×3). The combined organic extracts were washed with water, brine, dried (MgSO$_4$), and evaporated. The residue was purified by column chromatography (SiO$_2$, ethyl acetate: hexane 1:3) to afford the subtitled compound (0.077 g, 0.2 mmol, 70%) as a yellow solid: m.p. 164–165° C.; $^1$H NMR (CDCl$_3$) δ1.25–1.4 (m, 1H), 1.6–1.7 (m, 3H), 1.78 (d, J=12.0 Hz, 2H), ), 1.9 (d, J=13.0 Hz, 1H), 2.1–2.35 (m, 3H), 2.49 (s, 3H), 6.75 (d, J=7.9 Hz, 1H), 7.1 (d, J=7.9, Hz, 1H), 7.15–7.18 (m, 1H), 7.26–7.35 (m, 3H), 7.88 (br s, 1H);13C-NMR (CDCl$_3$) □ 16.71 (q), 20.7, 25.5, 29.9 (t), 48.5 (s), 107.1, 127.0, 128.0, 129.4, 129.5, 130 (d), 132.2, 133.0, 134.0, 136.6, 140.1, 144, 182.6 (s); MS (EI) m/z 326, (M+H)+w/1 Cl.

EXAMPLE 101

5-(1,2-Dihydro-2-oxospiro[cyclohexane-1,3-[3H]indol]-5-yl)-1H-3nitropyrrole-2-carbonitrile To a solution of tert-butyl 2-cyano-5-(4,4-dimethyl-2-oxo-1,4-dihydro-2H-3,1-benzoxazin-6-yl)-1H-pyrrole-1-carboxylate (0.11 g, 2.6 mmol) in TFA (5 mL) at 0° C. was added silver nitrate (1.1 eq, 49 mg, 2.86 mmol). After 5 min the reaction was poured onto ice, DCM (5 mL) was added and the layers were separated. The aqueous layer was extracted with DCM (3×5 mL) and the combined organic layer was washed with brine, dried over MgSO$_4$ and concentrated in vacuo. The residue was purified by flash column chromatography on silica gel eluting with 40% ethyl acetate/ hexane to 5-(1,2-dihydro-2-oxospiro[cyclohexane-1,3-[3H]indol]-5-yl)-1H-3-nitropyrrole-2-carbonitrile (20 mg, 21%) as a white solid. $^1$H NMR (400 MHz, d6-DMSO) δ1.4–1.9 (10H, m), 6.94 (d, 1H, J=8.1Hz), 7.47 (dd, 1H, J=8.1, 1.75 Hz), 7.73 (s, 1H), 7.75 (d, 1H, J=1.75 Hz), 10.6 (s, 1H), 13.4 (s, 1H). M/z (ES) 335 (M−H)$^-$. Anal. calcd for C18H16N4O3, C, 64.3, H, 4.79, N, 16.7. Found, C, 62.2, H, 5.20, N, 15.1.

EXAMPLE 102

5(2-Nitro-1H-Pyrrol-3-yl)spiro[cyclohexane-1,3-[3H]indol]-2(1H)-one

According to a procedure described in *J. Med. Chem.* 1983, 26, p.800, succinic anhydride (2.0 g, 20 mmol) and spiro[cyclohexane-1,3-[3H]indol]-2(1H)-one (4.03 g, 20 mmol) gave 4-oxo-4-(1,2-dihydro-2-oxospiro[cyclohexane-1,3-[3H]indol]-5-yl)butanoic acid (100%). $^1$H NMR (d$_6$-DMSO, 300 MHz) δ1.5–2.0 (m, 10H), 2.56 (t, 1H, J=6Hz), 3.20 (t, 1H, J=6Hz), 6.95 (d, 1H, J=8.1 Hz), 7.91 (d, 1H, J=8.1 Hz), 8.0 (s, 1H), 10.7 (s, 1H), 12.1 (s, 1H). MS (EI) m/z 300 (M−H)$^-$.

According to a procedure described in *J. Org. Chem.* 1984, p.3840 4-oxo-4-(1,2-dihydro-2-oxospiro[cyclohexane-1,3-[3H]indol]-5-yl)butanoic acid (5.64 g, 18 mmol) and thallium nitrate gave dimethyl-2-(1,2-dihydro-2-oxospiro[cyclohexane-1,3-[3H]indol]-5-yl)succinate (7.95 g, 18 mmol) as a white powder (71%). $^1$H NMR (d$_6$-DMSO, 300 MHz) δ1.44–1.84 (m, 1H), 2.68 (dd, 1H, J=4.97, 16.9Hz), 3.06 (dd, 1H, J=16.9, 10.5 Hz), 3.5 (s, 6H), 4.03 (dd, 1H, J=4.9, 10.5 Hz), 6.78 (d, 1H, J=7.9 Hz), 7.07 (d, 1H, J=7.9 Hz), 7.39 (s, 1H), 10.31 (s, 1H). MS (EI) m/z 346 (M+H)$^+$.

To a solution of dimethyl-2-(1,2-dihydro-2-oxospiro[cyclohexane-1,3-[3H]indol]-5-yl)succinate (2.0 g, 6.0 mmol) in THF (30 mL) was added LiBH$_4$ (2.5 eq, 0.33 g, 15 mmol). The solution was refluxed for 1.5 h, cooled and quenched by the careful addition of 1N HCl. The aqueous layer was extracted with DCM (3×10 mL) and the combined organic layer was washed with brine, dried over MgSO$_4$ and purified by flash column chromatography on silica gel eluting with 5% MeOH/ethyl acetate to give of 2-(1,2-dihydro-2-oxospiro[cyclohexane-1,3-[3H]indol]-5-yl)butan-1,4-diol (78 g, 47%) as a white solid. $^1$H NMR (300 MHz, d$_6$-DMSO) δ1.53–1.60 (n, 1H), 1.72 (m, 2H), 1.93 (m, 7H), 2.69 (m, 1H), 3.26 (m, 2H), 3.46 (t, 2H, J=5.8 Hz), 4.35 (t, 1H, J=5.2 Hz), 4.55 (t, 1H, J=5.2 Hz), 6.70 (d, 1H, J=7.8 Hz), 6.94 (d, 1H, J=7.8 Hz), 7.03 (s, 1H), 10.2 (s, 1H). M/z (ES) 276 (M+H)$^+$. Anal. calcd for C16H21NO3, C, 96.79, H, 7.69, N, 5.09. Found, C, 70.02, H, 7.64, N, 5.02.

Oxalyl chloride (4 eq, 1.0 mL, 11 mmol) in DCM (40 mL) at −78° C. was treated with DMSO (8 eq, 1.62 mL, 22 mmol). After 2 min a solution of 2-(1,2-dihydro-2-oxospiro[cyclohexane-1,3-[3H]indol]-5-yl)butan-1,4-diol (1 eq, 0.78 g, 2.9 mmol) in DMSO:DCM (1:3, 5 mL) was added followed 15 min later by addition of triethylamine (18 eq, 7.2 mL, 52 mmol). The solution was removed from the cooling bath and allowed to reach room temperature. The solution was filtered through celite, concentrated in vacuo and redissolved in MeOH (10 mL). A large excess of ammonium acetate was added and the solution was heated to 60° C. for 1 h then stored in a refrigerator for 16 h. The solution was partitioned between DCM and water. The layers were separated and the aqueous layer was extracted with DCM (3×10 mL) and the combined organic layer was washed with brine, dried over MgSO$_4$ and purified by flash column chromatography on silica gel eluting with 60% ethyl acetate/hexane to give 5-(1H-pyrrol-3-yl)spiro[cyclohexane-1,3-[3H]indol]-2(1H)-one (0.12 g, 19%) as a white solid. $^1$H NMR (300 MHz, d$_6$-DMSO) δ1.79–1.83 (m, 2H), 1.95 (m, 6H), 6.37 (s, 1H), 6.73 (m, 2H), 7.13 (s, 1H), 7.29 (d, 1H, J=8 Hz), 10.17 (s, 1H), 10.83 (s, 1H). M/z (ES) 253 (M+H)$^+$.

To a solution of give 5-(1H-pyrrol-3-yl)spiro[cyclohexane-1,3-[3H]indol]-2(1H)-one (45 mg, 0.17 mmol) in DCM:MeCN (1:1, 5 mL) at −40° C. sequentially was added silver nitrate (1.1 eq, 32 mg, 0.19 mmol) and a solution of acetyl chloride (1.1 eq, 0.01 mL, 0.19 mmol) in MeCN (0.5 mL). After 1 h the cooling bath was removed and the reaction was allowed to stir for 16 h. DCM (20 mL) was added and the suspension was filtered through celite, washed sequentially with sat. aq. NaHCO$_3$ and brine, dried over MgSO$_4$ and concentrated in vacuo. The residue was purified by flash column chromatography on silica gel eluting with 40% ethyl acetate/hexane to give 5-(2-nitro-1H-pyrrol-3-yl)spiro[cyclohexane-1,3-[3H]indol]-2(1H)-one (20 mg, 40%) as a yellow powder. $^1$H NMR (300 MHz, d$_6$-DMSO) δ1.63–1.95 (mn, 10J), 6.44 (t, 1H, J=2.69 Hz), 6.97 (d, 1H, J=8.1 Hz), 7.22 (t, 1H, J=2.9 Hz), 7.44 (dd, 1H, J=8.1, 1.7 Hz), 7.79 (d, 1H, J=1.4 Hz), 9.39 (s, 1H), 11.85 (s, 1H). M/z 310 (M−H)$^-$.

EXAMPLE 103

5-(4-Chlorophenyl)spiro[cyclohexane-1,3-[3H]indol]-2(1H)-one

The title compound was prepared from CAT-817819 (1.9 g, 7.8 mmol) and 4-bromochlorobenzene (1.0 g, 5.2 mmol) according to the method for Example 18 to afford the product (0.68 g, 42%) as an off white solid: mp. 226–229° C.; $^1$H NMR (DMSO-d$_6$) δ10.41 (br s, 1H), 7.68–7.63 (m, 3H), 7.49–7.46 (m, 3H), 6.93 (d, 1H, J=8.0 Hz), 1.99–1.82 (m, 2H), 1.76–1.51 (m, 8H); MS (EI) m/z 311/313 [M]$^+$; C19H18ClON requires C, 73.19; H, 5.82; N, 4.49; Found C, 73.13; H, 5.68; N, 4.40.

EXAMPLE 104

5(2-Chlorophenyl)spiro[cylohexane-1,3-[3H]indol]-2(1H)-one

The title compound was prepared from CAT-817819 (1.9 g, 7.8 mmol ) and 2-bromochlorobenzene (1.0 g, 5.2 mmol) according to the method for Example 18 to afford the title compound (0.68 g, 42%) as an off white solid: mp. 174–175° C.; $^1$H NMR (DMSO-d$_6$) δ10.43 (br s, 1H), 7.56–7.52 (m, 2H), 7.43–7.33 (m, 3H), 7.25 (dd, 1H, J=8.0 and 1.7 Hz), 6.93 (d, 1H, J=8.0 Hz), 1.92–1.79 (m, 2H) and 1.77–1.43 (M, 8H); MS (EI) m/z 311/313 [M]$^+$; Anal. Calc. For C$_{19}$H$_{18}$ClON: C, 73.19; H, 5.82; N, 4.49; Found C, 73.10; H, 5.86; N, 4.30.

EXAMPLE 105

5(1,2-Dihydro-2-oxospiro[cyclopentane-1,3-3H]indol]-5-yl)-2-furancarbonitrile

The title compound was prepared from CAT-830083 (0.9 g, 3.9 mmol ) and 5-cyano-furancarbonitrile (0.5 g, 2.6 mmol) according to the method for Example 18 to afford the title compound (0.35, 49%) as an off white solid: mp. 193–194° C.; $^1$H NMR (DMSO-d$_6$) δ10.55 (br s, 1H), 7.69–7.63 (m, 3H), 7.15 (d, 1H, J=3.8 Hz), 6.92 (d, 1H, J=8.1 Hz), 2.00–1.83 (m, 8H); MS (ESI (−)) m/z 277

What is claimed:

1. A compound of the Formula 1:

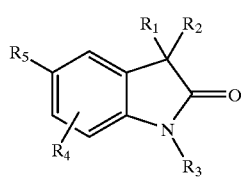

wherein:

R₁ and R₂ are joined to form a ring selected from the group consisting of:
—CH₂(CH₂)nCH₂—; —CH₂CH₂CMe₂CH₂CH₂—; —O(CH₂)mCH₂—; O(CH₂)pO;
—CH₂CH₂OCH₂CH₂—; and —CH₂CH₂N(H or alkyl)CH₂CH₂—;

n is an integer from 0 to 5;
m is an integer from 1 to 4;
p is an integer from 1 to 4;

R₃ is selected from the group consisting of H, OH, NH₂, C₁ to C₆ alkyl, substituted C₁ to C₆ alkyl, C₃ to C₆ alkenyl, alkynyl or substituted alkynyl, and COR^A;

R^A is selected from the group consisting of H, C₁ to C₃ alkyl, substituted C₁ to C₃ alkyl, C₁ to C₃ alkoxy, substituted C₁ to C₃ alkoxy, C₁ to C₃ aminoalkyl, and substituted C₁ to C₃ aminoalkyl;

R₄ is selected from the group consisting of H, halogen, CN, NH₂, C₁ to C₆ alky, substituted C₁ to C₆ alkyl, C₁ to C₆ alkoxy, substituted C₁ to C₆ alkoxy, C₁ to C₆ aminoalkyl, and substituted C₁ to C₆ aminoalkyl;

R₅ is a benzene ring with substituents X, Y and Z as shown below:

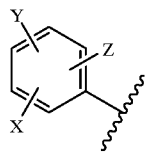

wherein:

X is selected from the group consisting of halogen, OH, CN, C₁ to C₃ alkyl, substituted C₁ to C₃ alkyl, C₁ to C₃ alkoxy, substituted C₁ to C₃ alkoxy, C₁ to C₃ thioalkyl, substituted C₁ to C₃ thioalkyl, S(O)alkyl, S(O)₂alkyl, C₁ to C₃ aminoalkyl, substituted C₁ to C₃ aminoalkyl, NO₂, C₁ to C₃ perfluoroalkyl, 5 or 6 membered heterocyclic ring containing 1 to 3 heteroatoms, COR^B, OCOR^B, and NR^C COR^B;

R^B is H, C₁ to C₃ alkyl, substituted C₁ to C₃ alkyl, aryl, substituted aryl, C₁ to C₃ alkoxy, substituted C₁ to C₃ alkoxy, C₁ to C₃ aminoalkyl, or substituted C₁ to C₃ aminoalkyl;

R^C is H, C₁ to C₃ alkyl, or substituted C₁ to C₃ alkyl;

Y and Z are independently selected from the group consisting of H, halogen, CN, NO₂, C₁ to C₃ alkoxy, C₁ to C₃ alkyl, and C₁ to C₃ thioalkyl;

or a pharmaceutically acceptable salt thereof.

2. The compound of claim 1 having the structure:

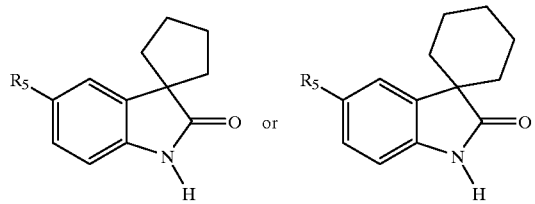

wherein:

R⁵ is a disubstituted benzene ring containing the substituents X and Y as shown below:

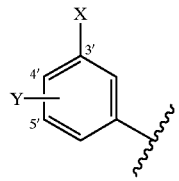

X is selected from the group consisting of halogen, CN, C₁ to C₃ alkoxy, C₁ to C₃ alkyl, NO₂, C₁ to C₃ perfluoroalkyl, 5 membered heterocyclic ring containing 1 to 3 heteroatoms and C₁ to C₃ thioalkoxy; and Y is a substituent on the 4' or 5' position of the disubstituted benzene ring and is selected from the group consisting of H, halogen, CN, NO₂, C₁ to C₃ alkoxy, C₁ to C₄ alkyl, and C₁ to C₃ thioalkyl;

or a pharmaceutically acceptable salt thereof.

3. The compound of claim 1 which is selected from the group of:

i) 3-(1',2'-Dihydro-2'-oxospiro[cyclohexane-1,3'-[3H]indol-5'-yl)benzaldehyde;

ii) 3-(1',2'-Dihydro-2'-oxospiro[cyclohexane-1,3'-[3H]indol-5'-yl)benzaldehyde oxime; and iii) 3-(1',2'-Dihydro-2'-oxospiro [cyclohexane-1,3'-[3H]indol-5'-yl)benzaldehyde methyloxime ether;

or a pharmaceutically acceptable salt thereof.

4. The compound of claim 1 which is selected from the group of:

i) 3-(1',2'-Dihydro-2'-oxospiro [cyclohexane-1,3'-[3H]indol-5'-yl)benzonitrile;

ii) 3-(1,2-Dihydro-2-oxospiro[cyclohexane-1,3-[3H]indol]-5-yl)-5-fluorobenzonitrile;

iii) 3-(1,2-Dihydro-2-oxospiro[cyclohexane-1,3-[3H]indol]-5-yl)-4-fluorobenzonitrile;

iv) 3-(1'-Diethoxymethyl-1',2'-dihydro-2'-oxospiro[cyclohexane-1,3'-[3H]indol]-5'-yl)-5-fluorobenzonitrile;

v) 3-(7'-Bromo-1',2'-dihydro-2'-oxospiro[cyclohexane-1,3'-[3H]indol]-5'-yl)-5-fluoro-benzonitrile;

vi) 3-(7'-Nitro-1',2'-dihydro-2'-oxospiro[cyclohexane-1,3'-[3H]indol]-5'-yl)-5-fluoro-benzonitrile;

vii) 3-(7'-Amino-1',2'-dihydro-2'-oxospiro[cyclohexane-1,3'-[3H]indol]-5'-yl)-5-fluoro-benzonitrile;

viii) 2-fluoro-4-(1',2'-Dihydro-2'-oxospiro[cyclohexane-1,3'-[3H]indol-5'-yl) benzaldehyde oxime; and ix) 3-(1',2'-Dihydro-2'-oxospiro[cyclohexane-1,3'-[3H]indol-5'-yl)phenylacetonitrile;

or a pharmaceutically acceptable salt thereof.

5. The compound of claim 1 which is selected from the group of:

i) 5-(3-chlorophenyl)spiro[cyclohexane-1,3-[3H]indol]-2(1H)-one;

ii) 5'-(3-Chloro-4-fluorophenyl)spiro[cyclohexane-1,3'-[3H]indol]-2'(1'H)-one;

iii) 5'-(3-Fluorophenyl)spiro[cyclohexane-1,3'-[3H]indol]-2'(1'H)-one;

iv) 5'-(3,5-Difluorophenyl)spiro[cyclohexane-1,3'-[3H]indol]-2'(1'H)-one;

v) 5-(3,4-Difluorophenyl)spiro[cyclohexane-1,3-[3H]indol]-2(1H)-one;

vi) 5-[3-(Methylthio)phenyl]spiro[cyclohexane-1,3-[3H]indol]-2(1H)-one;

vii) 5'-[3-(Methysulfinylphenyl]spiro[cyclohexane-1,3'-[3H]indol]-2'(1'H)-one;

viii) 5-[3-(Methysulfonyl)phenyl]spiro[cyclohexane-1,3-[3H]indol]-2(1H)-one;

ix) 5'-(3-Chloro-5-fluorophenyl)spiro[cyclohexane-1,3'-[3H]indol]-2'(1'H)-one;

x) 5'-(5-Nitro-1H-pyrrol-2-yl)spiro[cyclohexane-1,3'-[3H]indol]-2'(1'H)-one; and xi) 5-(3-Fluoro-4-nitrophenyl)spiro[cyclohexane-1,3-[3H]indol]-2(1H)-one;

or a pharmaceutically acceptable salt thereof.

6. The compound of claim 1 which is selected from the group of:

i) 5-(3-Bromo-5-fluorophenyl)spiro[cyclohexane-1,3-[3H]indol]-2(1H)-one;

ii) 5'-(3-Fluoro-5-methylphenyl)spiro[cyclohexane-1,3'-[3H]indol]-2'(1'H)-one;

iii) 5'-(3-Nitrophenyl)spiro[cyclohexane-1,3'-[3H]indol]-2'(1'H)-one;

iv) 5-(3-Fluoro-5-nitrophenyl)spiro[cyclohexane-1,3-[3H]indol]-2(1H)-one;

v) 5'-(3-Hydroxyphenyl)spiro[cyclohexane-1,3'-[3H]indol]-2'(1'H)-one;

vi) 5-[4-Fluoro-3-nitrophenyl)spiro[cyclohexane-1,3-[3H]indol]-2(1H)-one;

vii) 5-(3-cyano-4-fluorophenyl)spiro[cyclohexane-1,3-[3H]indol]-2(1H)-one;

viii) 5'-(4-Cyano-3-fluorophenyl)-spiro[cyclohexane-1,3'-[3H]indol]-2'(1'H)-one; and ix) 2,3,5,6-Tetrahydro-5-(3-nitrophenyl)spiro[3H-indole-3,4-[4H]pyran]-2(1H)-one;

or a pharmaceutically acceptable salt thereof.

7. The compound of claim 1 which is selected from the group consisting of:

i) 5'-(3-Chlorophenyl)spiro[4,4-dimethylcyclohexane-1',3'-[3H]indol]-2'(1'H)-one;

ii) 5'-(3-Nitrophenyl)spiro[4,4-dimethylcyclohexane-1',3'-[3H]indol]-2'(1'H)-one;

iii) 2-fluoro-3-(1',2'-Dihydro-2'-oxospiro[cyclohexane-1,3'-[3H]indol-5'-yl) benzaldehyde oxime;

iv) 5'-(5-Chloro-3-methylbenzo[b]thien-2-yl)spiro[cyclohexane-1,3'-[3H]indol]-2'(1'H)-one; and v) 5-[4-Fluoro-3-(trifluoromethyl)phenyl]spiro[cyclohexane-1,3-[3H]indol]-2(1H)-one;

or a pharmaceutically acceptable salt thereof.

8. The compound of claim 1 which is selected from the group consisting of:

i) 5'-(4-Cyano-3-fluorophenyl)-spiro[cyclopentane-1,3'-[3H]indol]-2'(1'H)-one;

ii) 5'-(3-cyano-4-fluorophenyl)-spiro[cyclopentane-1,3'-[3H]indol]-2'(1'H)-one;

iii) 5'-(3-Chloro-4-fluorophenyl)-spiro[cyclopentane-1,3'-[3H]indol]-2'(1'H)-one;

iv) 5'-(3-Cyanophenyl)-spiro [cyclopentane-1,3'-[3H]indol]-2'(1'H)-one;

v) 5'-(3-Cyano-5-fluorophenyl)-spiro[cyclopentane-1,3'-[3H]indol]-2'(1'H)-one; and vi) 5'-(3-nitrophenyl)spiro[cyclopentane-1,3'-[3H]indol]-2'(1'H)-one;

or a pharmaceutically acceptable salt thereof.

9. The compound of claim 1 which is selected from the group consisting of:

i) 5'-(3-Chlorophenyl)spiro[1,3-dioxolane-2,3'-[3H]indol]-2'(1'H)-one; and ii) 5'-(3-Chlorophenyl)spiro[1,3-dioxane-2,3'-[3H]indol]-2'(1'H)-one;

or a pharmaceutically acceptable salt thereof.

10. A pharmaceutical composition comprising a compound of claim 1, or a pharmaceutically acceptable salt thereof, and a pharmaceutically acceptable carrier or excipient.

11. A method of inducing contraception in a mammal, the method comprising administering to a mammal in need thereof a pharmaceutically effective amount of a compound of claim 1, or a pharmaceutically acceptable salt thereof.

12. A method of treating or preventing benign or malignant neoplastic disease, the method comprising administering to a mammal in need thereof a pharmaceutically effective amount of a compound of claim 1, or a pharmaceutically acceptable salt thereof.

13. A method of treating or preventing benign or malignant neoplastic disease is selected from uterine myometrial fibroids, endometriosis, benign prostatic hypertrophy; carcinomas and adenocarcinomas of the endometrium, ovary, breast, colon, prostate, pituitary, meningioma or other hormone-dependent tumors.

* * * * *

UNITED STATES PATENT AND TRADEMARK OFFICE
CERTIFICATE OF CORRECTION

PATENT NO. : 6,391,907 B1
DATED : May 21, 2002
INVENTOR(S) : A. Fensome et al.

It is certified that error appears in the above-identified patent and that said Letters Patent is hereby corrected as shown below:

Column 1,
Line 17, replace "1998)." with -- 1988). --.
Line 29, after "complex", insert -- This complex binds to specific gene promoters present in the cell's DNA. --.
Line 40, replace "(WO 96/1997 A1 Jul. 4, 1996)"
with -- (WO 96/19997 A1 July 4, 1996) --.
Line 44, replace "Pr antagonists" with -- PR antagonists --.

Column 3,
Lines 15-25, delete the following structure:
"
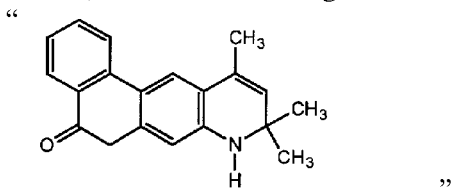
"

and insert the following structure
--
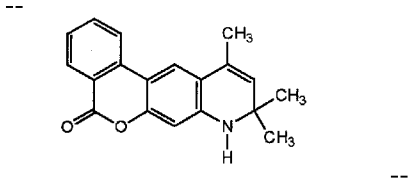
--

Column 4,
Lines 1-15, delete the following structure:
"
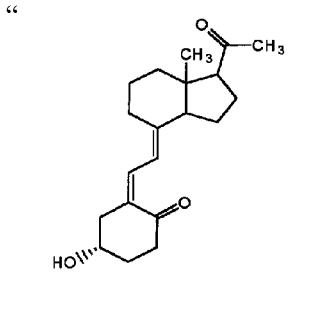
"

UNITED STATES PATENT AND TRADEMARK OFFICE
CERTIFICATE OF CORRECTION

PATENT NO. : 6,391,907 B1
DATED : May 21, 2002
INVENTOR(S) : A. Fensome et al.

It is certified that error appears in the above-identified patent and that said Letters Patent is hereby corrected as shown below:

Column 4, cont'd,
and insert the following structure:
--
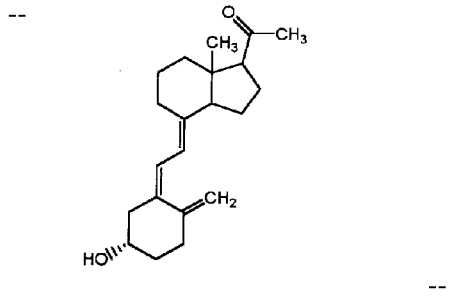
--

Column 5,
Lines 28-35, delete the following structure:
"
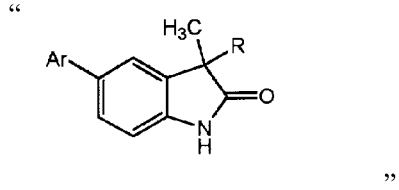
"

and insert the following structure:
--
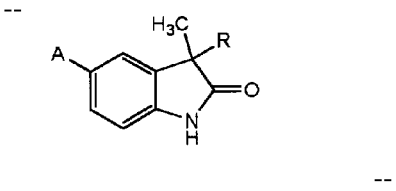
--

Column 9,
Line 14, replace "C3" with -- $C_3$ --.

Column 11,
Line 67, replace "though" with -- through --.

UNITED STATES PATENT AND TRADEMARK OFFICE
CERTIFICATE OF CORRECTION

PATENT NO. : 6,391,907 B1
DATED : May 21, 2002
INVENTOR(S) : A. Fensome et al.

It is certified that error appears in the above-identified patent and that said Letters Patent is hereby corrected as shown below:

Column 15,
Line 61, replace "mnL)." with -- mL). --.
Line 67, replace "(m:, 1H)" with -- (m, 1H) --.

Column 16,
Line 2, replace "c/m¯; " with -- $cm^{-1}$; --.
Line 47, replace "dimethyl-13-dihydro-" replace with -- dimethyl-1,3-dihydro --.

Column 18,
Line 14, replace "11H," with -- 1H, --.
Line 43, replace "(n, 1H)," with -- (m, 1H), --.

Column 19,
Line 27, replace "(d, 1H), J=1.7 Hz)," with -- (d, 1H, J=1.7 Hz), --.

Column 21,
Line 7, replace "(dd, 7.8 Hz, 1H)," with -- (dd, J=1.78, 1H), --.
Line 46, replace "14267," with -- 142.67, -- .
Line 63, replace "-[3H]indol] 2'(1H)-one" with -- -[3H]indol]-2'(1'H)-one --.

Column 22,
Line 26, replace "(r, 8H)," with -- (m, 8H), --.
Line 40, replace "C.;" with -- °C; -- .

Column 23,
Line 3, replace "(m, 1H)," with -- (m, 10H), --.

Column 25,
Line 21, replace "spiro cyclohexane" with -- spiro[cyclohexane --.

Column 26,
Line 50, replace "1H NMR" with -- $^1$H NMR --.

UNITED STATES PATENT AND TRADEMARK OFFICE
CERTIFICATE OF CORRECTION

PATENT NO. : 6,391,907 B1
DATED : May 21, 2002
INVENTOR(S) : A. Fensome et al.

It is certified that error appears in the above-identified patent and that said Letters Patent is hereby corrected as shown below:

Column 30,
Line 49, replace "5'-y-1H-" with -- 5'-yl)-1H- --.

Column 31,
Line 6, replace "bamate" with -- bamate. --.
Line 49, replace "(1')-one" with -- (1'H)-one --.

Column 33,
Line 67, replace "MHz) 671.13" with -- MHz) δ 1.13 --.

Column 34,
Line 13, replace "-2-oxospiro" with -- -2'-oxospiro --.
Line 23, replace "(2xx10 mL)," with -- (2x10 mL), --.

Column 35,
Line 8, replace "(2xmL)." with -- (2x20 ML) --.
Line 14, replace "(70 mg, 500%)" with -- (70 mg, 50%) --.
Line 37, replace "1,3'-3H]" with -- 1,3'-[3H] --.

Column 38,
Line 56, replace "yl)-2" with -- yl)-2- --.

Column 40,
Line 36, replace "-dimethy11,3-" with -- -dimethyl-1,3- --.

Column 41,
Line 16, replace "0.1" with -- 0.11 --.

Column 42,
Line 13, replace "5(3,3-Dimethyl-2-oxo-2,3dihydro"
with -- 5-(3,3-Dimethyl-2-oxo-2,3-dihydro- --.
Line 14, replace "4methyl" with -- 4-methyl --.

Column 44,
Line 41, replace "-4fluorophenyl)" with -- -4-fluorophenyl) --.

UNITED STATES PATENT AND TRADEMARK OFFICE
CERTIFICATE OF CORRECTION

PATENT NO. : 6,391,907 B1
DATED : May 21, 2002
INVENTOR(S) : A. Fensome et al.

It is certified that error appears in the above-identified patent and that said Letters Patent is hereby corrected as shown below:

Column 46,
Line 33, replace "-5-yl)-" with -- -5-yl)-5- --.

Column 47,
Line 49, replace "thiophene2-" with -- thiophene-2- --.

Column 48,
Line 63, replace "tal medium" with -- tal medium. --.

Column 50,
Line 13, replace "growth medium" with -- growth medium. --.

Column 52,
Line 44, replace "un-available." with -- unavailable --.

Column 55,
Line 11, replace "5(3-" with -- 5-(3- --.
Line 16, replace "nip." with -- mp. --.
Line 35, replace "(50 mnL)" with -- (50 mL) --.

Column 57,
Line 22, replace "rmp" with -- mp --.

Column 59,
Line 60, replace "3H]" with -- [3H] --.

Column 60,
Line 31, replace "indol)-2" with -- indol]-2 --.
Line 56, replace "-3nitropyrrole-2-" with -- -3-nitropyrrole-2- --.

Column 61,
Line 12, replace "5(2-Nitro" with -- 5-2-Nitro --.

UNITED STATES PATENT AND TRADEMARK OFFICE
CERTIFICATE OF CORRECTION

PATENT NO.    : 6,391,907 B1
DATED         : May 21, 2002
INVENTOR(S)   : A. Fensome et al.

It is certified that error appears in the above-identified patent and that said Letters Patent is hereby corrected as shown below:

<u>Column 62,</u>
Line 22, replace "(mn, l0J)," with -- (m, l0H), --.
Line 43, replace "5(2-" with -- 5-(2- --.
Line 58, replace "5(1,2-" with -- 5-(1,2- --.

<u>Column 63,</u>
Line 41, replace "$C_1$ to $C_6$ alky," with -- $C_1$ to $C_6$ alkyl --.

Signed and Sealed this

Sixth Day of May, 2003

JAMES E. ROGAN
*Director of the United States Patent and Trademark Office*